US008071364B2

(12) United States Patent
Cooper et al.

(10) Patent No.: US 8,071,364 B2
(45) Date of Patent: Dec. 6, 2011

(54) GENE THERAPY USING TRANSPOSON-BASED VECTORS

(75) Inventors: Richard Cooper, Baton Rouge, LA (US); Frederick M. Enright, Baton Rouge, LA (US); William C. Fioretti, Addison, TX (US)

(73) Assignees: TransGenRx, Inc., Baton Rouge, LA (US); The Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 1451 days.

(21) Appl. No.: 10/583,812

(22) PCT Filed: Dec. 24, 2004

(86) PCT No.: PCT/US2004/043092
§ 371 (c)(1),
(2), (4) Date: Jun. 22, 2006

(87) PCT Pub. No.: WO2005/062881
PCT Pub. Date: Jul. 14, 2005

(65) Prior Publication Data
US 2010/0199366 A1    Aug. 5, 2010

Related U.S. Application Data

(60) Provisional application No. 60/532,504, filed on Dec. 24, 2003, provisional application No. 60/565,371, filed on Apr. 26, 2004, provisional application No. 60/592,098, filed on Jul. 28, 2004.

(51) Int. Cl.
*C12N 5/00* (2006.01)
*C12N 15/00* (2006.01)
*C07H 21/02* (2006.01)
*C07H 21/04* (2006.01)
*C07K 2/00* (2006.01)

(52) U.S. Cl. ............... 435/320.1; 435/69.1; 435/325; 435/455; 536/23.1; 536/23.2; 536/23.4; 536/23.72; 530/300

(58) Field of Classification Search .................. None
See application file for complete search history.

(56) References Cited

U.S. PATENT DOCUMENTS

| | | | |
|---|---|---|---|
| 4,670,388 A | 6/1987 | Rubin et al. | |
| 4,870,009 A | 9/1989 | Evans et al. | |
| 4,914,025 A | 4/1990 | Manoil et al. | |
| 5,102,797 A | 4/1992 | Tucker et al. | |
| 5,162,215 A | 11/1992 | Bosselman et al. | |
| 5,212,080 A | 5/1993 | Nag et al. | |
| 5,512,483 A | 4/1996 | Mader et al. | |
| 5,556,782 A | 9/1996 | Cooper et al. | |
| 5,565,362 A | 10/1996 | Rosen | |
| 5,645,991 A | 7/1997 | Berg et al. | |
| 5,693,508 A * | 12/1997 | Chang | 435/6 |
| 5,703,055 A | 12/1997 | Felgner et al. | |
| 5,719,055 A * | 2/1998 | Cooper | 435/320.1 |
| 5,719,186 A | 2/1998 | Cooper et al. | |
| 5,733,779 A | 3/1998 | Reff | |
| 5,753,502 A | 5/1998 | Kilgannon et al. | |
| 5,861,478 A | 1/1999 | Jaynes | |
| 5,869,296 A | 2/1999 | Nag et al. | |
| 5,925,545 A | 7/1999 | Reznikoff et al. | |
| 5,948,622 A | 9/1999 | Reznikoff et al. | |
| 5,958,775 A | 9/1999 | Wickstrom et al. | |
| 5,962,410 A | 10/1999 | Jaynes et al. | |
| 5,965,443 A | 10/1999 | Reznikoff et al. | |
| 5,998,698 A | 12/1999 | Cooper et al. | |
| 6,080,912 A | 6/2000 | Bremel et al. | |
| 6,107,477 A | 8/2000 | Whitney et al. | |
| 6,140,129 A | 10/2000 | Cox et al. | |
| 6,156,568 A | 12/2000 | Cooper et al. | |
| 6,159,730 A | 12/2000 | Reff | |
| 6,159,736 A | 12/2000 | Reznikoff et al. | |
| 6,171,861 B1 | 1/2001 | Hartley et al. | |
| 6,218,185 B1 | 4/2001 | Shirk et al. | |
| 6,255,282 B1 | 7/2001 | Jaynes | |
| 6,258,571 B1 | 7/2001 | Chumakov et al. | |
| 6,261,554 B1 | 7/2001 | Valerio et al. | |
| 6,291,214 B1 | 9/2001 | Richards et al. | |
| 6,291,243 B1 | 9/2001 | Fogarty et al. | |
| 6,291,740 B1 | 9/2001 | Bremel et al. | |
| 6,303,568 B1 | 10/2001 | Jaynes et al. | |
| 6,316,692 B1 | 11/2001 | Readhead et al. | |
| 6,358,710 B1 | 3/2002 | Graves et al. | |
| 6,376,743 B1 | 4/2002 | Yanagimachi | |
| 6,475,798 B2 | 11/2002 | Fogarty et al. | |
| 6,489,458 B2 | 12/2002 | Hackett et al. | |
| 6,492,510 B2 | 12/2002 | Hasebe et al. | |

(Continued)

FOREIGN PATENT DOCUMENTS

AU    2003261096    1/2004

(Continued)

OTHER PUBLICATIONS

Davis, C.G., The Many Faces of Epidermal Growth Factor Repeats, New Biologist, May 1990, pp. 410-419, 2(5). Dunham, Rex A. et al., Enhanced Bacterial Disease Resistance of Transgenic Channel Catfish *Ictalurus punctatus* Possessing Cecropin Genes, Marine Biotechnology, Jun. 2002, pp. 38-344, vol. 4, No. Springer Verlag, New York, New York, US.
Fischer, R., et al., Antibody production by molecular farming in plants, Journal of Biological Regulators and Hoeostatic Agents, Apr. 2000, pp. 83-92, Vol. 14, No. 2, Wichtig Editore, Milan, Italy.
Gaub, Marie-Pierre et al., The Chicken ovalbumin promoter is under negative control which is relieved by steroid hormones, EMBO Journal, 1987, pp. 2313-2320, 6(8).
Giddings, Glynis, Transgenic plants as protein factories, Current Opinion in Biotechnology, Oct. 2001, pp. 450-454, Vol. 12, No. 5, London, Great Britain.
Schillberg, Stefan et al., Apoplastic and cytosolic expression of full-size antibodies and antibody fragments in *Nicotiana tabacum*, Transgenic Research, Aug. 1999, pp. 255-263, vol. 8, No. 4.

(Continued)

*Primary Examiner* — Sumesh Kaushal
(74) *Attorney, Agent, or Firm* — Kilpatrick Townsend & Stockton LLP

(57) ABSTRACT

Methods and compositions are presented for the administration of transposon based vectors to an animal or human to provide gene therapy to the animal or human.

7 Claims, 9 Drawing Sheets

U.S. PATENT DOCUMENTS

| | | |
|---|---|---|
| 6,503,729 B1 | 1/2003 | Bult et al. |
| 6,514,728 B1 | 2/2003 | Kai et al. |
| 6,515,199 B1 | 2/2003 | Petitte et al. |
| 6,528,699 B1 | 3/2003 | Meade et al. |
| 6,563,017 B2 | 5/2003 | Muramatsu et al. |
| 6,602,686 B1 | 8/2003 | Harrington et al. |
| 6,635,740 B1 | 10/2003 | Enright et al. |
| 6,670,185 B1 | 12/2003 | Harrington et al. |
| 6,680,058 B1 | 1/2004 | Enright et al. |
| 6,716,823 B1 | 4/2004 | Tang et al. |
| 6,730,822 B1 | 5/2004 | Ivarie et al. |
| 6,759,573 B2 | 7/2004 | Olhoft et al. |
| 6,825,396 B2 | 11/2004 | MacArthur |
| 6,852,510 B2 | 2/2005 | Bremel et al. |
| 6,939,959 B2 | 9/2005 | Hu |
| 7,005,296 B1 | 2/2006 | Handler |
| 7,019,193 B2 | 3/2006 | Ditullio et al. |
| 7,034,115 B1 | 4/2006 | Kawakami |
| 7,083,980 B2 | 8/2006 | Reznikoff et al. |
| 7,105,343 B1 | 9/2006 | Fraser, Jr. et al. |
| 7,129,390 B2 | 10/2006 | Ivarie et al. |
| 7,160,682 B2 | 1/2007 | Hackett et al. |
| 7,199,279 B2 | 4/2007 | Rapp |
| 7,294,507 B2 | 11/2007 | Harvey et al. |
| 7,335,761 B2 | 2/2008 | Harvey et al. |
| 7,375,258 B2 | 5/2008 | Harvey et al. |
| 7,381,712 B2 | 6/2008 | Christmann et al. |
| 7,527,966 B2 | 5/2009 | Cooper et al. |
| 7,566,777 B2 | 7/2009 | Enright et al. |
| 7,608,451 B2 | 10/2009 | Cooper et al. |
| 2001/0044937 A1 | 11/2001 | Schatten et al. |
| 2002/0007051 A1 | 1/2002 | Cheo et al. |
| 2002/0013955 A1 | 1/2002 | Ogden et al. |
| 2002/0016975 A1 | 2/2002 | Hackett et al. |
| 2002/0028488 A1 | 3/2002 | Singh et al. |
| 2002/0028513 A1 | 3/2002 | Fogarty et al. |
| 2002/0042137 A1 | 4/2002 | Richards et al. |
| 2002/0052047 A1 | 5/2002 | Hasebe et al. |
| 2002/0053092 A1 | 5/2002 | Readhead et al. |
| 2002/0055172 A1 | 5/2002 | Harrington |
| 2002/0056148 A1 | 5/2002 | Readhead et al. |
| 2002/0072097 A1 | 6/2002 | delCardayre et al. |
| 2002/0076797 A1 | 6/2002 | Lin |
| 2002/0079797 A1 | 6/2002 | Lin |
| 2002/0083479 A1 | 6/2002 | Winston et al. |
| 2002/0099015 A1 | 7/2002 | Barber |
| 2002/0104109 A1 | 8/2002 | Bremel et al. |
| 2002/0108132 A1 | 8/2002 | Rapp |
| 2002/0119573 A1 | 8/2002 | Shaw et al. |
| 2002/0129398 A1 | 9/2002 | Winston et al. |
| 2002/0132349 A1 | 9/2002 | Goryshin et al. |
| 2002/0133835 A1 | 9/2002 | Winston et al. |
| 2002/0138865 A1 | 9/2002 | Readhead et al. |
| 2002/0148000 A1 | 10/2002 | Shen |
| 2002/0150577 A1 | 10/2002 | Lee et al. |
| 2002/0151034 A1 | 10/2002 | Zhang et al. |
| 2002/0157125 A1 | 10/2002 | Lee et al. |
| 2002/0160507 A1 | 10/2002 | Novy et al. |
| 2002/0188105 A1 | 12/2002 | Craig et al. |
| 2002/0199214 A1 | 12/2002 | Rapp |
| 2003/0009026 A1 | 1/2003 | Hasebe et al. |
| 2003/0017534 A1 | 1/2003 | Buelow et al. |
| 2003/0055017 A1 | 3/2003 | Schwartz et al. |
| 2003/0056241 A1 | 3/2003 | Matsuda et al. |
| 2003/0061629 A1 | 3/2003 | Sutrave |
| 2003/0074680 A1 | 4/2003 | Lee et al. |
| 2003/0074681 A1 | 4/2003 | Macarthur |
| 2003/0101472 A1 | 5/2003 | Baltimore et al. |
| 2003/0115622 A1 | 6/2003 | Ponce De Leon et al. |
| 2003/0121062 A1 | 6/2003 | Radcliffe et al. |
| 2003/0126628 A1 | 7/2003 | Harvey et al. |
| 2003/0126629 A1 | 7/2003 | Rapp et al. |
| 2003/0140363 A1 | 7/2003 | Rapp |
| 2003/0143740 A1 | 7/2003 | Wooddell et al. |
| 2003/0150006 A1 | 8/2003 | Petitte et al. |
| 2003/0150007 A1 | 8/2003 | Savakis et al. |
| 2003/0154502 A1 | 8/2003 | Wimmer et al. |
| 2003/0167492 A1 | 9/2003 | Lee et al. |
| 2003/0170888 A1 | 9/2003 | Van de Lavoir et al. |
| 2003/0172387 A1 | 9/2003 | Zhu et al. |
| 2003/0177516 A1 | 9/2003 | Horseman et al. |
| 2003/0182672 A1 | 9/2003 | Graham et al. |
| 2003/0182675 A1 | 9/2003 | Etches et al. |
| 2003/0217375 A1 | 11/2003 | Zcharia et al. |
| 2003/0221206 A1 | 11/2003 | Schatten et al. |
| 2003/0224519 A1 | 12/2003 | Harrington et al. |
| 2004/0006776 A1 | 1/2004 | Meade et al. |
| 2004/0018624 A1 | 1/2004 | Harrington et al. |
| 2004/0019922 A1 | 1/2004 | Ivarie et al. |
| 2004/0040052 A1 | 2/2004 | Radcliffe et al. |
| 2004/0110143 A1 | 6/2004 | Bennett et al. |
| 2004/0142475 A1 | 7/2004 | Barman et al. |
| 2004/0158882 A1 | 8/2004 | Ivarie et al. |
| 2004/0172667 A1 | 9/2004 | Cooper et al. |
| 2004/0197910 A1 | 10/2004 | Cooper et al. |
| 2004/0203158 A1 | 10/2004 | Hackett et al. |
| 2004/0210954 A1 | 10/2004 | Harvey et al. |
| 2004/0226057 A1 | 11/2004 | Christmann et al. |
| 2004/0235011 A1 | 11/2004 | Cooper et al. |
| 2004/0255345 A1 | 12/2004 | Rapp et al. |
| 2005/0003414 A1 | 1/2005 | Harvey et al. |
| 2005/0004030 A1 | 1/2005 | Fischetti et al. |
| 2005/0034186 A1 | 2/2005 | Harvey et al. |
| 2005/0050581 A1 | 3/2005 | Harvey et al. |
| 2005/0066383 A1 | 3/2005 | Harvey |
| 2005/0176047 A1 | 8/2005 | Harvey et al. |
| 2005/0198700 A1 | 9/2005 | Christmann et al. |
| 2005/0208038 A1 | 9/2005 | Fischetti et al. |
| 2005/0273872 A1 | 12/2005 | Sang et al. |
| 2005/0273873 A1 | 12/2005 | Christmann et al. |
| 2006/0046248 A1 | 3/2006 | Rapp et al. |
| 2006/0121509 A1 | 6/2006 | Hermiston et al. |
| 2006/0123488 A1 | 6/2006 | Ivarie et al. |
| 2006/0123504 A1 | 6/2006 | Leavitt et al. |
| 2006/0171921 A1 | 8/2006 | Ivarie et al. |
| 2006/0185024 A1 | 8/2006 | Ivarie et al. |
| 2006/0185029 A1 | 8/2006 | Ivarie et al. |
| 2006/0188478 A1 | 8/2006 | Ivarie et al. |
| 2006/0210977 A1 | 9/2006 | Kaminski |
| 2006/0218652 A1 | 9/2006 | Horn et al. |
| 2006/0236413 A1 | 10/2006 | Ivics et al. |
| 2006/0258603 A1 | 11/2006 | Ivics et al. |
| 2007/0009991 A1 | 1/2007 | Horseman et al. |
| 2007/0022485 A1 | 1/2007 | Takeda et al. |
| 2007/0113299 A1 | 5/2007 | Harvey et al. |
| 2008/0235813 A1 | 9/2008 | Cooper et al. |
| 2008/0235815 A1 | 9/2008 | Cooper et al. |
| 2010/0081789 A1 | 4/2010 | Cooper et al. |
| 2010/0099148 A1 | 4/2010 | Cooper et al. |
| 2010/0261227 A1 | 10/2010 | Cooper |
| 2011/0162096 A1 | 6/2011 | Cooper et al. |

FOREIGN PATENT DOCUMENTS

| | | |
|---|---|---|
| EP | 1375654 | 1/2004 |
| EP | 1700914 A1 | 9/2006 |
| EP | 1364205 B1 | 5/2007 |
| EP | 1539785 | 5/2009 |
| EP | 1592789 | 5/2009 |
| JP | 2000512149 | 9/2000 |
| JP | 2001513336 | 9/2001 |
| JP | 2002238559 | 8/2002 |
| WO | 8900199 | 1/1989 |
| WO | 9012866 | 11/1990 |
| WO | WO 92/20316 | 11/1992 |
| WO | WO 93/24626 | 12/1993 |
| WO | WO 94/20608 | 9/1994 |
| WO | 9501095 | 1/1995 |
| WO | 9501424 | 1/1995 |
| WO | WO 95/31566 | 11/1995 |
| WO | WO 97/47739 | 12/1997 |
| WO | WO 99/09817 | 3/1999 |
| WO | WO 99/19472 | 4/1999 |
| WO | WO 99/42569 | 8/1999 |
| WO | WO 99/40213 | 9/1999 |
| WO | WO 00/11151 | 3/2000 |
| WO | WO 00/30437 | 6/2000 |
| WO | WO00/23579 A9 | 9/2000 |

| | | |
|---|---|---|
| WO | WO 00/56932 | 9/2000 |
| WO | WO 01/14537 | 3/2001 |
| WO | WO 01/17344 | 3/2001 |
| WO | WO 01/19846 | 3/2001 |
| WO | WO 01/23525 | 4/2001 |
| WO | WO 01/26455 | 4/2001 |
| WO | WO 01/43540 | 6/2001 |
| WO | WO 01/71019 A1 | 9/2001 |
| WO | WO 01/73094 | 10/2001 |
| WO | 0183786 | 11/2001 |
| WO | WO 01/85965 | 11/2001 |
| WO | 0202738 | 1/2002 |
| WO | 0246430 | 6/2002 |
| WO | WO 02/47475 | 6/2002 |
| WO | WO 02/063293 | 8/2002 |
| WO | WO 03/014344 | 2/2003 |
| WO | WO 03/024199 | 3/2003 |
| WO | WO 03/025146 | 3/2003 |
| WO | WO 03/048364 | 6/2003 |
| WO | WO 03/048364 A2 | 6/2003 |
| WO | WO 03/064627 | 8/2003 |
| WO | 2004003157 | 1/2004 |
| WO | WO 2004/009792 A2 | 1/2004 |
| WO | WO 2004/047531 | 6/2004 |
| WO | 2004067706 | 8/2004 |
| WO | 2004067707 | 8/2004 |
| WO | WO 2004/065581 A2 | 8/2004 |
| WO | WO 2004/067743 A1 | 8/2004 |
| WO | WO 2004/080162 A2 | 9/2004 |
| WO | 2004092351 | 10/2004 |
| WO | WO 2004/110143 | 12/2004 |
| WO | WO 2005/040215 A2 | 5/2005 |
| WO | 2005/062881 | 7/2005 |
| WO | 2005062881 | 7/2005 |
| WO | WO 2005/084430 A1 | 9/2005 |
| WO | WO 2006/024867 A2 | 3/2006 |
| WO | WO 2006/026238 A2 | 3/2006 |
| WO | WO 2006/053245 A2 | 5/2006 |
| WO | WO 2006/055040 A2 | 5/2006 |
| WO | WO 2006/055931 A2 | 5/2006 |
| WO | WO 2006/065821 A2 | 6/2006 |
| WO | 2006093847 | 9/2006 |
| WO | 2010036978 | 4/2010 |
| WO | 2010036979 | 4/2010 |
| WO | 2010118360 | 10/2010 |

OTHER PUBLICATIONS

Schillberg, S. et al., Molecular farming of recombinant antibodies in plants, Cellular and Molecular Life Sciences, Mar. 2003, pp. 433-445, vol. 60, No. 3, Birkhauser Verlag, Heidelberg, Germany.
Skolnick, J. et al., From Genes to Protein structure and function: novel applications of computational approaches in the genomic era, Trends in Biotech, 2000, pp. 34-39, 18.
Williamson, Christine M. et al., Expression of the Lysostaphin Gene of Staphylococcus simulans in a Eukaryotic System, Applied and Environmental Microbiology, Mar. 1994, pp. 771-776, vol. 60, No. 3.
AU 2003261096 Examiner's First Report dated Jun. 7, 2007.
EP 037621729 First Office Action dated Jun. 9, 2006.
EP 037621729 Response to First Office Action dated Oct. 18, 2006.
EP 037621729 Second Office Action dated Nov. 23, 2006.
EP 037621729 Response to Second Office Action dated Apr. 2, 2007.
EP 037621729 Third Office Action dated Apr. 24, 2007.
EP 037621729 Response to Third Office Action dated Aug. 31, 2007.
EP 038085635 First Office Action dated Oct. 5, 2005.
EP 038085635 Response to First Office Action dated Oct. 18, 2005.
EP 038085635 Search Report dated Jan. 23, 2007.
EP 038085635 Search Report dated Apr. 12, 2007.
EP 038085635 Second Office Action dated May 2, 2007.
EP 038002259 Office Action dated Aug. 30, 2006.
EP 038002259 Response to Office Action.
IN 99/KOL NP/2005 Official Action dated Jun. 17, 2006.
PCT/US03/20389 Written Opinion dated Jun. 17, 2004.
PCT/US03/41261 International Search Report dated Nov. 3, 2004.
PCT/US03/41335 International Search Report dated Nov. 3, 2004.
PCT/US03/41269 International Search Report dated May 18, 2004.
PCT/US04/043092 International Search Report and Written Opinion dated May 11, 2006.

Von Specht, M., English translation of Dissertation entitled Expression of a recombinant human protein in vitro and in vivo in oviduct cells of chickens, with human erythropoietin (hrEPO) as an example, 2002, pp. 49-68.
Abdel-Salam et al., Expression of Mouse Anticreatine Kinase (MAK33) Monoclonal Antibody in the Yeast Hansenula Polymorpha, Appl. Microbiol. Biotechnol., vol. 56, pp. 157-164, 2001.
Afanassieff et al., Intratesticular Inoculation of Avian Leukosis Virus (ALV) in Chickens—Production of Neutralizing Antibodies and Lack of Virus Shedding into Semen, Avian Diseases, vol. 40, pp. 841-852, Jan. 1, 1996.
Andra et al., Generation and Characterization of Transgenic Mice Expressing Cobra Venom Factor, Molecular Immunology, vol. 39, pp. 357-365, 2002.
Araki et al., Site-specific Recombination of a Transgene in Fertilized Eggs by Transient Expression of Cre Recombinase, Proc. Natl. Acad Sci. USA, vol. 92, pp.160-164, Jan. 1, 1995.
Argaud et al., Regulation of Rat Liver Glucose-6-Phosphatase Gene Expression in Different Nutritional and Hormonal States, Diabetes, vol. 45, pp. 1563-1571, Nov. 1, 1996.
Awade, A.C., On Hen Egg Fractionation: Applications of liquid Chromatography to the Isolation and the Purification of Hen Egg White and Egg Yolk Proteins, Z Lebensm Unters Forsch, vol. 202, pp. 1-14, Jan. 1, 1996.
Awade et al., Comparison of Three Liquid Chromatographic Methods for Egg-white Protein Analysis, Journal of Chromatography B., vol. 723, pp. 69-74, Jan. 1, 1999.
Beardsley, T., Gene therapy Setback: A tragic Death Clouds the Future of an Innovative Treatment Method, http://www.sciam.com/2000/0200issue/0200tech, pp. 1-2, Jun. 11, 2001.
Bell et al., Nucleotide Sequence of a cDNA Clone Encoding Human Preproinsulin, Nature, vol. 282, pp. 525-527, Nov. 29, 1979.
Bolli et al., Insulin Analogues and Their Potential in the Management of Diabetes Mellitus, Diabetologia, vol. 42, pp. 1151-1167, Jan. 1, 1999.
Brinster, R.L., Germline Stem Cell Transplanatation and Transgenesis, Science, vol. 296, pp. 2174-2176, Jun. 21, 2002.
Chatterjee et al., Retrofitting High Molecular Weight DNA Cloned in P1: Introduction of Reporter Genes, markers in Mammalian Cells and Generation of Nested Deletions, Genetic Analysis: Biomolecular Engineering, vol. 13, pp. 33-42, Jan. 1, 1996.
Ciampi, M.S. et al., Transposon Tn10 Provides a Promoter for transcription of adjacent sequences, Proc Natl Acad Sci USA, vol. 79(16), pp. 5016-5020, Aug. 1, 1982.
Ciftci et al., Applications of Genetic Engineering in Veterinary Medicine, Advanced Drug Delivery Reviews, vol. 43, pp. 57-64, Jan. 1, 2000.
Davis, M.A. et al., Tn10 Protects Itself at two levels from fortuitous activation by external promoters, Cell vol. 43(1), pp. 379-387, Nov. 11, 1985.
Dematteo et al., Engineering Tissue-Specific Expression of a Recombinant Adenovirus: Selective Transgene Transcription in the Pancreas Using the Amylase Promoter, Journal of Surgical Research, vol. 72, pp. 155-161, Jan. 1, 1997.
Desert, C. et al., Comparisons of Different Electrophoretic Separations of Hen Egg White Proteins, J. Agric. Food Chem., vol. 49, pp. 4553-4561, Jan. 1, 2001.
Dierich, A. et al., "Cell-Specificity of the Chicken Ovalbumin and Conalbumin Promoters", The EMBO Journal, pp. 2305-2312, Jan. 1, 1987.
Dong et al., Hepatic Insulin Production Type-1 Diabetes, Trends in Endocrinology & Metabolism, vol. 12 No. 10, pp. 441-446, Dec. 1, 2001.
Dupuy et al., Mammalian Germ-like Transgenesis by Transposition, Vol. 99 No. 7, pp. 4495-4499, Apr. 2, 2002.
Ebara et al., Possible Abnormalities of Chimeric Chicken Caused by the Introduction of Exgenous Genes into Checken Embryos via Primordial Germ Cells (PGC's), Asian-Aus. J. Anim. Sci. vol. 13 No. 11, pp. 1514-1517, Jan. 1, 2000.

Ebara et al., In Vivo Gene Transfer into Chicken Embryos via Primordial Germ Cells Using Green Fluorescent Protein as a Marker, *Journal of Reproduction and Development*, vol. 46 No. 2, pp. 79-83, Jan. 1, 2000.

Eggleston et al., A Sensitive and Rapid Assay for Homologous Recombination in Mosquito Cells: Impact of Vector Topology and Implications for Gene Targeting, *BMC Genetics*, vol. 2(21), pp. 1-9, Dec. 17, 2001.

Etches et al., Gene Transfer: Overcoming the Avian Problems (Abstract Provided), Proceedings, 5th World Congress, University of Guelph, vol. 20, pp. 97-101, Aug. 1, 1994.

Etches et al., Manipulation of the Avian Genome, *Manipulation of the Avian Genome*, pp. 322, Jan. 1, 1993.

Etches, R.J. et al., Strategies for the Production of Transgenic Chicken, *Methods in Molecular Biology*, vol. 62, pp. 433-450, Jan. 1, 1997.

Falqui et al., Reversal of Diabetes in Mice by Implantation of Human Fibroblasts Genetically Engineered to Release Mature Human Insulin, *Human Gene Therapy*, vol. 10, pp. 1753-1762, Jul. 20, 1999.

Fischer, S. et al., Regulated Transposition of a Fish Transposon in the Mouse Germ Line, *Proc. Natl. Acad. Sci. USA*, vol. 98(12), pp. 6759-6764, Jan. 1, 2001.

Fong, K.P. et al., The genes for benzene catabolism in *Pseudomonas putida* ML2 are flanked by two copies of the insertion of element IS1489, forming a class-I-type catabolic transposon Tn5542, *Plasmid*, vol. 43(2), pp. 103-110, Mar. 1, 2000.

Ghosh et al., Liver-directed Gene Therapy: Promises, Problems and Prospects at the Turn of the Century, *Journal of Hepatology*, vol. 32, pp. 238-252, Jan. 1, 2000.

Gibbins, A.M., Chickens as Bioreactors—Harvesting Commercially-Valuable Proteins from the Egg, *Agri-food Research in Ontario*, pp. 39-41, Jan. 1, 1996.

Gibbins, A.M.V., Transgenic Poultry Technology and Food Production, *Animal Biotechnology*, vol. 9 No. 3, pp. 173-179, Jan. 1, 1998.

Gibbins, A.M.V., The Chicken, the Egg, and the Ancient Mariner, *Nat. Biotechnol.*, vol. 16, No. 11, pp. 1013-1014, Jan, 1, 1998.

Gibbins et al., Genetically-engineered Poultry, *Lohmann Information*, vol. 21, pp. 3-6, Jan. 1, 1997.

Gibbins et al., Exploring the Product Possibilities Arising from Transgenic Poultry Technology, *Kungl. Skogs- och Lantbruksakademiens Tidsckrift*, vol. 136 No. 20, pp. 57-68, Jan. 1, 1997.

Ginsberg et al., The Road Ahead for Biologics Manufacturing, *Equity Research*, pp. 1-23, Jan 1, 2002.*

Hackett, P.B. et al., Development of Genetic Tools for Transgenic Animals, *Transgenic Animals in Agriculture*, pp. 19-35, Jan. 1, 1999.*

Han et al., Gene Transfer by Manipulation of Primordial Germ Cells in the Chicken, *AJAS*, vol. 7(3), pp. 427-434, Jan. 1, 1994.*

Harvey et al., Expression of Exogenous Protein in the White Egg of Transgenic Chickens, *Nature Biotechnology*, vol. 19 No. 4, pp. 396-399, Apr. 1, 2002.*

Hermann et al., Lipoprotein Receptors in Extraembryonic Tissues of the Chicken, *J. Biol. Chem.*, vol. 275 No. 22, pp. 16837-16844, Jun. 2, 2000.*

Hillel et al., Strategies for the Rapid Introgression of a Specific Gene Modification into a Commercial Poultry Flock from a Single Carrier, *Poultry Science*, vol. 72 No. 7, pp. 1197-1211, Jan. 1, 1993.*

Hong et al., Improved Transfection Efficiency of Chicken Gonadal Primordial Germ Cells for the Production of Transgenic Poultry, *Transgenic Research*, vol. 7, pp. 247-252, Jan. 1, 1998.*

Horn, A Versatile Vector Set for Animal Transgenesis, *Development Genes and Evolutiion*, vol. 210(12), pp. 630-637, 2000.*

Houdebine, L.M., The Methods to Generate Transgenic Animals and to Control Transgene Expression, *J. Biotechnol.*, vol. 98 Nos. 2-3, pp. 145-160, Sep. 25, 2002.*

Houdebine, L.M., Transgenic Animal Bioreactors, *Transgenic Research*, vol. 9(4-5), pp. 305-320, Oct. 1, 2000.*

Ivarie et al., Avian Transgenesis: Progress Towards the Promise, *TRENDS in Biotech*, vol. 21 (1), pp. 14-19, Jan. 1, 2003.*

Izsvak et al., Sleeping Beauty, A Wide Host-Range Transposon Vector for Genetic Transformation in Vertebrates, *J. Mol. Biol.*, vol. 302, pp. 93-102, Jan. 1, 2000.*

Jarvis et al., Influence of Different Signal Peptides and Prosequences on Expression and Secretion of Human Tissue Plasminogen Activator in the Baculovirus System, *The Journal of Biological Chemistry*, vol 268(22), pp. 16754-16762, Aug. 5, 1993.*

Kaminski et al., Design of a Nonviral vector for Site-selective, Efficient Intregration into the Human Genome, *The FASEB Journal*, vol. 16, pp. 1242-1247, Aug. 1, 2002.*

Kanda et al., Genetic Fusion of an a-Subunit Gene to the Follicle-Stimulating Hormone and Chorionic Gonadoptropin-b Subunit Genes: Production of a Bifunctional Protein, *Molecular Endocrinology*, vol. 13(13), pp. 1873-1881, Nov. 1, 1999.

Kay et al., Viral Vectors for Gene Therapy: the Art of Timing Infectious Agents into Vehicles of Therapeutics, *Nature Medecine*, vol. 7 No. 1, pp. 33-40, Jan. 1, 2001.

Kleckner, N. et al., Transposon Tn10: genetic organization, regulation and insertion specificity, *Fed Proc*, vol. 41(10), pp. 2649-2652, Aug. 1, 1982.

Kluin, Ph.M. et al., Proliferation of Spermatogonia and Sertoli Cells in Maturing Mice, *Anat. Embryol.*, vol. 169, pp. 73-78, Jan. 1, 1984.

Koga et al., The Medaka Fish To12 Transposable Element can Undergo Excision in Human and Mouse Cells, *J Hum Genet*, vol. 48 (5), pp. 231-235, Mar. 28, 2003.

Kousteni et al., Reversal of Bone Loss in Mice by Nongenotropic Signaling of Sex Steroids, *Science*, vol. 298, pp. 843-846, Oct. 25, 2002.

Kozak, M., At Least Six Nucleotides Preceding the AUG Initiator Codon Enhance Translation in Mammalian Cells, *J. Mol. Biol.*, vol. 196, pp. 947-950, 1987.

Kozak, M., Initiation of translation in prokaryotes and eukaryotes, *Gene*, vol. 234, pp. 187-208, 1999.

Kumaran, J.D.S. et al., The Normal Development of the Testes in the White Plymouth Rock, *Testis Development in White Plymouth Rock*, pp. 511-519, Jan. 1, 1948.

Lampe, D. et al., Hyperactive transposase mutants of the Himarl mariner transposon, *Proc. Natl. Acad. Sci. USA*, vol. 96, pp. 11428-11433, Sep. 1, 1999.

Marshak, S. et al., Purification of the B-Cell Glucose-sentitive Factor that Transactivates the Insulin Gene Differentially in Normal and Transformed Islet Cells, *Proc. Natl. Acad. Sci. USA*, vol. 93, pp. 15057-15062, Dec. 1, 1996.

Mather et al., The Mariner Transposable Element: A Potential Vector for Improved Integration of Transgenes into the Chicken Genome, *British Poulty Science*, vol. 41, pp. S27-S28, Sep. 1, 2000.

Meiss et al., Vectors for Dual Expression of Target Genes in Bacterial and Mammalian Cells, *BioTechniques*, vol. 29(3), pp. 476, 478, 480, 2000.

Mohammed et al., Deposition of Genetically Engineered Human Antibodies into the Egg Yolk of Hens, *Immunotechnology*, vol. 4, pp. 115-125, 1998.

Monroe, D. et al., The COUP-adjacent repressor (CAR) Element Participates in the Tissue-Specific Expression of the Ovalbumin Gene, *Biochemica et Biophysica Acta*, vol. 1517, pp. 27-32, Jan. 1, 2000.

Muramatsu, T. et al., Regulation of Ovalbumin Gene Expression, *Poultry and Avian Biology*, vol. 6 (2), pp. 107-123, Jan. 1, 1995.

Muzzin et al., Hepatic Insulin Gene Expressions as Treatment for aType 1 Diabetes Mellitus in Rats, *Mol Endo*, vol. 11 No. 6, pp. 833-837, Jan. 1, 1997.

Nicklin et al., Analysis of Cell-Specific Promoters for Viral Gene Therapy Targeted at the Vascular Endothelium, *Hypertension*, vol. 38, pp. 65-70, Jan. 1, 2001.

Oakberg, E., Duration of Spermatogenesis in the Mouse and Timing of Stages of the Cycle of the Seminiferous Epithelium, *Duration of Spermatogenesis*, pp. 507-516.

Ochiai, H. et al., Synthesis of Human Erythropoietin in Vivo in the Oviduct of Laying Hens by Localized in Vivo Gene Transfer using Electroporation, *Poultry Science*, vol. 77 (2), pp. 299-302, 1998.

Ono et al., Gene Transfer into Circulating Primorial Germ Cells of Quail Embryos, *Exp. Anim.*, vol. 4 No. 4, pp. 275-278, Jan. 1, 1995.

Osborne et al., A System for Insertional Mutagenesis and Chromosomal Rearrangement Using the Ds Transposon and Crelox, *Plant J.*, vol. 7 No. 4, pp. 687-701, Apr. 1, 1995.

Pain, B et al., Chicken Embryonic Stem Cells and Transgenic Strategies, *Cell Tissues Organs*, vol. 165, pp. 212-219, 1999.
Park, H., COUP-TF Plays a Dual ROle in the Regulation of the Ovalbumin Gene, *Biochemistry*, vol. 39, pp. 8537-8545, Jan. 1, 2000.
Phan et al., Structural Basis for the Substrate Specificity of Tobacco Etch Virus Protease, *Journal of Biological Chemistry*, vol. 277 No. 52, pp. 50564-50572, Dec. 27, 2002.
Platon, D., A Shortage of Monoclonal Antibody Manufacturing Capacity.
Prudhomme, M. et al., Diversity of Tn4001 transposition products: the flanking IS256 elements can form tandem dimers and IS circles, *J Bacteriol*, vol. 184(2), pp. 433-443, Jan. 1, 2002.
Qiu, Y., Spatiotemporal Expression Patterns of Chicken Ovalbumin Upstream Promoter-Transcription Factors in the Developing Mouse Central Nervous System: Evidence for a ROle in Segmental Patterning of the Diencephalon, *Proc. Natl. Acad. Sci.*, vol. 91, pp. 4451-4455, Jan. 1, 1994.
Richardson, P.D., Gene Repair and Transposon-Mediated Gene Therapy, *Stem Cells*, vol. 20, pp. 112-115, 2002.
Sakai, J. et al., Two classes of Tn10 transposase mutants that suppress mutations in the Tn10 terminal inverted repeat, *Genetics*, vol. 144(3), pp. 861-870, Nov. 1, 1996.
Sarmasik, Aliye et al., Transgenic live-bearing fish and crustaceans produced by transforming immature gonads with replication-defective pantropic retroviral vectors, *Marine Biotechnology*, vol. 3 (5), pp. 470-477, 2001.
Sasakawa, C. et al., Control of transposon Tn5 transposition in *Escherichia coli Prod Natl Acad Sci USA*, pp. 79(23), 7450-7454, Dec. 1, 1982.
Schlenstedt et al., Structural Requirements for Transport of PreprocecropinA and Related Presecretory Proteins into Mammalian Microsomes, *The Journal of Biological Chemistry*, vol. 267(34), pp. 24328-24332, Dec. 5, 1992.
Schneider et al., An Epitope Tagged Mammalian / Prokaryotic Expression Vector with Positive Selection of Cloned Inserts, *Gene: An International Journal on Genes and Genomes*, vol. 197, pp. 337-341, 1997.
Schultz et al., Translation Initiation of IS50R Read-through Transcripts, *J. Mol. Biol.*, vol. 221, pp. 65-80, 1991.
Seal et al., Mutational Studies Reveal a Complex Set of Positive and Negative Control Elements Within the Chicken Vitellogenin II Promoter, *Mol. Cell Biol.*, vol. 11 No. 5, pp. 2704-2717, May 1, 1991.
Sekine, Y. et al., Identification of the site of translational frameshifting required for production of the transposase encoded by insertion sequence IS 1, *Mol Gen Genet*, vol. 235(2-3), pp. 317-324, Nov. 1, 1992.
Sekine, Y. et al, DNA Sequences required for translational frameshifting in production of the transposase encoded by IS1, *Mol Gen Genet*, vol. 235(2-3), pp. 325-332, Nov. 1, 1992.
Sharma et al., Pancreatic Islet Expression of the Homeobox Factor STF-1 Relies on and E-box Motif That Binds USF, *Journal of Biological Chemistry*, vol. 271 No. 4, pp. 2294-2299, Jan. 26, 1996.
Sherman et al., Transposition of the *Drosophila* Element Mariner into the Chicken Germ Line, *Nature Biotechnology*, vol. 16, pp. 1050-1053, Nov. 1, 1998.
Sherratt, D., Tn3 and Related Transposable Elements: Site-Specific Recombination and Transposition, *Mobile DNA*, pp. 163-184, Jan. 1, 1989.
Simons, R.W. et al., Translational Control of IS10 transposition, *Cell*, vol. 34(2), pp. 683-691, Sep. 1, 1983.
Slowinski et al., Pattern of Prepo-Endothelin-1 Expression Revealed by Reporter-Gene Activity in Kidneys of Erythropoietin-Overexpressing Mice, *Clinical Science.*, vol. 103 (48), pp. 445-475, Clinical Science.
Vilen et al., Construction of Gene-targeting Vectors: a Rapid Mu in vitro DNA Transposition-based Strategy Generating Null, Potentially Hypomorphic, and Conditional Alleles, *Transgenic Research*, vol. 10, pp. 69-80, Jan. 1, 2001.
Von Specht, M., Expression eines rekombinanten humanen Proteins in vitro und in vivo in Eileiterzellen des Huhnes, am Beispiel von humanem Erythropoeitin, hrEPO (English Translation Provided), *Dissertation*, pp. 49-68, 2002.
Wallace et al., *Biology the Science of Life*, vol. 2, p. 235, 1986.

Wang, A. et al., Activation of silent genes by transposons Tn5 and Tn10, *Genetics*, vol. 120(4), pp. 875-885, Dec. 1, 1988.
Xanthopoulos et al., The structure of the gene for cecropin B, an antibacterial immune protein from *Hyalophora cecropia, European Journal of Biochemistry*, vol. 172, pp. 371-376, 1988.
Zagoraiou, L. In vivo Transposition of Minos, a *Drosophila* Mobile Element, in Mammalian Tissues, *Proc. Natl. Acad. Sci. USA*, vol. 98 (20), pp. 11474-11478, Jan. 1, 2001.
Zhukova et al., Expression of the Human Insulin Gene in the Gastric G Cells of Transgenic Mice, *Transgenic Research*, vol. 10, pp. 329-341, Jan. 1, 2001.
"Gene Therapy a Suspect in Leukemia-Like Disease", Science, News of the Week, Oct. 4, 2002, vol. 298, 34-35.
U.S. Appl. No. 10/609,019, "Notice of Allowance", Jan. 9, 2009.
U.S. Appl. No. 10/609,019, "Office Action", May 4, 2007.
U.S. Appl. No. 10/609,019, "Office Action", Nov. 7, 2006.
U.S. Appl. No. 10/609,019, "Office Action", Jun. 26, 2006.
U.S. Appl. No. 10/609,019, "Office Action", Oct. 17, 2007.
U.S. Appl. No. 10/609,019, "Office Action", Feb. 12, 2008.
U.S. Appl. No. 10/609,019, "Office Action", Dec. 27, 2005.
U.S. Appl. No. 10/746,149, "Office Action", Feb. 3, 2009.
U.S. Appl. No. 10/746,149, "Office Action", Feb. 8, 2008.
U.S. Appl. No. 10/746,149, "Office Action", Oct. 18, 2007.
U.S. Appl. No. 10/746,149, "Office Action", Feb. 28, 2007.
U.S. Appl. No. 10/746,149, "Office Action", Aug. 20, 2008.
U.S. Appl. No. 10/746,149, "Office Action", Aug. 9, 2006.
U.S. Appl. No. 11/981,574, "Notice of Allowance", Aug. 10, 2009.
U.S. Appl. No. 11/981,574, "Office Action", Jun. 24, 2009.
U.S. Appl. No. 11/981,574, "Office Action", Jan. 7, 2009.
U.S. Appl. No. 11/981,629, "Office Action", Dec. 27, 2010.
U.S. Appl. No. 11/981,629, "Office Action", Dec. 10, 2009.
U.S. Appl. No. 11/981,629, "Office Action", Feb. 5, 2009.
Alexeyev et al., "Mini-Tn10 transposon derivatives for insertion mutagenesis and gene delivery into the chromosome of Gram-negative bacteria", Gene, vol. 160, No. 1, Jul. 4, 1995, 59-62.
AU 2003261096, "Examiners Second Report dated Jun 6, 2008".
AU 2003261096, "Notice of Acceptance".
CA 2,490,693, "Notice of Allowance" Mar. 24, 2011.
CA 2,490,693, "Office Action" Oct. 5, 2009.
CA 2,490,693, "Office Action", May 4, 2010.
CA 2,490,693, "Office Action", Dec. 30, 2010.
EP 037621729, "Communication Under Rule 71(3) EPC", Nov. 11, 2008.
EP 037621729, "Fifth Office Action", Feb. 26, 2008.
EP 037621729, "Fourth Office Action", Oct. 10, 2007.
EP 037621729, "Supplementary Search Report", Feb. 15, 2006.
EP 03800225.9, "Decision to Grant", Aug. 19, 2008.
EP 03800225.9, "First Office Action", Jun. 14, 2007.
EP 03800225.9, "Second Office Action", Nov. 7, 2007.
EP 03800225.9, "Supplemental Search Report", May 26, 2006.
Fisher et al., "Induction of Terminal Differentiation in Cancer Cells as a Therapeutic Modality for Suppressing Tumor Growth: Studies Employing Human Melanoma", Anticancer Research, 1988, vol. 8 (5B), 1057.
Geyer et al., "Protecting against promiscuity: The regulatory role of insulators", Cellular and Molecular Life Sciences, XP002573586, 2002, vol. 59, No. 12, pp. 2112-2127.
Heilig et al., "NCBI Accession No. V00437-Gallus Gallus Fragment of Ovalbumin Gene Coding for the First Leader Exon.", 1997.
Heilig et al., "The Ovalbumin Gene Family, the 5' End Region of the X and Y Genes", J. Mol. Bio, 1982, vol. 156, No. 1, pp. 1-19.
Herrero et al., "Transposon Vectors Contining Non-Antiobiotic Resistance Selection Markers for Cloning and Stable Chromosomal Insertion of Foreign Genes in Gram-Negative Bacteria", Journal of Bacteriology, Washington, DC, vol. 172, No. 11, Nov. 1, 1990, 6557-6567.
Houdebine, "The Methods to Generate Animals and to Control Transgene Expression", J. Biotech, 2006, 98:146-147.
Jeltsch et al., "The Complete Nucleotide Sequence of the Chicken Ovotransferrin mRNA", Eur.J. Biochem, 1982, 122, 291-295.
JP 2004-518011, "Final Decision of Rejection", Mar. 2, 2010.
JP 2004-518011, "First Office Action", Sep. 8, 2009.
JP 2004567449, "First Office Action", Dec. 1, 2009.

Largaespada, "Generating and manipulating transgenic animals using transposable elements", Reproductive Biology and Endrocrinology XX, XX, XP021009352, 2003, vol. 1, No. 1, p. 80.

Lillico et al., "Transgenic Chickens as Bioreactors for Protein-Based Drugs", Drug Discovery Today, Feb. 2005, vol. 10, No. 3, pp. 191-196.

Maksimenko, "Insulators of Higher Eukaryotes: Properties Mechanisms of Action, and Role in Transcriptional Regulation", Russian Journal of Genetics, XP002573587, 2006, vol. 42, No. 8, pp. 845-857.

Maksimenko, "Insulators of higher Eukaryotes: properties, mechanisms of action, and role in transcriptional regulation", GENETIKA (Aug. 2006),XP002573587, 2006, vol. 42, No. 8, pp. 1029-1044.

Mozdziak et al., "Status of Transgenic Chicken Models for Developmental Biology", Developmental Dynamics, 2004, 229:414-421.

PCT/US03/041335, "International Search Report", Nov. 3, 2004.

PCT/US03/41261, "International Search Report", Nov. 3, 2004.

PCT/US04/43092, "International Search Report and Written Opinion", May 11, 2006.

PCT/US2003/020389, "International Search Report", Apr. 2, 2004.

PCT/US2009/058494, PCT International Search Report, mailed Apr. 14, 2010.

PCT/US2009/058497, PCT International Search Report, mailed Apr. 14, 2010.

PCT/US2009/058498, International Search Report and Written Opinion mailed Oct. 6, 2010.

Pieper, et al., "Restoration of Vascular Endothelial Function in Diabetes", Diabetes Res. Clin. Pract. Suppl., 1996, S157-S162.

Sang et al., "Prospects for Transgenesis in the Chick", Mech. Dev., 2004, 121(9): 1179-86.

Telmer et al., "Epitope Tagging Genomic DNA Using a CD-Tagging Tn10 Minitransposon", Bio Techniques 2002, vol. 32, No. 2; 422-430.

\* cited by examiner

FIGURE 4

| IS | Tet_i Pro | Ovgen | Pro | Ovotrans | Pro | Ovomucin | IS |

```
                        SEQUENCE LISTING

<160> NUMBER OF SEQ ID NOS: 50

<210> SEQ ID NO 1
<211> LENGTH: 54
<212> TYPE: DNA
<213> ORGANISM: Artificial Sequence
<220> FEATURE:
<223> OTHER INFORMATION: Signal sequence for human tumor necrosis factor

<400> SEQUENCE: 1
atgctgggca tctggaccct cctacctctg gttcttacgt ctgttgctag atta            54

<210> SEQ ID NO 2
<211> LENGTH: 15
<212> TYPE: DNA
<213> ORGANISM: Artificial Sequence
<220> FEATURE:
<223> OTHER INFORMATION: Synthetic cecropin B pro sequence

<400> SEQUENCE: 2
gcgccagagc cgaaa                                                      15

<210> SEQ ID NO 3
<211> LENGTH: 30
<212> TYPE: DNA
<213> ORGANISM: Artificial Sequence
<220> FEATURE:
<223> OTHER INFORMATION: Synthetic cecropin B pro sequence

<400> SEQUENCE: 3
gcgccagagc cgaaatggaa agtcttcaag                                      30
```

```
<210> SEQ ID NO 4
<211> LENGTH: 78
<212> TYPE: DNA
<213> ORGANISM: Artificial Sequence
<220> FEATURE:
<223> OTHER INFORMATION: Synthetic cecropin B prepro sequence

<400> SEQUENCE: 4
aatttctcaa ggatattttt cttcgtgttc gctttggttc tggctttgtc aacagtttcg    60
gctgcgccag agccgaaa                                                  78

<210> SEQ ID NO 5
<211> LENGTH: 93
<212> TYPE: DNA
<213> ORGANISM: Artificial Sequence
<220> FEATURE:
<223> OTHER INFORMATION: Synthetic cecropin B prepro sequence

<400> SEQUENCE: 5
aatttctcaa ggatattttt cttcgtgttc gctttggttc tggctttgtc aacagtttcg    60
gctgcgccag agccgaaatg gaaagtcttc aag                                 93

<210> SEQ ID NO 6
<211> LENGTH: 7315
<212> TYPE: DNA
<213> ORGANISM: Artificial Sequence
<220> FEATURE:
<223> OTHER INFORMATION: Synthetic

<400> SEQUENCE: 6
ctgacgcgcc ctgtagcggc gcattaagcg cggcgggtgt ggtggttacg cgcagcgtga    60
ccgctacact tgccagcgcc ctagcgcccg ctcctttcgc tttcttccct tcctttctcg   120
ccacgttcgc cggcatcaga ttggctattg gccattgcat acgttgtatc catatcataa   180
tatgtacatt tatattggct catgtccaac attaccgcca tgttgacatt gattattgac   240
tagttattaa tagtaatcaa ttacggggtc attagttcat agcccatata tggagttccg   300
cgttacataa cttacggtaa atggcccgcc tggctgaccg cccaacgacc cccgcccatt   360
gacgtcaata atgacgtatg ttcccatagt aacgccaata gggactttcc attgacgtca   420
atgggtggag tatttacggt aaactgccca cttggcagta catcaagtgt atcatatgcc   480
aagtacgccc cctattgacg tcaatgacgg taaatggccc gcctggcatt atgcccagta   540
catgacctta tgggactttc ctacttggca gtacatctac gtattagtca tcgctattac   600
catggtgatg cggttttggc agtacatcaa tgggcgtgga tagcggtttg actcacgggg   660
atttccaagt ctccacccca ttgacgtcaa tgggagtttg ttttggcacc aaaatcaacg   720
ggactttcca aaatgtcgta acaactccgc cccattgacg caaatgggcg gtaggcgtgt   780
acggtgggag gtctatataa gcagagctcg tttagtgaac cgtcagatcg cctggagacg   840
ccatccacgc tgttttgacc tccatagaag acaccgggac cgatccagcc tccgcggccg   900
ggaacggtgc attggaacgc ggattccccg tgccaagagt gacgtaagta ccgcctatag   960
actctatagg cacacccctt tggctcttat gcatgctata ctgtttttgg cttggggcct  1020
atacaccccc gcttccttat gctataggtg atggtatagc ttagcctata ggtgtgggtt  1080
attgaccatt attgaccact cccctattgg tgacgatact ttccattact aatccataac  1140
atggctcttt gccacaacta tctctattgg ctatatgcca atactctgtc cttcagagac  1200
tgacacggac tctgtatttt tacaggatgg ggtcccattt attatttaca aattcacata  1260
tacaacaacg ccgtccccg tgcccgcagt ttttattaaa catagcgtgg gatctccacg  1320
```

```
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtcgga ccatgtgcga actcgatatt   1800
ttacacgact ctctttacca attctgcccc gaattacact taaaacgact caacagctta   1860
acgttggctt gccacgcatt acttgactgt aaaactctca ctcttaccga acttggccgt   1920
aacctgccaa ccaaagcgag aacaaaacat aacatcaaac gaatcgaccg attgttaggt   1980
aatcgtcacc tccacaaaga gcgactcgct gtataccgtt ggcatgctag ctttatctgt   2040
tcgggcaata cgatgcccat tgtacttgtt gactggtctg atattcgtga gcaaaaacga   2100
cttatggtat tgcgagcttc agtcgcacta cacggtcgtt ctgttactct ttatgagaaa   2160
gcgttcccgc tttcagagca atgttcaaag aaagctcatg accaatttct agccgacctt   2220
gcgagcattc taccgagtaa caccacaccg ctcattgtca gtgatgctgg ctttaaagtg   2280
ccatggtata aatccgttga aagctgggt tggtactggt taagtcgagt aagaggaaaa   2340
gtacaatatg cagacctagg agcggaaaac tggaaaccta tcagcaactt acatgatatg   2400
tcatctagtc actcaaagac tttaggctat aagaggctga ctaaaagcaa tccaatctca   2460
tgccaaattc tattgtataa atctcgctct aaaggccgaa aaaatcagcg ctcgacacgg   2520
actcattgtc accacccgtc acctaaaatc tactcagcgt cggcaaagga gccatgggtt   2580
ctagcaacta acttacctgt tgaaattcga acacccaaac aacttgttaa tatctattcg   2640
aagcgaatgc agattgaaga aaccttccga gacttgaaaa gtcctgccta cggactaggc   2700
ctacgccata gccgaacgag cagctcagag cgttttgata tcatgctgct aatcgccctg   2760
atgcttcaac taacatgttg gcttgcgggc gttcatgctc agaaacaagg ttgggacaag   2820
cacttccagg ctaacacagt cagaaatcga acgtactct caacagttcg cttaggcatg   2880
gaagttttgc ggcattctgg ctacacaata acaagggaag acttactcgt ggctgcaacc   2940
ctactagctc aaaatttatt cacacatggt tacgctttgg ggaaattatg aggggatcgc   3000
tctagagcga tccgggatct cgggaaaagc gttggtgacc aaaggtgcct tttatcatca   3060
ctttaaaaat aaaaaacaat tactcagtgc ctgttataag cagcaattaa ttatgattga   3120
tgcctacatc acaacaaaaa ctgatttaac aaatggttgg tctgccttag aaagtatatt   3180
tgaacattat cttgattata ttattgataa taataaaaac cttatcccta tccaagaagt   3240
gatgcctatc attggttgga atgaacttga aaaaattag ccttgaatac attactggta   3300
aggtaaacgc cattgtcagc aaattgatcc aagagaacca acttaaagct ttcctgacgg   3360
aatgttaatt ctcgttgacc ctgagcactg atgaatcccc taatgatttt ggtaaaaatc   3420
attaagttaa ggtggataca catcttgtca tatgatcccg gtaatgtgag ttagctcact   3480
cattaggcac cccaggcttt acactttatg cttccggctc gtatgttgtg tggaattgtg   3540
agcggataac aatttcacac aggaaacagc tatgaccatg attacgccaa gcgcgcaatt   3600
aaccctcact aaagggaaca aaagctggag ctccaccgcg gtggcggccg ctctagaact   3660
agtggatccc ccgggctgca ggaattcgat atcaagctta tcgataccgc tgacctcgag   3720
```

```
gggggggcccg gtacccaatt cgccctatag tgagtcgtat tacgcgcgct cactggccgt    3780
cgttttacaa cgtcgtgact gggaaaaccc tggcgttacc caacttaatc gccttgcagc    3840
acatcccct  ttcgccagct ggcgtaatag cgaagaggcc cgcaccgatc gcccttccca    3900
acagttgcgc agcctgaatg gcgaatggaa attgtaagcg ttaatatttt gttaaaattc    3960
gcgttaaatt tttgttaaat cagctcattt tttaaccaat aggccgaaat cggcaaaatc    4020
ccttataaat caaaagaata daccgagata gggttgagtg ttgttccagt ttggaacaag    4080
agtccactat taagaacgt  ggactccaac gtcaaagggc gaaaaaccgt ctatcagggc    4140
gatggcccac tactccggga tcatatgaca agatgtgtat ccaccttaac ttaatgattt    4200
ttaccaaaat cattagggga ttcatcagtg ctcagggtca acgagaatta acattccgtc    4260
aggaaagctt atgatgatga tgtgcttaaa aacttactca atggctggtt atgcatatcg    4320
caatacatgc gaaaaaccta aaagagcttg ccgataaaaa aggccaattt attgctattt    4380
accgcggctt tttattgagc ttgaaagata aataaaatag ataggtttta tttgaagcta    4440
aatcttcttt atcgtaaaaa atgccctctt gggttatcaa gagggtcatt atatttcgcg    4500
gaataacatt atttggtgac gaaataacta agcacttgtc tcctgtttac tcccctgagc    4560
ttgaggggtt aacatgaagg tcatcgatag caggataata atacagtaaa acgctaaacc    4620
aataatccaa atccagccat cccaaattgg tagtgaatga ttataaataa cagcaaacag    4680
taatgggcca ataacaccgg ttgcattggt aaggctcacc aataatccct gtaaagcacc    4740
ttgctgatga ctctttgttt ggatagacat cactccctgt aatgcaggta aagcgatccc    4800
accaccagcc aataaaatta aaacagggaa aactaaccaa ccttcagata taaacgctaa    4860
aaaggcaaat gcactactat ctgcaataaa tccgagcagt actgccgttt tttcgcccat    4920
ttagtggcta ttcttcctgc cacaaaggct tggaatactg agtgtaaaag accaagaccc    4980
gtaatgaaaa gccaaccatc atgctattca tcatcacgat ttctgtaata gcaccacacc    5040
gtgctggatt ggctatcaat gcgctgaaat aataatcaac aaatggcatc gttaaataag    5100
tgatgtatac cgatcagctt ttgttcccct tagtgagggt taattgcgcg cttggcgtaa    5160
tcatggtcat agctgtttcc tgtgtgaaat tgttatccgc tcacaattcc acacaacata    5220
cgagccggaa gcataaagtg taaagcctgg ggtgcctaat gagtgagcta actcacatta    5280
attgcgttgc gctcactgcc cgctttccag tcgggaaacc tgtcgtgcca gctgcattaa    5340
tgaatcggcc aacgcgcggg gagaggcggt ttgcgtattg ggcgctcttc cgcttcctcg    5400
ctcactgact cgctgcgctc ggtcgttcgg ctgcggcgag cggtatcagc tcactcaaag    5460
gcggtaatac ggttatccac agaatcaggg gataacgcag gaaagaacat gtgagcaaaa    5520
ggccagcaaa aggccaggaa ccgtaaaaag gccgcgttgc tggcgttttt ccataggctc    5580
cgcccccctg acgagcatca caaaaatcga cgctcaagtc agaggtggcg aaacccgaca    5640
ggactataaa gataccaggc gtttccccct ggaagctccc tcgtgcgctc tcctgttccg    5700
accctgccgc ttaccggata cctgtccgcc tttctccctt cgggaagcgt ggcgctttct    5760
catagctcac gctgtaggta tctcagttcg gtgtaggtcg ttcgctccaa gctgggctgt    5820
gtgcacgaac ccccgttca  gcccgaccgc tgcgccttat ccggtaacta tcgtcttgag    5880
tccaacccgg taagacacga cttatcgcca ctggcagcag ccactggtaa caggattagc    5940
agagcgaggt atgtaggcgg tgctacagag ttcttgaagt ggtggcctaa ctacggctac    6000
actagaagga cagtatttgg tatctgcgct ctgctgaagc cagttacctt cggaaaaaga    6060
gttggtagct cttgatccgg caaacaaacc accgctggta gcggtggttt ttttgtttgc    6120
```

```
aagcagcaga ttacgcgcag aaaaaaagga tctcaagaag atcctttgat cttttctacg    6180
gggtctgacg ctcagtggaa cgaaaactca cgttaaggga ttttggtcat gagattatca    6240
aaaaggatct tcacctagat ccttttaaat taaaaatgaa gttttaaatc aatctaaagt    6300
atatatgagt aaacttggtc tgacagttac caatgcttaa tcagtgaggc acctatctca    6360
gcgatctgtc tatttcgttc atccatagtt gcctgactcc ccgtcgtgta gataactacg    6420
atacgggagg gcttaccatc tggccccagt gctgcaatga taccgcgaga cccacgctca    6480
ccggctccag atttatcagc aataaaccag ccagccggaa gggccgagcg cagaagtggt    6540
cctgcaactt tatccgcctc catccagtct attaattgtt gccgggaagc tagagtaagt    6600
agttcgccag ttaatagttt gcgcaacgtt gttgccattg ctacaggcat cgtggtgtca    6660
cgctcgtcgt ttggtatggc ttcattcagc tccggttccc aacgatcaag gcgagttaca    6720
tgatccccca tgttgtgcaa aaaagcggtt agctccttcg gtcctccgat cgttgtcaga    6780
agtaagttgg ccgcagtgtt atcactcatg gttatgcag cactgcataa ttctcttact    6840
gtcatgccat ccgtaagatg cttttctgtg actggtgagt actcaaccaa gtcattctga    6900
gaatagtgta tgcggcgacc gagttgctct tgcccggcgt caatacggga taataccgcg    6960
ccacatagca gaactttaaa agtgctcatc attggaaaac gttcttcggg gcgaaaactc    7020
tcaaggatct taccgctgtt gagatccagt tcgatgtaac ccactcgtgc acccaactga    7080
tcttcagcat cttttacttt caccagcgtt tctgggtgag caaaaacagg aaggcaaaat    7140
gccgcaaaaa agggaataag ggcgacacgg aaatgttgaa tactcatact cttccttttt    7200
caatattatt gaagcattta tcagggttat tgtctcatga gcggatacat atttgaatgt    7260
atttagaaaa ataaacaaat aggggttccg cgcacatttc cccgaaaagt gccac         7315

<210> SEQ ID NO 7
<211> LENGTH: 7689
<212> TYPE: DNA
<213> ORGANISM: Artificial Sequence
<220> FEATURE:
<223> OTHER INFORMATION: Synthetic

<400> SEQUENCE: 7
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggcatcaga ttggctattg gccattgcat acgttgtatc catatcataa     180
tatgtacatt tatattggct catgtccaac attaccgcca tgttgacatt gattattgac     240
tagttattaa tagtaatcaa ttacggggtc attagttcat agcccatata tggagttccg     300
cgttacataa cttacggtaa atggcccgcc tggctgaccg cccaacgacc cccgcccatt     360
gacgtcaata atgacgtatg ttcccatagt aacgccaata gggactttcc attgacgtca     420
atgggtggag tatttacggt aaactgccca cttggcagta catcaagtgt atcatatgcc     480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
```

```
ggaacggtgc attggaacgc ggattccccg tgccaagagt gacgtaagta ccgcctatag   960
actctatagg cacaccctt tggctcttat gcatgctata ctgttttggg cttggggcct  1020
atacacccc gcttccttat gctataggtg atggtatagc ttagcctata ggtgtgggtt  1080
attgaccatt attgaccact cccctattgg tgacgatact ttccattact aatccataac  1140
atggctcttt gccacaacta tctctattgg ctatatgcca atactctgtc cttcagagac  1200
tgacacggac tctgtatttt tacaggatgg ggtcccattt attatttaca aattcacata  1260
tacaacaacg ccgtcccccg tgcccgcagt ttttattaaa catagcgtgg gatctccacg  1320
cgaatctcgg gtacgtgttc cggacatggg ctcttctccg gtagcggcgg agcttccaca  1380
tccgagccct ggtcccatgc ctccagcggc tcatggtcgc tcggcagctc cttgctccta  1440
acagtggagg ccagacttag gcacagcaca atgcccacca ccaccagtgt gccgcacaag  1500
gccgtggcgg tagggtatgt gtctgaaaat gagcgtggag attgggctcg cacggctgac  1560
gcagatggaa gacttaaggc agcggcagaa gaagatgcag gcagctgagt tgttgtattc  1620
tgataagagt cagaggtaac tcccgttgcg gtgctgttaa cggtggaggg cagtgtagtc  1680
tgagcagtac tcgttgctgc cgcgcgcgcc accagacata atagctgaca gactaacaga  1740
ctgttccttt ccatgggtct tttctgcagt caccgtcgga ccatgtgtga acttgatatt  1800
ttacatgatt ctctttacca attctgcccc gaattacact taaaacgact caacagctta  1860
acgttggctt gccacgcatt acttgactgt aaaactctca ctcttaccga acttggccgt  1920
aacctgccaa ccaaagcgag aacaaaacat aacatcaaac gaatcgaccg attgttaggt  1980
aatcgtcacc tccacaaaga gcgactcgct gtataccgtt ggcatgctag ctttatctgt  2040
tcgggaatac gatgcccatt gtacttgttg actggtctga tattcgtgag caaaaacgac  2100
ttatggtatt gcgagcttca gtcgcactac acggtcgttc tgttactctt tatgagaaag  2160
cgttcccgct ttcagagcaa tgttcaaaga aagctcatga ccaatttcta gccgaccttg  2220
cgagcattct accgagtaac accacaccgc tcattgtcag tgatgctggc tttaaagtgc  2280
catggtataa atccgttgag aagctgggtt ggtactggtt aagtcgagta agaggaaaag  2340
tacaatatgc agacctagga gcggaaaact ggaaacctat cagcaactta catgatatgt  2400
catctagtca ctcaaaagact ttaggctata agaggctgac taaaagcaat ccaatctcat  2460
gccaaattct attgtataaa tctcgctcta aaggccgaaa aaatcagcgc tcgacacgga  2520
ctcattgtca ccacccgtca cctaaaatct actcagcgtc ggcaaaggag ccatgggttc  2580
tagcaactaa cttacctgtt gaaattcgaa cacccaaaca acttgttaat atctattcga  2640
agcgaatgca gattgaagaa accttccgag acttgaaaag tcctgcctac ggactaggcc  2700
tacgccatag ccgaacgagc agctcagagc gttttgatat catgctgcta atcgccctga  2760
tgcttcaact aacatgttgg cttgcgggcg ttcatgctca gaaacaaggt tgggacaagc  2820
acttccaggc taacacagtc agaaatcgaa acgtactctc aacagttcgc ttaggcatgg  2880
aagttttgcg gcattctggc tacacaataa caagggaaga cttactcgtg gctgcaaccc  2940
tactagctca aaatttattc acacatggtt acgctttggg gaaattatga taatgatcca  3000
gatcacttct ggctaataaa agatcagagc tctagagatc tgtgtgttgg ttttttgtgg  3060
atctgctgtg ccttctagtt gccagccatc tgttgtttgc ccctcccccg tgccttcctt  3120
gaccctggaa ggtgccactc ccactgtcct ttcctaataa aatgaggaaa ttgcatcgca  3180
ttgtctgagt aggtgtcatt ctattctggg ggtgggggtg gggcagcaca gcaagggga   3240
ggattgggaa gacaatagca ggcatgctgg ggatgcggtg ggctctatgg gtacctctct  3300
```

```
ctctctctct ctctctctct ctctctctct ctctcggtac ctctctctct ctctctctct    3360
ctctctctct ctctctctct cggtaccagg tgctgaagaa ttgacccggt gaccaaaggt    3420 gcctttatc atcactttaa aaataaaaaa caattactca gtgcctgtta taagcagcaa     3480
ttaattatga ttgatgccta catcacaaca aaaactgatt taacaaatgg ttggtctgcc    3540
ttagaaagta tatttgaaca ttatcttgat tatattattg ataataataa aaaccttatc   3600
cctatccaag aagtgatgcc tatcattggt tggaatgaac ttgaaaaaaa ttagccttga    3660
atacattact ggtaaggtaa acgccattgt cagcaaattg atccaagaga accaacttaa    3720
agctttcctg acggaatgtt aattctcgtt gaccctgagc actgatgaat cccctaatga    3780
ttttggtaaa aatcattaag ttaaggtgga tacacatctt gtcatatgat cccggtaatg    3840
tgagttagct cactcattag gcaccccagg ctttacactt tatgcttccg gctcgtatgt    3900
tgtgtggaat tgtgagcgga taacaatttc acacaggaaa cagctatgac catgattacg    3960
ccaagcgcgc aattaaccct cactaaaggg aacaaaagct ggagctccac cgcggtggcg    4020
gccgctctag aactagtgga tcccccgggc tgcaggaatt cgatatcaag cttatcgata    4080
ccgctgacct cgagggggggg cccggtaccc aattcgccct atagtgagtc gtattacgcg    4140
cgctcactgg ccgtcgtttt acaacgtcgt gactgggaaa accctggcgt tacccaactt    4200
aatcgccttg cagcacatcc ccctttcgcc agctggcgta atagcgaaga ggcccgcacc    4260
gatcgccctt cccaacagtt gcgcagcctg aatggcgaat ggaaattgta agcgttaata    4320
ttttgttaaa attcgcgtta aattttttgtt aaatcagctc attttttaac caataggccg    4380
aaatcggcaa aatcccttat aaatcaaaag aatagaccga tagggttg agtgttgttc      4440 cagtttggaa caagagtcca ctattaaaga acgtggactc caacgtcaaa gggcgaaaaa    4500
ccgtctatca gggcgatggc ccactactcc gggatcatat gacaagatgt gtatccacct    4560
taacttaatg attttttacca aaatcattag gggattcatc agtgctcagg gtcaacgaga    4620
attaacattc cgtcaggaaa gcttatgatg atgatgtgct taaaaactta ctcaatggct    4680
ggttatgcat atcgcaatac atgcgaaaaa cctaaaagag cttgccgata aaaaaggcca    4740
atttattgct atttaccgcg gcttttttatt gagcttgaaa gataaataaa atagataggt    4800
tttatttgaa gctaaatctt ctttatcgta aaaaatgccc tcttgggtta tcaagagggt    4860
cattatattt cgcggaataa catcatttgg tgacgaaata actaagcact tgtctcctgt    4920
ttactcccct gagcttgagg ggttaacatg aaggtcatcg atagcaggat aataatacag    4980
taaaacgcta aaccaataat ccaaatccag ccatcccaaa ttggtagtga atgattataa    5040
ataacagcaa acagtaatgg gccaataaca ccggttgcat tggtaaggct caccaataat    5100
ccctgtaaag caccttgctg atgactcttt gtttggatag acatcactcc ctgtaatgca    5160
ggtaaagcga tcccaccacc agccaataaa attaaaacag ggaaaactaa ccaaccttca    5220
gatataaacg ctaaaaaggc aaatgcacta ctatctgcaa taaatccgag cagtactgcc    5280
gttttttcgc ccatttagtg gctattcttc ctgccacaaa ggcttggaat actgagtgta    5340
aaagaccaag acccgtaatg aaaagccaac catcatgcta ttcatcatca cgatttctgt    5400
aatagcacca caccgtgctg gattggctat caatgcgctg aaataataat caacaaatgg    5460
catcgttaaa taagtgatgt ataccgatca gcttttgttc cctttagtga gggttaattg    5520
cgcgcttggc gtaatcatgg tcatagctgt ttcctgtgtg aaattgttat ccgctcacaa    5580
ttccacacaa catacgagcc ggaagcataa agtgtaaagc ctggggtgcc taatgagtga    5640
gctaactcac attaattgcg ttgcgctcac tgcccgcttt ccagtcggga aacctgtcgt    5700
```

-continued

```
gccagctgca ttaatgaatc ggccaacgcg cggggagagg cggtttgcgt attgggcgct    5760
cttccgcttc ctcgctcact gactcgctgc gctcggtcgt tcggctgcgg cgagcggtat    5820
cagctcactc aaaggcggta atacggttat ccacagaatc aggggataac gcaggaaaga    5880
acatgtgagc aaaaggccag caaaaggcca ggaaccgtaa aaaggccgcg ttgctggcgt    5940
ttttccatag gctccgcccc cctgacgagc atcacaaaaa tcgacgctca agtcagaggt    6000
ggcgaaaccc gacaggacta taaagatacc aggcgtttcc ccctggaagc tccctcgtgc    6060
gctctcctgt tccgaccctg ccgcttaccg gatacctgtc cgcctttctc ccttcgggaa    6120
gcgtggcgct ttctcatagc tcacgctgta ggtatctcag ttcggtgtag gtcgttcgct    6180
ccaagctggg ctgtgtgcac gaaccccccg ttcagcccga ccgctgcgcc ttatccggta    6240
actatcgtct tgagtccaac ccggtaagac acgacttatc gccactggca gcagccactg    6300
gtaacaggat tagcagagcg aggtatgtag gcggtgctac agagttcttg aagtggtggc    6360
ctaactacgg ctacactaga aggacagtat ttggtatctg cgctctgctg aagccagtta    6420
ccttcggaaa aagagttggt agctcttgat ccggcaaaca aaccaccgct ggtagcggtg    6480
gtttttttgt ttgcaagcag cagattacgc gcagaaaaaa aggatctcaa gaagatcctt    6540
tgatcttttc tacggggtct gacgctcagt ggaacgaaaa ctcacgttaa gggattttgg    6600
tcatgagatt atcaaaaagg atcttcacct agatcctttt aaattaaaaa tgaagtttta    6660
aatcaatcta agtatatat gagtaaactt ggtctgacag ttaccaatgc ttaatcagtg    6720
aggcacctat ctcagcgatc tgtctatttc gttcatccat agttgcctga ctccccgtcg    6780
tgtagataac tacgatacgg gagggcttac catctggccc cagtgctgca atgataccgc    6840
gagacccacg ctcaccggct ccagatttat cagcaataaa ccagccagcc ggaagggccg    6900
agcgcagaag tggtcctgca actttatccg cctccatcca gtctattaat tgttgccggg    6960
aagctagagt aagtagttcg ccagttaata gtttgcgcaa cgttgttgcc attgctacag    7020
gcatcgtggt gtcacgctcg tcgtttggta tggcttcatt cagctccggt tcccaacgat    7080
caaggcgagt tacatgatcc cccatgttgt gcaaaaaagc ggttagctcc ttcggtcctc    7140
cgatcgttgt cagaagtaag ttggccgcag tgttatcact catggttatg gcagcactgc    7200
ataattctct tactgtcatg ccatccgtaa gatgcttttc tgtgactggt gagtactcaa    7260
ccaagtcatt ctgagaatag tgtatgcggc gaccgagttg ctcttgcccg gcgtcaatac    7320
gggataatac cgcgccacat agcagaactt taaaagtgct catcattgga aaacgttctt    7380
cggggcgaaa actctcaagg atcttaccgc tgttgagatc cagttcgatg taacccactc    7440
gtgcacccaa ctgatcttca gcatctttta ctttcaccag cgtttctggg tgagcaaaaa    7500
caggaaggca aaatgccgca aaaaagggaa taagggcgac acggaaatgt tgaatactca    7560
tactcttcct ttttcaatat tattgaagca tttatcaggg ttattgtctc atgagcggat    7620
acatatttga atgtatttag aaaaataaac aaataggggt tccgcgcaca tttccccgaa    7680
aagtgccac                                                            7689
```

<210> SEQ ID NO 8
<211> LENGTH: 6
<212> TYPE: DNA
<213> ORGANISM: Artificial Sequence
<220> FEATURE:
<223> OTHER INFORMATION: Modified Kozak sequence

<400> SEQUENCE: 8 accatg    6

```
<210> SEQ ID NO 9
<211> LENGTH: 7
<212> TYPE: DNA
<213> ORGANISM: Artificial Sequence
<220> FEATURE:
<223> OTHER INFORMATION: Kozak sequence

<400> SEQUENCE: 9 accatgg                                                                 7

<210> SEQ ID NO 10

<400> SEQUENCE: 10

000

<210> SEQ ID NO 11
<211> LENGTH: 7
<212> TYPE: DNA
<213> ORGANISM: Artificial Sequence
<220> FEATURE:
<223> OTHER INFORMATION: Kozak sequence

<400> SEQUENCE: 11 aagatgt                                                                 7

<210> SEQ ID NO 12
<211> LENGTH: 7
<212> TYPE: DNA
<213> ORGANISM: Artificial Sequence
<220> FEATURE:
<223> OTHER INFORMATION: Kozak sequence

<400> SEQUENCE: 12 acgatga                                                                 7

<210> SEQ ID NO 13
<211> LENGTH: 7
<212> TYPE: DNA
<213> ORGANISM: Artificial Sequence
<220> FEATURE:
<223> OTHER INFORMATION: Kozak sequence

<400> SEQUENCE: 13 aagatgg                                                                 7

<210> SEQ ID NO 14
<211> LENGTH: 7
<212> TYPE: DNA
<213> ORGANISM: Artificial Sequence
<220> FEATURE:
<223> OTHER INFORMATION: Kozak sequence

<400> SEQUENCE: 14 gacatga                                                                 7

<210> SEQ ID NO 15
<211> LENGTH: 7
<212> TYPE: DNA
<213> ORGANISM: Artificial Sequence
<220> FEATURE:
<223> OTHER INFORMATION: Kozak sequence

<400> SEQUENCE: 15 accatga                                                                 7
```

```
<210> SEQ ID NO 16
<211> LENGTH: 7
<212> TYPE: DNA
<213> ORGANISM: Artificial Sequence
<220> FEATURE:
<223> OTHER INFORMATION: Kozak sequence

<400> SEQUENCE: 16 accatgt                                                               7

<210> SEQ ID NO 17
<211> LENGTH: 315
<212> TYPE: DNA
<213> ORGANISM: Artificial Sequence
<220> FEATURE:
<223> OTHER INFORMATION: Synthetic conalbumin polyA sequence

<400> SEQUENCE: 17
tctgccattg ctgcttcctc tgcccttcct cgtcactctg aatgtggctt cttcgctact     60
gccacagcaa gaaataaaat ctcaacatct aaatgggttt cctgaggttt ttcaagagtc    120
gttaagcaca ttccttcccc agcacccctt gctgcaggcc agtgccaggc accaacttgg    180
ctactgctgc ccatgagaga atccagttca atatttttcc aaagcaaaat ggattacata    240
tgccctagat cctgattaac aggcgtttgt attatctagt gctttcgctt cacccagatt    300
atcccattgc ctccc                                                    315

<210> SEQ ID NO 18
<211> LENGTH: 361
<212> TYPE: DNA
<213> ORGANISM: Artificial Sequence
<220> FEATURE:
<223> OTHER INFORMATION: Synthetic

<400> SEQUENCE: 18
ggcgcctgga tccagatcac ttctggctaa taaaagatca gagctctaga gatctgtgtg     60
ttggtttttt gtggatctgc tgtgccttct agttgccagc catctgttgt ttgcccctcc    120
cccgtgcctt ccttgaccct ggaaggtgcc actcccactg tcctttccta ataaaatgag    180
gaaattgcat cgcattgtct gagtaggtgt cattctattc tggggggtgg ggtggggcag    240
cacagcaagg gggaggattg ggaagacaat agcaggcatg ctgggatgc ggtgggctct     300 atgggtacct ctctctctct ctctctctct ctctctctcg gtacctctct                360
c                                                                   361

<210> SEQ ID NO 19
<211> LENGTH: 350
<212> TYPE: DNA
<213> ORGANISM: Artificial Sequence
<220> FEATURE:
<223> OTHER INFORMATION: Synthetic

<400> SEQUENCE: 19
ggggatcgct ctagagcgat ccgggatctc gggaaaagcg ttggtgacca aggtgccttt     60
ttatcatcac tttaaaaata aaaaacaatt actcagtgcc tgttataagc agcaattaat    120
tatgattgat gcctacatca caacaaaaac tgatttaaca aatggttggt ctgccttaga    180
aagtatattt gaacattatc ttgattatat tattgataat aataaaaacc ttatccctat    240
ccaagaagtg atgcctatca ttggttggaa tgaacttgaa aaaaattagc cttgaataca    300
ttactggtaa ggtaaacgcc attgtcagca aattgatcca agagaaccaa                350
```

<210> SEQ ID NO 20
<211> LENGTH: 908
<212> TYPE: DNA
<213> ORGANISM: Artificial Sequence
<220> FEATURE:
<223> OTHER INFORMATION: Synthetic

<400> SEQUENCE: 20

```
tgaatgtgtt cttgtgttat caatataaat cacagttagt gatgaagttg gctgcaagcc      60
tgcatcagtt cagctacttg gctgcatttt gtatttggtt ctgtaggaaa tgcaaaaggt     120
tctaggctga cctgcacttc tatccctctt gccttactgc tgagaatctc tgcaggtttt     180
aattgttcac attttgctcc catttacttt ggaagataaa atatttacag aatgcttatg     240
aaacctttgt tcatttaaaa atattcctgg tcagcgtgac cggagctgaa agaacacatt     300
gatcccgtga tttcaataaa tacatatgtt ccatatattg tttctcagta gcctcttaaa     360
tcatgtgcgt tggtgcacat atgaatacat gaatagcaaa ggtttatctg gattacgctc     420
tggcctgcag gaatggccat aaaccaaagc tgagggaaga gggagagtat agtcaatgta     480
gattatactg attgctgatt gggttattat cagctagata acaacttggg tcaggtgcca     540
ggtcaacata acctgggcaa aaccagtctc atctgtggca ggaccatgta ccagcagcca     600
gccgtgaccc aatctaggaa agcaagtagc acatcaattt taaatttatt gtaaatgccg     660
tagtagaagt gttttactgt gatacattga aacttctggt caatcagaaa aaggtttttt     720
atcagagatg ccaaggtatt atttgatttt ctttattcgc cgtgaagaga atttatgatt     780
gcaaaaagag gagtgtttac ataaactgat aaaaaacttg aggaattcag cagaaaacag     840
ccacgtgttc ctgaacattc ttccataaaa gtctcaccat gcctggcaga gccctattca     900
ccttcgct                                                              908
```

<210> SEQ ID NO 21
<211> LENGTH: 901
<212> TYPE: DNA
<213> ORGANISM: Artificial Sequence
<220> FEATURE:
<223> OTHER INFORMATION: Synthetic chicken ovalbumin promotor fragment

<400> SEQUENCE: 21

```
gaggtcagaa tggtttcttt actgtttgtc aattctatta tttcaataca gaacaatagc      60
ttctataact gaaatatatt tgctattgta tattatgatt gtccctcgaa ccatgaacac     120
tcctccagct gaatttcaca attcctctgt catctgccag gccattaagt tattcatgga     180
agatctttga ggaacactgc aagttcatat cataaacaca tttgaaattg agtattgttt     240
tgcattgtat ggagctatgt tttgctgtat cctcagaaaa aaagtttgtt ataaagcatt     300
cacacccata aaagataga tttaaatatt ccagctatag gaaagaaagt gcgtctgctc     360
ttcactctag tctcagttgg ctccttcaca tgcatgcttc tttatttctc ctattttgtc     420
aagaaaataa taggtcacgt cttgttctca cttatgtcct gcctagcatg gctcagatgc     480
acgttgtaga tacaagaagg atcaaatgaa acagacttct ggtctgttac tacaaccata     540
gtaataagca cactaactaa taattgctaa ttatgttttc catctctaag gttcccacat     600
ttttctgttt tcttaaagat cccattatct ggttgtaact gaagctcaat ggaacatgag     660
caatatttcc cagtcttctc tcccatccaa cagtcctgat ggattagcag acaggcaga     720
aaacacattg ttacccagaa ttaaaaacta atatttgctc tccattcaat ccaaaatgga     780
cctattgaaa ctaaaatcta acccaatccc attaaatgat ttctatggcg tcaaaggtca     840
```

```
aacttctgaa gggaacctgt gggtgggtca caattcaggc tatatattcc ccagggctca    900
g                                                                   901

<210> SEQ ID NO 22
<211> LENGTH: 680
<212> TYPE: DNA
<213> ORGANISM: Artificial Sequence
<220> FEATURE:
<223> OTHER INFORMATION: Synthetic

<400> SEQUENCE: 22
ccgggctgca gaaaaatgcc aggtggacta tgaactcaca tccaaaggag cttgacctga     60
tacctgattt tcttcaaact ggggaaacaa cacaatccca caaacagct cagagagaaa    120 ccatcactga tggctacagc accaaggtat gcaatggcaa tccattcgac attcatctgt    180
gacctgagca aaatgattta tctctccatg aatggttgct ctttccctc atgaaaaggc    240 aatttccaca ctcacaatat gcaacaaaga caaacagaga acaattaatg tgctccttcc    300
taatgtcaaa attgtagtgg caaagaggag aacaaaatct caagttctga gtaggtttta    360
gtgattggat aagaggcttt gacctgtgag ctcacctgga cttcatatcc ttttggataa    420
aaagtgcttt tataactttc aggtctccga gtctttattc atgagactgt tggtttaggg    480
acagacccac aatgaaatgc ctggcatagg aaagggcagc agagccttag ctgaccttt     540 cttgggacaa gcattgtcaa acaatgtgtg acaaaactat ttgtactgct ttgcacagct    600
gtgctgggca gggcaatcca ttgccaccta tcccaggtaa ccttccaact gcaagaagat    660
tgttgcttac tctctctaga                                                680

<210> SEQ ID NO 23
<211> LENGTH: 72
<212> TYPE: DNA
<213> ORGANISM: Artificial Sequence
<220> FEATURE:
<223> OTHER INFORMATION: Synthetic

<400> SEQUENCE: 23
gtggatcaac atacagctag aaagctgtat tgcctttagc actcaagctc aaaagacaac     60
tcagagttca cc                                                         72

<210> SEQ ID NO 24
<211> LENGTH: 62
<212> TYPE: DNA
<213> ORGANISM: Artificial Sequence
<220> FEATURE:
<223> OTHER INFORMATION: Synthetic

<400> SEQUENCE: 24
acatacagct agaaagctgt attgccttta gcactcaagc tcaaaagaca actcagagtt     60
ca                                                                    62

<210> SEQ ID NO 25
<211> LENGTH: 1158
<212> TYPE: DNA
<213> ORGANISM: Artificial Sequence
<220> FEATURE:
<223> OTHER INFORMATION: Synthetic ovalbumin signal sequence

<400> SEQUENCE: 25
atgggctcca tcggcgcagc aagcatggaa tttgtttg atgtattcaa ggagctcaaa      60
gtccaccatg ccaatgagaa catcttctac tgccccattg ccatcatgtc agctctagcc    120
```

-continued

```
atggtatacc tgggtgcaaa agacagcacc aggacacaga taaataaggt tgttcgcttt        180
gataaacttc caggattcgg agacagtatt gaagctcagt gtggcacatc tgtaaacgtt        240
cactcttcac ttagagacat cctcaaccaa atcaccaaac caaatgatgt ttattcgttc        300
agccttgcca gtagacttta tgctgaagag agatacccaa tcctgccaga atacttgcag        360
tgtgtgaagg aactgtatag aggaggcttg gaacctatca actttcaaac agctgcagat        420
caagccagag agctcatcaa ttcctgggta gaaagtcaga caaatggaat tatcagaaat        480
gtccttcagc caagctccgt ggattctcaa actgcaatgg ttctggttaa tgccattgtc        540
ttcaaaggac tgtgggagaa acatttaag gatgaagaca cacaagcaat gcctttcaga        600
gtgactgagc aagaaagcaa acctgtgcag atgatgtacc agattggttt atttagagtg        660
gcatcaatgg cttctgagaa aatgaagatc ctggagcttc catttgccag tgggacaatg        720
agcatgttgg tgctgttgcc tgatgaagtc tcaggccttg agcagcttga gagtataatc        780
aactttgaaa aactgactga atggaccagt tctaatgtta tggaagagag gaagatcaaa        840
gtgtacttac ctcgcatgaa gatggaggaa aaatacaacc tcacatctgt cttaatggct        900
atgggcatta ctgacgtgtt tagctcttca gccaatctgt ctggcatctc ctcagcagag        960
agcctgaaga tatctcaagc tgtccatgca gcacatgcag aaatcaatga agcaggcaga       1020
gaggtggtag ggtcagcaga ggctggagtg gatgctgcaa cgtctctga agaatttagg        1080 gctgaccatc cattcctctt ctgtatcaag cacatcgcaa ccaacgccgt tctcttcttt       1140
ggcagatgtg tttcccct                                                    1158
```

```
<210> SEQ ID NO 26
<211> LENGTH: 53
<212> TYPE: DNA
<213> ORGANISM: Artificial Sequence
<220> FEATURE:
<223> OTHER INFORMATION: Synthetic

<400> SEQUENCE: 26
atgggctcca tcggcgcagc aagcatggaa ttttgttttg atgtattcaa gga              53
```

```
<210> SEQ ID NO 27
<211> LENGTH: 103
<212> TYPE: DNA
<213> ORGANISM: Artificial Sequence
<220> FEATURE:
<223> OTHER INFORMATION: Synthetic

<400> SEQUENCE: 27
atgggctcca tcggcgcagc aagcatggaa ttttgttttg atgtattcaa ggagctcaaa        60
gtccaccatg ccaatgagaa catcttctac tgccccattg cca                        103
```

```
<210> SEQ ID NO 28
<211> LENGTH: 63
<212> TYPE: DNA
<213> ORGANISM: Artificial Sequence
<220> FEATURE:
<223> OTHER INFORMATION: Synthetic vitellogenin targeting sequence

<400> SEQUENCE: 28
atgaggggga tcatactggc attagtgctc acccttgtag gcagccagaa gtttgacatt         60
ggt                                                                     63
```

```
<210> SEQ ID NO 29
<211> LENGTH: 260
<212> TYPE: DNA
```

-continued

<213> ORGANISM: Artificial Sequence
<220> FEATURE:
<223> OTHER INFORMATION: Synthetic

<400> SEQUENCE: 29

```
tttgtgaacc aacacctgtg cggctcacac ctggtggaag ctctctacct agtgtgcggg      60
gaacgaggct tcttctacac acccaagacc cgccgggagg cagaggacct gcaggtgggg     120 caggtgggagc tgggcggggg ccctggtgca ggcagcctgc agcccttggc cctggagggg    180
tccctgcaga agcgtggcat tgtggaacaa tgctgtacca gcatctgctc cctctaccag     240
ctggagaact ctgcaactag                                                260
```

<210> SEQ ID NO 30
<211> LENGTH: 13
<212> TYPE: PRT
<213> ORGANISM: Artificial Sequence
<220> FEATURE:
<223> OTHER INFORMATION: Synthetic

<400> SEQUENCE: 30

```
Lys Tyr Lys Lys Ala Leu Lys Lys Leu Ala Lys Leu Leu
1               5                   10
```

<210> SEQ ID NO 31
<211> LENGTH: 39
<212> TYPE: DNA
<213> ORGANISM: Artificial Sequence
<220> FEATURE:
<223> OTHER INFORMATION: Synthetic

<400> SEQUENCE: 31

```
aaatacaaaa aagcactgaa aaaactggca aaactgctg                            39
```

<210> SEQ ID NO 32
<211> LENGTH: 36
<212> TYPE: PRT
<213> ORGANISM: Artificial Sequence
<220> FEATURE:
<223> OTHER INFORMATION: (Gly Pro Gly Gly) x where x is an integer from
      3-9
<220> FEATURE:
<221> NAME/KEY: MISC_FEATURE
<222> LOCATION: (1)..(36)
<223> OTHER INFORMATION: (Gly Pro Gly Gly) x where x is an integer from
      3-9

<400> SEQUENCE: 32

```
Gly Pro Gly Gly Gly Pro Gly Gly Gly Pro Gly Gly Gly Pro Gly Gly
1               5                   10                  15

Gly Pro Gly Gly Gly Pro Gly Gly Gly Pro Gly Gly Gly Pro Gly Gly
            20                  25                  30

Gly Pro Gly Gly
        35
```

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

```
Gly Pro Gly Gly Gly Pro Gly Gly Gly Pro Gly Gly
1               5                   10
```

```
<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Synthetic

<400> SEQUENCE: 35

Gly Gly Gly Gly Ser Gly Gly Gly Gly Ser Gly Gly Gly Gly Ser Gly
1               5                   10                  15

Gly Gly Gly Ser
            20

<210> SEQ ID NO 36
<211> LENGTH: 5
<212> TYPE: PRT
<213> ORGANISM: Artificial Sequence
<220> FEATURE:
<223> OTHER INFORMATION: Synthetic

<400> SEQUENCE: 36

Pro Ala Asp Asp Ala
1               5

<210> SEQ ID NO 37
<211> LENGTH: 29
<212> TYPE: PRT
<213> ORGANISM: Artificial Sequence
<220> FEATURE:
<223> OTHER INFORMATION: Synthetic

<400> SEQUENCE: 37

Pro Ala Asp Asp Ala Pro Ala Asp Asp Ala Pro Ala Asp Asp Ala Pro
1               5                   10                  15

Ala Asp Asp Ala Pro Ala Asp Asp Ala Pro Ala Asp Asp
            20                  25

<210> SEQ ID NO 38
<211> LENGTH: 16
<212> TYPE: PRT
<213> ORGANISM: Artificial Sequence
<220> FEATURE:
<223> OTHER INFORMATION: Synthetic

<400> SEQUENCE: 38

Ala Thr Thr Cys Ile Leu Lys Gly Ser Cys Gly Trp Ile Gly Leu Leu
1               5                   10                  15

<210> SEQ ID NO 39
<211> LENGTH: 30
<212> TYPE: PRT
<213> ORGANISM: Artificial Sequence
<220> FEATURE:
<223> OTHER INFORMATION: Synthetic

<400> SEQUENCE: 39
```

```
Pro Ala Asp Asp Ala Pro Ala Asp Asp Ala Thr Thr Cys Ile Leu Lys
1               5                   10                  15

Gly Ser Cys Gly Trp Ile Gly Leu Leu Asp Asp Asp Lys
            20                  25                  30
```

<210> SEQ ID NO 40
<211> LENGTH: 5
<212> TYPE: PRT
<213> ORGANISM: Artificial Sequence
<220> FEATURE:
<223> OTHER INFORMATION: Synthetic

<400> SEQUENCE: 40

```
Asp Asp Asp Asp Lys
1               5
```

<210> SEQ ID NO 41
<211> LENGTH: 50
<212> TYPE: PRT
<213> ORGANISM: Artificial Sequence
<220> FEATURE:
<223> OTHER INFORMATION: Synthetic

<400> SEQUENCE: 41

```
Pro Ala Asp Asp Ala Pro Ala Asp Asp Ala Pro Ala Asp Asp Ala Pro
1               5                   10                  15

Ala Asp Asp Ala Pro Ala Asp Asp Ala Pro Ala Asp Asp Ala Thr Thr
            20                  25                  30

Cys Ile Leu Lys Gly Ser Cys Gly Trp Ile Gly Leu Leu Asp Asp Asp
        35                  40                  45

Asp Lys
    50
```

<210> SEQ ID NO 42
<211> LENGTH: 48
<212> TYPE: DNA
<213> ORGANISM: Artificial Sequence
<220> FEATURE:
<223> OTHER INFORMATION: Synthetic

<400> SEQUENCE: 42
atctcgagac catgtgtgaa cttgatattt tacatgattc tctttacc            48

<210> SEQ ID NO 43
<211> LENGTH: 36
<212> TYPE: DNA
<213> ORGANISM: Artificial Sequence
<220> FEATURE:
<223> OTHER INFORMATION: Synthetic

<400> SEQUENCE: 43
gattgatcat tatcataatt tccccaaagc gtaacc            36

<210> SEQ ID NO 44
<211> LENGTH: 22
<212> TYPE: PRT
<213> ORGANISM: Artificial Sequence
<220> FEATURE:
<223> OTHER INFORMATION: Synthetic

<400> SEQUENCE: 44

```
Met Glu His Trp Ser Tyr Gly Leu Arg Pro Gly Lys Phe Ala Ile Cys
1               5                   10                  15

Lys Lys Phe Ala Ile Cys
            20
```

<210> SEQ ID NO 45
<211> LENGTH: 24
<212> TYPE: PRT
<213> ORGANISM: Artificial Sequence
<220> FEATURE:
<223> OTHER INFORMATION: Synthetic

<400> SEQUENCE: 45

Glu His Trp Ser Tyr Gly Leu Arg Pro Gly Lys Phe Ala Lys Phe Ala
1               5                   10                  15

Lys Lys Phe Ala Lys Phe Ala Lys
            20

<210> SEQ ID NO 46
<211> LENGTH: 30
<212> TYPE: PRT
<213> ORGANISM: Artificial Sequence
<220> FEATURE:
<223> OTHER INFORMATION: Synthetic

<400> SEQUENCE: 46

Met Lys Phe Ala Lys Phe Ala Lys Lys Phe Ala Lys Phe Ala Lys Ser
1               5                   10                  15

Tyr Ala Val Ala Leu Ser Cys Gln Cys Ala Leu Cys Arg Arg
            20                  25                  30

<210> SEQ ID NO 47
<211> LENGTH: 11593
<212> TYPE: DNA
<213> ORGANISM: Artificial Sequence
<220> FEATURE:
<223> OTHER INFORMATION: Synthetic

<400> SEQUENCE: 47

| | |
|---|---|
| ctgacgcgcc ctgtagcggc gcattaagcg cggcgggtgt ggtggttacg cgcagcgtga | 60 |
| ccgctacact tgccagcgcc ctagcgcccg ctcctttcgc tttcttccct tcctttctcg | 120 |
| ccacgttcgc cggcatcaga ttggctattg gccattgcat acgttgtatc catatcataa | 180 |
| tatgtacatt tatattggct catgtccaac attaccgcca tgttgacatt gattattgac | 240 |
| tagttattaa tagtaatcaa ttacggggtc attagttcat agcccatata tggagttccg | 300 |
| cgttacataa cttacggtaa atggcccgcc tggctgaccg cccaacgacc cccgcccatt | 360 |
| gacgtcaata atgacgtatg ttcccatagt aacgccaata gggactttcc attgacgtca | 420 |
| atgggtggag tatttacggt aaactgccca cttggcagta catcaagtgt atcatatgcc | 480 |
| aagtacgccc cctattgacg tcaatgacgg taaatggccc gcctggcatt atgcccagta | 540 |
| catgacctta tgggactttc ctacttggca gtacatctac gtattagtca tcgctattac | 600 |
| catggtgatg cggttttggc agtacatcaa tgggcgtgga tagcggtttg actcacgggg | 660 |
| atttccaagt ctccacccca ttgacgtcaa tgggagtttg ttttggcacc aaaatcaacg | 720 |
| ggactttcca aaatgtcgta caactccgcc ccattgacg caaatgggcg gtaggcgtgt | 780 |
| acggtgggag gtctatataa gcagagctcg tttagtgaac cgtcagatcg cctggagacg | 840 |
| ccatccacgc tgttttgacc tccatagaag acaccgggac cgatccagcc tccgcggccg | 900 |
| ggaacggtgc attggaacgc ggattccccg tgccaagagt gacgtaagta ccgcctatag | 960 |
| actctatagg cacacccctt ggctcttat gcatgctata ctgttttggg cttgggcct | 1020 |
| atacaccccc gcttccttat gctataggtg atggtatagc ttagcctata ggtgtgggtt | 1080 |
| attgaccatt attgaccact cccctattgg tgacgatact ttccattact aatccataac | 1140 |

```
atggctcttt gccacaacta tctctattgg ctatatgcca atactctgtc cttcagagac    1200
tgacacggac tctgtatttt tacaggatgg ggtcccattt attatttaca aattcacata    1260
tacaacaacg ccgtcccccg tgcccgcagt ttttattaaa catagcgtgg gatctccacg    1320
cgaatctcgg gtacgtgttc cggacatggg ctcttctccg gtagcggcgg agcttccaca    1380
tccgagccct ggtcccatgc ctccagcggc tcatggtcgc tcggcagctc cttgctccta    1440
acagtggagg ccagacttag gcacagcaca atgcccacca ccaccagtgt gccgcacaag    1500
gccgtggcgg tagggtatgt gtctgaaaat gagcgtggag attgggctcg cacggctgac    1560
gcagatggaa gacttaaggc agcggcagaa gaagatgcag gcagctgagt tgttgtattc    1620
tgataagagt cagaggtaac tcccgttgcg gtgctgttaa cggtggaggg cagtgtagtc    1680
tgagcagtac tcgttgctgc cgcgcgcgcc accagacata atagctgaca gactaacaga    1740
ctgttccttt ccatgggtct tttctgcagt caccgtcgga ccatgtgcga actcgatatt    1800
ttacacgact ctctttacca attctgcccc gaattacact taaaacgact caacagctta    1860
acgttggctt gccacgcatt acttgactgt aaaactctca ctcttaccga acttggccgt    1920
aacctgccaa ccaaagcgag aacaaaacat aacatcaaac gaatcgaccg attgttaggt    1980
aatcgtcacc tccacaaaga gcgactcgct gtataccgtt ggcatgctag ctttatctgt    2040
tcgggcaata cgatgcccat tgtacttgtt gactggtctg atattcgtga gcaaaaacga    2100
cttatggtat tgcgagcttc agtcgcacta cacggtcgtt ctgttactct ttatgagaaa    2160
gcgttcccgc tttcagagca atgttcaaag aaagctcatg accaatttct agccgacctt    2220
gcgagcattc taccgagtaa caccacaccg ctcattgtca gtgatgctgg ctttaaagtg    2280
ccatggtata aatccgttga gaagctgggt tggtactggt taagtcgagt aagaggaaaa    2340
gtacaatatg cagacctagg agcggaaaac tggaaaccta tcagcaactt acatgatatg    2400
tcatctagtc actcaaagac tttaggctat aagaggctga ctaaaagcaa tccaatctca    2460
tgccaaattc tattgtataa atctcgctct aaaggccgaa aaaatcagcg ctcgacacgg    2520
actcattgtc accacccgtc acctaaaatc tactcagcgt cggcaaagga gccatgggtt    2580
ctagcaacta acttacctgt tgaaattcga acacccaaac aacttgttaa tatctattcg    2640
aagcgaatgc agattgaaga aaccttccga gacttgaaaa gtcctgccta cggactaggc    2700
ctacgccata gccgaacgag cagctcagag cgttttgata tcatgctgct aatcgccctg    2760
atgcttcaac taacatgttg gcttgcgggc gttcatgctc agaaacaagg ttgggacaag    2820
cacttccagg ctaacacagt cagaaatcga aacgtactct caacagttcg cttaggcatg    2880
gaagttttgc ggcattctgg ctacacaata acaagggaag acttactcgt ggctgcaacc    2940
ctactagctc aaaatttatt cacacatggt tacgctttgg ggaaattatg aggggatcgc    3000
tctagagcga tccgggatct cgggaaaagc gttggtgacc aaaggtgcct tttatcatca    3060
ctttaaaaat aaaaaacaat tactcagtgc ctgttataag cagcaattaa ttatgattga    3120
tgcctacatc acaacaaaaa ctgatttaac aaatggttgg tctgccttag aaagtatatt    3180
tgaacattat cttgattata ttattgataa taataaaaac cttatcccta tccaagaagt    3240
gatgcctatc attggttgga atgaacttga aaaaaattag ccttgaatac attactggta    3300
aggtaaacgc cattgtcagc aaattgatcc aagagaacca acttaaagct ttcctgacgg    3360
aatgttaatt ctcgttgacc ctgagcactg atgaatcccc taatgatttt ggtaaaaatc    3420
attaagttaa ggtggataca catcttgtca tatgatcccg gtaatgtgag ttagctcact    3480
cattaggcac cccaggcttt acactttatg cttccggctc gtatgttgtg tggaattgtg    3540
```

```
agcggataac aatttcacac aggaaacagc tatgaccatg attacgccaa gcgcgcaatt   3600
aaccctcact aaagggaaca aaagctggag ctccaccgcg gtggcggccg ctctagaact   3660
agtggatccc ccgggctgca ggaattcgat atcaagctta tcgataccgc tgacctcgag   3720
catcagattg gctattggcc attgcatacg ttgtatccat atcataatat gtacatttat   3780
attggctcat gtccaacatt accgccatgt tgacattgat tattgactag ttattaatag   3840
taatcaatta cggggtcatt agttcatagc ccatatatgg agttccgcgt tacataactt   3900
acggtaaatg gcccgcctgg ctgaccgccc aacgacccccgcccattgac gtcaataatg   3960 acgtatgttc ccatagtaac gccaataggg actttccatt gacgtcaatg ggtggagtat   4020
ttacggtaaa ctgcccactt ggcagtacat caagtgtatc atatgtcaag tacgccccct   4080
attgacgtca atgacggtaa atggcccgcc tggcattatg cccagtacat gaccttatgg   4140
gactttccta cttggcagta catctacgta ttagtcatcg ctattaccat ggtgatgcgg   4200
ttttggcagt acatcaatgg gcgtggatag cggtttgact cacggggatt tccaagtctc   4260
caccccattg acgtcaatgg gagtttgttt tggcaccaaa atcaacggga ctttccaaaa   4320
tgtcgtaaca actccgcccc attgacgcaa atgggcggta ggcgtgtacg gtgggaggtc   4380
tatataagca gagctcgttt agtgaaccgt cagatcgcct ggagacgcca tccacgctgt   4440
tttgacctcc atagaagaca ccgggaccga tccagcctcc gcggccggga acggtgcatt   4500
ggaacgcgga ttccccgtgc caagagtgac gtaagtaccg cctatagact ctataggcac   4560
acccctttgg ctcttatgca tgctatactg tttttggctt ggggcctata cacccccgct   4620
tccttatgct ataggtgatg gtatagctta gcctataggt gtgggttatt gaccattatt   4680
gaccactccc ctattggtga cgatactttc cattactaat ccataacatg gctctttgcc   4740
acaactatct ctattggcta tatgccaata ctctgtcctt cagagactga cacggactct   4800 gtattttttac aggatggggt cccatttatt atttacaaat tcacatatac aacaacgccg   4860
tcccccgtgc ccgcagtttt tattaaacat agcgtgggat ctccacgcga atctcgggta   4920
cgtgttccgg acatgggctc ttctccggta gcggcggagc ttccacatcc gagccctggt   4980
cccatgcctc cagcggctca tggtcgctcg gcagctcctt gctcctaaca gtggaggcca   5040
gacttaggca cagcacaatg cccaccacca ccagtgtgcc gcacaaggcc gtggcggtag   5100
ggtatgtgtc tgaaaatgag cgtggagatt gggctcgcac ggctgacgca gatggaagac   5160
ttaaggcagc ggcagaagaa gatgcaggca gctgagttgt tgtattctga taagagtcag   5220
aggtaactcc cgttgcggtg ctgttaacgg tggagggcag tgtagtctga gcagtactcg   5280
ttgctgccgc gcgcgccacc agacataata gctgacagac taacagactg ttcctttcca   5340
tgggtctttt ctgcagtcac cgtcggatca atcattcatc tcgtgacttc ttcgtgtgtg   5400
gtgtttacct atatatctaa atttaatatt tcgtttatta aaatttaata tatttcgacg   5460
atgaatttct caaggatatt tttcttcgtg ttcgctttgg ttctggcttt gtcaacagtt   5520
tcggctgcgc cagagccgaa aggtacccag gtgcagctgc aggagtcggg ggaggcttg    5580 gtaaagccgg gggggtccct tagagtctcc tgtgcagcct ctggattcac tttcagaaac   5640
gcctggatga gctgggtccg ccaggctcca gggaagggggc tggagtgggt cggccgtatt   5700
aaaagcaaaa ttgatggtgg gacaacagac tatgctgcac ccgtgaaagg cagattcacc   5760
atctcaagag atgattcaaa aaacacgtta tatctgcaaa tgaatagcct gaaagccgag   5820
gacacagccg tatattactg taccacgggg attatgataa catttggggg agttatccct   5880
cccccgaatt ggggccaggg aaccctggtc accgtctcct cagcctccac caagggccca   5940
```

```
tcggtcttcc ccctggcacc ctcctccaag agcacctctg ggggcacagc ggccctgggc    6000
tgcctggtca aggactactt ccccgaaccg gtgacggtgt cgtggaactc aggcgccctg    6060
accagcggcg tgcacacctt tccggctgtc ctacagtcct caggactcta cttccttagc    6120
aacgtggtga ccgtgccctc cagcagcttg ggcacccaga cctacatctg caacgtgaat    6180
cacaagccca gcaacaccaa ggtggacaag aaagttgagc ccaaatcttg tgacaaaact    6240
cacacatgcc caccgtgccc agcacctgaa ctcctggggg gaccgtcagt cttcctcttc    6300
cccccaaaac ccaaggacac cctcatgatc tcccggaccc ctgaggtcac atgcgtggtg    6360
gtggacgtga gccacgaaga ccctgaggtc aagttcaact ggtacgtgga cggcgtggag    6420
gtgcataatg ccaagacaaa gccgcgggag gagcagtaca acagcacgta ccgtgtggtc    6480
agcgtcctca ccgtcctgca ccaggactgg ctgaatggca aggagtacaa gtgcaaggtc    6540
tccaacaaag ccctcccagc ccccatcgag aaaaccatct ccaaagccaa agggcagccc    6600
cgagaaccac aggtgtacac cctgccccca tcccgggatg agctgaccaa gaaccaggtc    6660
agcctgacct gcctggtcaa aggcttctat cccagcgaca tcgccgtgga gtgggagagc    6720
aatgggcagc cggagaacaa ctacaagacc acgcctcccg tgctggactc cgacggctcc    6780
ttcttcctct acagcaagct caccgtggac aagagcaggt ggcagcaggg gaacgtcttc    6840
tcatgctccg tgatgcatga ggctctgcac aaccactaca cgcagaagag cctctccctg    6900
tctccgggta aagcgccaga gccgaaaaag ctttcctatg agctgacaca gccaccctcg    6960
gtgtcagtgt ccccaggaca aacggccagg atcacctgct ctggagatgc attgccagaa    7020
aaatatgttt attggtacca gcagaagtca ggccaggccc ctgtggtggt catctatgag    7080
gacagcaaac gaccctccgg gatccctgag agattctctg gctccagctc agggacaatg    7140
gccaccttga ctatcagtgg ggcccaggtg gaagatgaag gtgactacta ctgttactca    7200
actgacagca gtggttatca tagggaggtg ttcagcggag ggaccaagct gaccgtccta    7260
ggtcagccca aggctgcccc ctcggtcact ctgttcccac cctcctctga ggagcttcaa    7320
gccaacaagg ccacactggt gtgtctcata agtgactcct acccgggagc cgtgacagtg    7380
gcctggaagg cagatagcag ccccgtcaag gcgggagtgg agaccaccac accctccaaa    7440
caaagcaaca caagtacgc ggccagcagc tacctgagcc tgacgcttga gcagtggaag    7500
tcccacaaaa gctacagctg ccaggtcacg catgaaggga gcaccgtgga aagacagtg    7560 gcccctgcag aatgttcacc gcggaggag ggaagggccc tttttgaagg gggaggaaac    7620
ttcgcgccat gactcctctc gtgccccccg cacggaacac tgatgtgcag agggccctct    7680
gccattgctg cttcctctgc ccttcctcgt cactctgaat gtggcttctt tgctactgcc    7740
acagcaagaa ataaaatctc aacatctaaa tgggtttcct gagattttc aagagtcgtt    7800 aagcacattc cttccccagc acccccttgct gcaggccagt gccaggcacc aacttggcta    7860
ctgctgccca tgagagaaat ccagttcaat attttccaaa gcaaatgga ttacatatgc    7920 cctagatcct gattaacagg tgttttgtat tatctgtgct ttcgcttcac ccacattatc    7980
ccattgcctc ccctcgaggg gggcccggt acccaattcg ccctatagtg agtcgtatta    8040
cgcgcgctca ctggccgtcg ttttacaacg tcgtgactgg gaaaaccctg gcgttaccca    8100
acttaatcgc cttgcagcac atccccctt cgccagctgg cgtaatagcg aagaggcccg    8160
caccgatcgc ccttcccaac agttgcgcag cctgaatggc gaatggaaat tgtaagcgtt    8220 aatatttgt taaattcgc gttaaatttt tgttaaatca gctcattttt taaccaatag    8280
gccgaaatcg gcaaaatccc ttataaatca aagaatagac cgagatagg gttgagtgtt    8340
```

```
gttccagttt ggaacaagag tccactatta agaacgtgg actccaacgt caaagggcga   8400
aaaaccgtct atcagggcga tggcccacta ctccgggatc atatgacaag atgtgtatcc   8460
accttaactt aatgattttt accaaaatca ttaggggatt catcagtgct cagggtcaac   8520
gagaattaac attccgtcag gaaagcttat gatgatgatg tgcttaaaaa cttactcaat   8580
ggctggttat gcatatcgca atacatgcga aaaacctaaa agagcttgcc gataaaaaag   8640
gccaatttat tgctatttac cgcggctttt tattgagctt gaaagataaa taaaatagat   8700
aggttttatt tgaagctaaa tcttctttat cgtaaaaaat gccctcttgg ttatcaaga    8760
gggtcattat atttcgcgga ataacatcat ttggtgacga ataactaag cacttgtctc    8820
ctgtttactc ccctgagctt gaggggttaa catgaaggtc atcgatagca ggataataat   8880
acagtaaaac gctaaaccaa taatccaaat ccagccatcc caaattggta gtgaatgatt   8940
ataaataaca gcaaacagta atgggccaat aacaccggtt gcattggtaa ggctcaccaa   9000
taatccctgt aaagcacctt gctgatgact ctttgtttgg atagacatca ctccctgtaa   9060
tgcaggtaaa gcgatcccac caccagccaa taaaattaaa acagggaaaa ctaaccaacc   9120
ttcagatata aacgctaaaa aggcaaatgc actactatct gcaataaatc cgagcagtac   9180
tgccgttttt tcgcccattt agtggctatt cttcctgcca caaaggcttg gaatactgag   9240
tgtaaaagac caagacccgt aatgaaaagc caaccatcat gctattcatc atcacgattt   9300
ctgtaatagc accacaccgt gctggattgg ctatcaatgc gctgaaataa taatcaacaa   9360
atggcatcgt taaataagtg atgtataccg atcagctttt gttccctttta gtgagggtta  9420
attgcgcgct tggcgtaatc atggtcatag ctgtttcctg tgtgaaattg ttatccgctc   9480
acaattccac acaacatacg agccggaagc ataaagtgta aagcctgggg tgcctaatga   9540
gtgagctaac tcacattaat tgcgttgcgc tcactgcccg ctttccagtc gggaaacctg   9600
tcgtgccagc tgcattaatg aatcggccaa cgcgcgggga gaggcggttt gcgtattggg   9660
cgctcttccg cttcctcgct cactgactcg ctgcgctcgg tcgttcggct gcggcgagcg   9720
gtatcagctc actcaaaggc ggtaatacgg ttatccacag aatcagggga taacgcagga   9780
aagaacatgt gagcaaaagg ccagcaaaag gccaggaacc gtaaaaaggc cgcgttgctg   9840
gcgtttttcc ataggctccg ccccctgac gagcatcaca aaaatcgacg ctcaagtcag    9900
aggtggcgaa acccgacagg actataaaga taccaggcgt ttccccctgg aagctccctc   9960
gtgcgctctc ctgttccgac cctgccgctt accggatacc tgtccgcctt ctctcccttcg 10020
ggaagcgtgg cgctttctca tagctcacgc tgtaggtatc tcagttcggt gtaggtcgtt  10080
cgctccaagc tgggctgtgt gcacgaaccc ccgttcagc ccgaccgctg cgccttatcc   10140
ggtaactatc gtcttgagtc aacccggta agacacgact tatcgccact ggcagcagcc   10200
actggtaaca ggattagcag agcgaggtat gtaggcggtg ctacagagtt cttgaagtgg   10260
tggcctaact acggctacac tagaaggaca gtatttggta tctgcgctct gctgaagcca   10320
gttaccttcg gaaaaagagt tggtagctct tgatccggca aacaaaccac cgctggtagc   10380
ggtggttttt ttgtttgcaa gcagcagatt acgcgcagaa aaaaggatc tcaagaagat   10440
cctttgatct tttctacggg gtctgacgct cagtggaacg aaaactcacg ttaagggatt   10500
ttggtcatga gattatcaaa aaggatcttc acctagatcc ttttaaatta aaatgaagt    10560
tttaaatcaa tctaaagtat atatgagtaa acttggtctg acagttacca atgcttaatc   10620
agtgaggcac ctatctcagc gatctgtcta tttcgttcat ccatagttgc ctgactcccc   10680
gtcgtgtaga taactacgat acgggagggc ttaccatctg gccccagtgc tgcaatgata   10740
```

```
ccgcgagacc cacgctcacc ggctccagat ttatcagcaa taaaccagcc agccggaagg    10800
gccgagcgca gaagtggtcc tgcaacttta tccgcctcca tccagtctat taattgttgc    10860
cgggaagcta gagtaagtag ttcgccagtt aatagtttgc gcaacgttgt tgccattgct    10920
acaggcatcg tggtgtcacg ctcgtcgttt ggtatggctt cattcagctc cggttcccaa    10980
cgatcaaggc gagttacatg atcccccatg ttgtgcaaaa aagcggttag ctccttcggt    11040
cctccgatcg ttgtcagaag taagttggcc gcagtgttat cactcatggt tatggcagca    11100
ctgcataatt ctcttactgt catgccatcc gtaagatgct tttctgtgac tggtgagtac    11160
tcaaccaagt cattctgaga atagtgtatg cggcgaccga gttgctcttg cccggcgtca    11220
atacgggata ataccgcgcc acatagcaga actttaaaag tgctcatcat tggaaaacgt    11280 tcttcgggc gaaaactctc aaggatctta ccgctgttga tccagttc gatgtaaccc       11340 actcgtgcac ccaactgatc ttcagcatct tttactttca ccagcgtttc tgggtgagca    11400
aaaacaggaa ggcaaaatgc cgcaaaaaag ggaataaggg cgacacggaa atgttgaata    11460
ctcatactct tcctttttca atattattga agcatttatc agggttattg tctcatgagc    11520
ggatacatat ttgaatgtat ttagaaaaat aaacaaatag gggttccgcg cacatttccc    11580
cgaaaagtgc cac                                                       11593
```

<210> SEQ ID NO 48  
<211> LENGTH: 11590  
<212> TYPE: DNA  
<213> ORGANISM: Artificial Sequence  
<220> FEATURE:  
<223> OTHER INFORMATION: Synthetic

<400> SEQUENCE: 48

```
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggcatcaga ttggctattg gccattgcat acgttgtatc catatcataa     180
tatgtacatt tatattggct catgtccaac attaccgcca tgttgacatt gattattgac     240
tagttattaa tagtaatcaa ttacggggtc attagttcat agcccatata tggagttccg     300
cgttacataa cttacggtaa atggcccgcc tggctgaccg cccaacgacc cccgcccatt     360
gacgtcaata atgacgtatg ttcccatagt aacgccaata gggactttcc attgacgtca     420
atgggtggag tatttacggt aaactgccca cttggcagta catcaagtgt atcatatgcc     480
aagtacgccc cctattgacg tcaatgacgg taaatggccc gcctggcatt atgcccagta     540
catgacctta tgggactttc ctacttggca gtacatctac gtattagtca tcgctattac     600
catggtgatg cggttttggc agtacatcaa tgggcgtgga tagcggtttg actcacgggg     660
atttccaagt ctccacccca ttgacgtcaa tgggagtttg ttttggcacc aaaatcaacg     720
ggactttcca aaatgtcgta caactccgc cccattgacg caaatgggcg gtaggcgtgt     780
acggtgggag gtctatataa gcagagctcg tttagtgaac cgtcagatcg cctggagacg     840
ccatccacgc tgttttgacc tccatagaag acaccgggac cgatccagcc tccgcggccg     900
ggaacggtgc attggaacgc ggattccccg tgccaagagt gacgtaagta ccgcctatag     960
actctatagg cacaccccct tggctcttat gcatgctata ctgtttttgg cttggggcct    1020
atacaccccc gcttccttat gctataggtg atggtatagc ttagcctata ggtgtgggtt    1080
attgaccatt attgaccact cccctattgg tgacgatact ttccattact aatccataac    1140
atggctcttt gccacaacta tctctattgg ctatatgcca atactctgtc cttcagagac    1200
```

```
tgacacggac tctgtatttt tacaggatgg ggtcccattt attatttaca aattcacata    1260
tacaacaacg ccgtccccg tgcccgcagt ttttattaaa catagcgtgg gatctccacg     1320
cgaatctcgg gtacgtgttc cggacatggg ctcttctccg gtagcggcgg agcttccaca    1380
tccgagccct ggtcccatgc ctccagcggc tcatggtcgc tcggcagctc cttgctccta   1440
acagtggagg ccagacttag gcacagcaca atgcccacca ccaccagtgt gccgcacaag    1500
gccgtggcgg tagggtatgt gtctgaaaat gagcgtggag attgggctcg cacggctgac    1560
gcagatggaa gacttaaggc agcggcagaa gaagatgcag gcagctgagt tgttgtattc    1620
tgataagagt cagaggtaac tcccgttgcg gtgctgttaa cggtggaggg cagtgtagtc    1680
tgagcagtac tcgttgctgc cgcgcgcgcc accagacata atagctgaca gactaacaga    1740
ctgttccttt ccatgggtct tttctgcagt caccgtcgga ccatgtgcga actcgatatt    1800
ttacacgact ctctttacca attctgcccc gaattacact taaaacgact caacagctta    1860
acgttggctt gccacgcatt acttgactgt aaaactctca ctcttaccga acttggccgt    1920
aacctgccaa ccaaagcgag aacaaaacat aacatcaaac gaatcgaccg attgttaggt    1980
aatcgtcacc tccacaaaga gcgactcgct gtataccgtt ggcatgctag ctttatctgt    2040
tcgggcaata cgatgcccat tgtacttgtt gactggtctg atattcgtga gcaaaaacga    2100
cttatggtat tgcgagcttc agtcgcacta cacggtcgtt ctgttactct ttatgagaaa    2160
gcgttcccgc tttcagagca atgttcaaag aaagctcatg accaatttct agccgacctt    2220
gcgagcattc taccgagtaa caccacaccg ctcattgtca gtgatgctgg ctttaaagtg    2280
ccatggtata atccgttga gaagctgggt tggtactggt taagtcgagt aagaggaaaa     2340
gtacaatatg cagacctagg agcggaaaac tggaaaccta tcagcaactt acatgatatg    2400
tcatctagtc actcaaagac tttaggctat aagaggctga ctaaaagcaa tccaatctca    2460
tgccaaattc tattgtataa atctcgctct aaaggccgaa aaaatcagcg ctcgacacgg    2520
actcattgtc accacccgtc acctaaaatc tactcagcgt cggcaaagga gccatgggtt    2580
ctagcaacta acttacctgt tgaaattcga acacccaaac aacttgttaa tatctattcg    2640
aagcgaatgc agattgaaga aaccttccga gacttgaaaa gtcctgccta cggactaggc    2700
ctacgccata gccgaacgag cagctcagag cgttttgata tcatgctgct aatcgccctg    2760
atgcttcaac taacatgttg gcttgcgggc gttcatgctc agaaacaagg ttgggacaag    2820
cacttccagg ctaacacagt cagaaatcga aacgtactct caacagttcg cttaggcatg    2880
gaagttttgc ggcattctgg ctacacaata acaagggaag acttactcgt ggctgcaacc    2940
ctactagctc aaaatttatt cacacatggt tacgctttgg ggaaattatg aggggatcgc    3000
tctagagcga tccgggatct cgggaaaagc gttggtgacc aaaggtgcct tttatcatca    3060
ctttaaaaat aaaaaacaat tactcagtgc ctgttataag cagcaattaa ttatgattga    3120
tgcctacatc acaacaaaaa ctgatttaac aaatggttgg tctgccttag aaagtatatt    3180
tgaacattat cttgattata ttattgataa taataaaaac cttatcccta tccaagaagt    3240
gatgcctatc attggttgga atgaacttga aaaaaattag ccttgaatac attactggta    3300
aggtaaacgc cattgtcagc aaattgatcc aagagaacca acttaaagct ttcctgacgg    3360
aatgttaatt ctcgttgacc ctgagcactg atgaatcccc taatgatttt ggtaaaaatc    3420
attaagttaa ggtggataca catcttgtca tatgatcccg gtaatgtgag ttagctcact    3480
cattaggcac cccaggcttt acactttatg cttccggctc gtatgttgtg tggaattgtg    3540
agcggataac aatttcacac aggaaacagc tatgaccatg attacgccaa gcgcgcaatt    3600
```

```
aaccctcact aaagggaaca aaagctggag ctccaccgcg gtggcggccg ctctagaact   3660
agtggatccc ccgggctgca ggaattcgat atcaagctta tcgataccgc tgacctcgag   3720
catcagattg gctattggcc attgcatacg ttgtatccat atcataatat gtacatttat   3780
attggctcat gtccaacatt accgccatgt tgacattgat tattgactag ttattaatag   3840
taatcaatta cggggtcatt agttcatagc ccatatatgg agttccgcgt tacataactt   3900
acggtaaatg gcccgcctgg ctgaccgccc aacgaccccc gcccattgac gtcaataatg   3960
acgtatgttc ccatagtaac gccaataggg actttccatt gacgtcaatg ggtggagtat   4020
ttacggtaaa ctgcccactt ggcagtacat caagtgtatc atatgtcaag tacgcccct   4080 attgacgtca atgacggtaa atggcccgcc tggcattatg cccagtacat gaccttatgg   4140
gactttccta cttggcagta catctacgta ttagtcatcg ctattaccat ggtgatgcgg   4200
ttttggcagt acatcaatgg gcgtggatag cggtttgact cacggggatt tccaagtctt   4260
caccccattg acgtcaatgg gagtttgttt tggcaccaaa atcaacggga ctttccaaaa   4320
tgtcgtaaca actccgcccc attgacgcaa atgggcggta ggcgtgtacg gtgggaggtc   4380
tatataagca gagctcgttt agtgaaccgt cagatcgcct ggagacgcca tccacgctgt   4440
tttgacctcc atagaagaca ccgggaccga tccagcctcc gcggccggga acggtgcatt   4500
ggaacgcgga ttccccgtgc caagagtgac gtaagtaccg cctatagact ctataggcac   4560
acccctttgg ctcttatgca tgctatactg ttttggctt ggggcctata caccccgct   4620 tccttatgct ataggtgatg gtatagctta gcctataggt gtgggttatt gaccattatt   4680
gaccactccc ctattggtga cgatactttc cattactaat ccataacatg gctctttgcc   4740
acaactatct ctattggcta tatgccaata ctctgtcctt cagagactga cacggactct   4800
gtatttttac aggatggggt cccatttatt atttacaaat tcacatatac aacaacgccg   4860
tcccccgtgc ccgcagtttt tattaaacat agcgtgggat ctccacgcga atctcgggta   4920
cgtgttccgg acatgggctc ttctccggta gcggcggagc ttccacatcc gagccctggt   4980
cccatgcctc cagcggctca tggtcgctcg gcagctcctt gctcctaaca gtggaggcca   5040
gacttaggca cagcacaatg cccaccacca ccagtgtgcc gcacaaggcc gtggcggtag   5100
ggtatgtgtc tgaaaatgag cgtggagatt gggctcgcac ggctgacgca gatgcaaaagac   5160 ttaaggcagc ggcagaagaa gatgcaggca gctgagttgt tgtattctga taagagtcag   5220
aggtaactcc cgttgcggtg ctgttaacgg tggaggcag tgtagtctga gcagtactcg   5280
ttgctgccgc gcgcgccacc agacataata gctgacagac taacagactg ttccttcca   5340 tgggtctttt ctgcagtcac cgtcggatca atcattcatc tcgtgacttc ttcgtgtgtg   5400
gtgtttacct atatatctaa atttaatatt tcgtttatta aaatttaata tatttcgacg   5460
atgaatttct caaggatatt tttcttcgtg ttcgctttgg ttctggcttt gtcaacagtt   5520
tcggctgcgc cagagccgaa aggtacccag gtgcagctgc aggagtcggg gggaggcttg   5580
gtaaagccgg gggggtccct tagagtctcc tgtgcagcct ctggattcac tttcagaaac   5640
gcctggatga gctgggtccg ccaggctcca gggaagggc tggagtgggt cggccgtatt   5700
aaaagcaaaa ttgatggtgg acaacagaca tatgctgcac ccgtgaaagg cagattcacc   5760
atctcaagag atgattcaaa aaacacgtta tatctgcaaa tgaatagcct gaaagccgag   5820
gacacagccg tatattactg taccacgggg attatgataa catttggggg agttatccct   5880
cccccgaatt ggggccaggg aaccctggtc accgtctcct cagcctccac caagggccca   5940
tcggtcttcc ccctggcacc ctcctccaag agcacctctg ggggcacagc ggccctgggc   6000
```

```
tgcctggtca aggactactt ccccgaaccg gtgacggtgt cgtggaactc aggcgccctg   6060
accagcggcg tgcacacctt tccggctgtc ctacagtcct caggactcta cttccttagc   6120
aacgtggtga ccgtgccctc cagcagcttg ggcacccaga cctacatctg caacgtgaat   6180
cacaagccca gcaacaccaa ggtggacaag aaagttgagc ccaaatcttg tgacaaaact   6240
cacacatgcc caccgtgccc agcacctgaa ctcctggggg gaccgtcagt cttcctcttc   6300
cccccaaaac ccaaggacac cctcatgatc tcccggaccc ctgaggtcac atgcgtggtg   6360
gtggacgtga gccacgaaga ccctgaggtc aagttcaact ggtacgtgga cggcgtggag   6420
gtgcataatg ccaagacaaa gccgcgggag gagcagtaca acagcacgta ccgtgtggtc   6480
agcgtcctca ccgtcctgca ccaggactgg ctgaatggca aggagtacaa gtgcaaggtc   6540
tccaacaaag cccteccagc ccccatcgag aaaaccatct ccaaagccaa agggcagccc   6600
cgagaaccac aggtgtacac cctgccccca tcccgggatg agctgaccaa gaaccaggtc   6660
agcctgacct gcctggtcaa aggcttctat cccagcgaca tcgccgtgga gtgggagagc   6720
aatgggcagc cggagaacaa ctacaagacc acgcctcccg tgctggactc cgacggctcc   6780
ttcttcctct acagcaagct caccgtggac aagagcaggt ggcagcaggg gaacgtcttc   6840
tcatgctccg tgatgcatga ggctctgcac aaccactaca cgcagaagag cctctccctg   6900
tctccgggta aagcgccaga gccgaagctt cctatgagc tgacacagcc accctcggtg   6960
tcagtgtccc caggacaaac ggccaggatc acctgctctg gagatgcatt gccagaaaaa   7020
tatgtttatt ggtaccagca gaagtcaggc caggcccctg tggtggtcat ctatgaggac   7080
agcaaacgac cctccgggat ccctgagaga ttctctggct ccagctcagg gacaatggcc   7140
accttgacta tcagtggggc ccaggtggaa gatgaaggtg actactactg ttactcaact   7200
gacagcagtg gttatcatag ggaggtgttc agcggaggga ccaagctgac cgtcctaggt   7260
cagcccaagg ctgccccctc ggtcactctg ttcccaccct cctctgagga gcttcaagcc   7320
aacaaggcca cactggtgtg tctcataagt gactcctacc cgggagccgt gacagtggcc   7380
tggaaggcag atagcagccc cgtcaaggcg ggagtggaga ccaccacacc ctccaaacaa   7440
agcaacaaca gtacgcggc cagcagctac ctgagcctga cgcttgagca gtggaagtcc   7500
cacaaaagct acagctgcca ggtcacgcat gaagggagca ccgtggagaa gacagtggcc   7560
cctgcagaat gttcaccgcg gagggaggga agggcccttt tgaaggggg aggaaacttc   7620 gcgccatgac tcctctcgtg cccccgcac ggaacactga tgtgcagagg gccctctgcc   7680
attgctgctt cctctgccct tcctcgtcac tctgaatgtg gcttctttgc tactgccaca   7740
gcaagaaata aaatctcaac atctaaatgg gtttcctgag attttcaag agtcgttaag   7800 cacattcctt ccccagcacc ccttgctgca ggccagtgcc aggcaccaac ttggctactg   7860
ctgcccatga gagaaatcca gttcaatatt ttccaaagca aaatggatta catatgccct   7920
agatcctgat taacaggtgt tttgtattat ctgtgctttc gcttcaccca cattatccca   7980
ttgcctcccc tcgagggggg gcccggtacc caattcgccc tatagtgagt cgtattacgc   8040
gcgctcactg gccgtcgttt tacaacgtcg tgactgggaa aaccctggcg ttacccaact   8100
taatcgcctt gcagcacatc ccccttcgc cagctggcgt aatagcgaag aggcccgcac   8160
cgatcgccct tcccaacagt tgcgcagcct gaatggcgaa tggaaattgt aagcgttaat   8220
attttgttaa aattcgcgtt aaattttttgt taatcagct cattttttaa ccaataggcc   8280
gaaatcggca aaatccctta taatcaaaa gaatagaccg agataggt gagtgttgtt   8340 ccagtttgga acaagagtcc actattaaag aacgtggact ccaacgtcaa agggcgaaaa   8400
```

```
accgtctatc agggcgatgg cccactactc cgggatcata tgacaagatg tgtatccacc    8460
ttaacttaat gattttttacc aaaatcatta ggggattcat cagtgctcag ggtcaacgag    8520
aattaacatt ccgtcaggaa agcttatgat gatgatgtgc ttaaaaactt actcaatggc    8580
tggttatgca tatcgcaata catgcgaaaa acctaaaaga gcttgccgat aaaaaaggcc    8640
aatttattgc tatttaccgc ggcttttttat tgagcttgaa agataaataa aatagatagg    8700
ttttatttga agctaaatct tctttatcgt aaaaaatgcc ctcttgggtt atcaagaggg    8760
tcattatatt tcgcggaata acatcatttg gtgacgaaat aactaagcac ttgtctcctg    8820
tttactcccc tgagcttgag gggttaacat gaaggtcatc gatagcagga taataataca    8880
gtaaaacgct aaaccaataa tccaaatcca gccatcccaa attggtagtg aatgattata    8940
aataacagca aacagtaatg ggccaataac accggttgca ttggtaaggc tcaccaataa    9000
tccctgtaaa gcaccttgct gatgactctt tgtttggata gacatcactc cctgtaatgc    9060
aggtaaagcg atcccaccac cagccaataa aattaaaaca gggaaaacta accaaccttc    9120
agatataaac gctaaaaagg caaatgcact actatctgca ataaatccga gcagtactgc    9180
cgttttttcg cccatttagt ggctattctt cctgccacaa aggcttggaa tactgagtgt    9240
aaaagaccaa gacccgtaat gaaaagccaa ccatcatgct attcatcatc acgatttctg    9300
taatagcacc acccgtgct ggattggcta tcaatgcgct gaaataataa tcaacaaatg    9360
gcatcgttaa ataagtgatg tataccgatc agcttttgtt cccttagtg agggttaatt    9420
gcgcgcttgg cgtaatcatg gtcatagctg tttcctgtgt gaaattgtta ccgctcaca    9480
attccacaca acatacgagc cggaagcata aagtgtaaag cctggggtgc ctaatgagtg    9540
agctaactca cattaattgc gttgcgctca ctgcccgctt tccagtcggg aaacctgtcg    9600
tgccagctgc attaatgaat cggccaacgc gcggggagag cggtttgcg tattgggcgc    9660
tcttccgctt cctcgctcac tgactcgctg cgctcggtcg ttcggctgcg gcgagcggta    9720
tcagctcact caaaggcggt aatacggtta tccacagaat caggggataa cgcaggaaag    9780
aacatgtgag caaaaggcca gcaaaaggcc aggaaccgta aaaaggccgc gttgctggcg    9840
ttttccata ggctccgccc ccctgacgag catcacaaaa atcgacgctc aagtcagagg    9900
tggcgaaacc cgacaggact ataaagatac caggcgtttc cccctggaag ctccctcgtg    9960
cgctctcctg ttccgaccct gccgcttacc ggatacctgt ccgcctttct cccttcggga    10020
agcgtggcgc tttctcatag ctcacgctgt aggtatctca gttcggtgta ggtcgttcgc    10080
tccaagctgg gctgtgtgca cgaaccccc gttcagcccg accgctgcgc cttatccggt    10140
aactatcgtc ttgagtccaa cccggtaaga cacgacttat cgccactggc agcagccact    10200
ggtaacagga ttagcagagc gaggtatgta ggcggtgcta cagagttctt gaagtggtgg    10260
cctaactacg gctacactag aaggacagta tttggtatct gcgctctgct gaagccagtt    10320
accttcggaa aaagagttgg tagctcttga tccggcaaac aaaccaccgc tggtagcggt    10380
ggtttttttg tttgcaagca gcagattacg cgcagaaaaa aaggatctca agaagatcct    10440
ttgatctttt ctacggggtc tgacgctcag tggaacgaaa actcacgtta agggattttg    10500
gtcatgagat tatcaaaaag gatcttcacc tagatccttt taaattaaaa atgaagtttt    10560
aaatcaatct aaagtatata tgagtaaact tggtctgaca gttaccaatg cttaatcagt    10620
gaggcaccta tctcagcgat ctgtctattt cgttcatcca tagttgcctg actccccgtc    10680
gtgtagataa ctacgatacg ggagggctta ccatctggcc ccagtgctgc aatgataccg    10740
cgagacccac gctcaccggc tccagattta tcagcaataa accagccagc cggaagggcc    10800
```

```
gagcgcagaa gtggtcctgc aactttatcc gcctccatcc agtctattaa ttgttgccgg    10860
gaagctagag taagtagttc gccagttaat agtttgcgca acgttgttgc cattgctaca    10920
ggcatcgtgg tgtcacgctc gtcgtttggt atggcttcat tcagctccgg ttcccaacga    10980
tcaaggcgag ttacatgatc ccccatgttg tgcaaaaaag cggttagctc cttcggtcct    11040
ccgatcgttg tcagaagtaa gttggccgca gtgttatcac tcatggttat ggcagcactg    11100
cataattctc ttactgtcat gccatccgta agatgctttt ctgtgactgg tgagtactca    11160
accaagtcat tctgagaata gtgtatgcgg cgaccgagtt gctcttgccc ggcgtcaata    11220
cgggataata ccgcgccaca tagcagaact ttaaaagtgc tcatcattgg aaaacgttct    11280
tcggggcgaa aactctcaag gatcttaccg ctgttgagat ccagttcgat gtaacccact    11340
cgtgcaccca actgatcttc agcatctttt actttcacca gcgtttctgg gtgagcaaaa    11400
acaggaaggc aaaatgccgc aaaaaaggga taagggcga cacgaaatg ttgaatactc    11460 atactcttcc tttttcaata ttattgaagc atttatcagg gttattgtct catgagcgga    11520
tacatatttg aatgtattta gaaaaataaa caaatagggg ttccgcgcac atttccccga    11580
aaagtgccac                                                          11590

<210> SEQ ID NO 49
<211> LENGTH: 11332
<212> TYPE: DNA
<213> ORGANISM: Artificial Sequence
<220> FEATURE:
<223> OTHER INFORMATION: Synthetic

<400> SEQUENCE: 49
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggcatcaga ttggctattg gccattgcat acgttgtatc catatcataa     180
tatgtacatt tatattggct catgtccaac attaccgcca tgttgacatt gattattgac     240
tagttattaa tagtaatcaa ttacggggtc attagttcat agcccatata tggagttccg     300
cgttacataa cttacggtaa atggcccgcc tggctgaccg cccaacgacc cccgcccatt     360
gacgtcaata atgacgtatg ttcccatagt aacgccaata gggactttcc attgacgtca     420
atgggtggag tatttacggt aaactgccca cttggcagta catcaagtgt atcatatgcc     480
aagtacgccc cctattgacg tcaatgacgg taaatggccc gcctggcatt atgcccagta     540
catgacctta tgggactttc ctacttggca gtacatctac gtattagtca tcgctattac     600
catggtgatg cggttttggc agtacatcaa tgggcgtgga tagcggtttg actcacgggg     660
atttccaagt ctccacccca ttgacgtcaa tgggagtttg ttttggcacc aaaatcaacg     720
ggactttcca aaatgtcgta caactccgcc ccattgacg caaatgggcg gtaggcgtgt     780
acggtgggag gtctatataa gcagagctcg tttagtgaac cgtcagatcg cctggagacg     840
ccatccacgc tgttttgacc tccatagaag acaccgggac cgatccagcc tccgcggccg     900
ggaacggtgc attggaacgc ggattccccg tgccaagagt gacgtaagta ccgcctatag     960
actctatagg cacaccccctt tggctcttat gcatgctata ctgttttgg cttggggcct    1020 atacacccccc gcttccttat gctataggtg atggtatagc ttagcctata ggtgtgggtt    1080
attgaccatt attgaccact cccctattgg tgacgatact ttccattact aatccataac    1140
atggctcttt gccacaacta tctctattgg ctatatgcca atactctgtc cttcagagac    1200
tgacacggac tctgtatttt tacaggatgg ggtcccattt attatttaca aattcacata    1260
```

```
tacaacaacg ccgtcccccg tgcccgcagt ttttattaaa catagcgtgg gatctccacg    1320
cgaatctcgg gtacgtgttc cggacatggg ctcttctccg gtagcggcgg agcttccaca    1380
tccgagccct ggtcccatgc ctccagcggc tcatggtcgc tcggcagctc cttgctccta    1440
acagtggagg ccagacttag gcacagcaca atgcccacca ccaccagtgt gccgcacaag    1500
gccgtggcgg tagggtatgt gtctgaaaat gagcgtggag attgggctcg cacggctgac    1560
gcagatggaa gacttaaggc agcggcagaa gaagatgcag gcagctgagt tgttgtattc    1620
tgataagagt cagaggtaac tcccgttgcg gtgctgttaa cggtggaggg cagtgtagtc    1680
tgagcagtac tcgttgctgc cgcgcgcgcc accagacata atagctgaca gactaacaga    1740
ctgttccttt ccatgggtct tttctgcagt caccgtcgga ccatgtgcga actcgatatt    1800
ttacacgact ctctttacca attctgcccc gaattacact aaaaacgact caacagctta    1860
acgttggctt gccacgcatt acttgactgt aaaactctca ctcttaccga acttggccgt    1920
aacctgccaa ccaaagcgag aacaaaacat aacatcaaac gaatcgaccg attgttaggt    1980
aatcgtcacc tccacaaaga gcgactcgct gtataccgtt ggcatgctag ctttatctgt    2040
tcgggcaata cgatgcccat tgtacttgtt gactggtctg atattcgtga gcaaaaacga    2100
cttatggtat tgcgagcttc agtcgcacta cacggtcgtt ctgttactct ttatgagaaa    2160
gcgttcccgc tttcagagca atgttcaaag aaagctcatg accaatttct agccgacctt    2220
gcgagcattc taccgagtaa caccacaccg ctcattgtca gtgatgctgg ctttaaagtg    2280
ccatggtata aatccgttga gaagctgggt tggtactggt taagtcgagt aagaggaaaa    2340
gtacaatatg cagacctagg agcggaaaac tggaaaccta tcagcaactt acatgatatg    2400
tcatctagtc actcaaagac tttaggctat aagaggctga ctaaaagcaa tccaatctca    2460
tgccaaattc tattgtataa atctcgctct aaaggccgaa aaaatcagcg ctcgacacgg    2520
actcattgtc accacccgtc acctaaaatc tactcagcgt cggcaaagga gccatgggtt    2580
ctagcaacta acttacctgt tgaaattcga acacccaaac aacttgttaa tatctattcg    2640
aagcgaatgc agattgaaga aaccttccga gacttgaaaa gtcctgccta cggactaggc    2700
ctacgccata gccgaacgag cagctcagag cgttttgata tcatgctgct aatcgccctg    2760
atgcttcaac taacatgttg gcttgcgggc gttcatgctc agaaacaagg ttgggacaag    2820
cacttccagg ctaacacagt cagaaatcga acgtactctc aacagttcg cttaggcatg    2880 gaagttttgc ggcattctgg ctacacaata acaagggaag acttactcgt ggctgcaacc    2940
ctactagctc aaaatttatt cacacatggt tacgctttgg ggaaattatg aggggatcgc    3000
tctagagcga tccgggatct cgggaaaagc gttggtgacc aaaggtgcct tttatcatca    3060
ctttaaaaat aaaaaacaat tactcagtgc ctgttataag cagcaattaa ttatgattga    3120
tgcctacatc acaacaaaaa ctgatttaac aaatggttgg tctgccttag aaagtatatt    3180
tgaacattat cttgattata ttattgataa taataaaaac cttatcccta tccaagaagt    3240
gatgcctatc attggttgga atgaacttga aaaaaattag ccttgaatac attactggta    3300
aggtaaacgc cattgtcagc aaattgatcc aagagaacca acttaaagct ttcctgacgg    3360
aatgttaatt ctcgttgacc ctgagcactg atgaatcccc taatgatttt ggtaaaaatc    3420
attaagttaa ggtggataca catcttgtca tatgatcccg gtaatgtgag ttagctcact    3480
cattaggcac cccaggcttt acactttatg cttccggctc gtatgttgtg tggaattgtg    3540
agcggataac aatttcacac aggaaacagc tatgaccatg attacgccaa gcgcgcaatt    3600
aaccctcact aaagggaaca aaagctggag ctccaccgcg gtggcggccg ctctagaact    3660
```

```
agtggatccc ccgggctgca gaaaaatgcc aggtggacta tgaactcaca tccaaaggag    3720
cttgacctga tacctgattt tcttcaaact ggggaaacaa cacaatccca caaacagct     3780 cagagagaaa ccatcactga tggctacagc accaaggtat gcaatggcaa tccattcgac    3840
attcatctgt gacctgagca aaatgattta tctctccatg aatggttgct tctttccctc    3900
atgaaaaggc aatttccaca ctcacaatat gcaacaaaga caaacagaga caattaatg     3960 tgctccttcc taatgtcaaa attgtagtgg caaagaggag aacaaaatct caagttctga    4020
gtaggtttta gtgattggat aagaggcttt gacctgtgag ctcacctgga cttcatatcc    4080
ttttggataa aaagtgcttt tataactttc aggtctccga gtctttattc atgagactgt    4140
tggtttaggg acagacccac aatgaaatgc ctggcatagg aaagggcagc agagccttag    4200
ctgacctttt cttgggacaa gcattgtcaa acaatgtgtg acaaaactat ttgtactgct    4260
ttgcacagct gtgctgggca gggcaatcca ttgccaccta tcccaggtaa ccttccaact    4320
gcaagaagat tgttgcttac tctctctaga agcttctgc  agactgacat gcatttcata    4380
ggtagagata acatttactg ggaagcacat ctatcatcat aaaaagcagg caagattttc    4440
agactttctt agtggctgaa atagaagcaa agacgtgat  taaaaacaaa atgaaacaaa    4500
aaaaatcagt tgatacctgt ggtgtagaca tccagcaaaa aaatattatt tgcactacca    4560
tcttgtctta agtcctcaga cttggcaagg agaatgtaga tttctacagt atatatgttt    4620
tcacaaaagg aaggagagaa acaaaagaaa atggcactga ctaaacttca gctagtggta    4680
taggaaagta attctgctta acagagattg cagtgatctc tatgtatgtc ctgaagaatt    4740
atgttgtact ttttcccc  attttaaat  caaacagtgc tttacagagg tcagaatggt    4800
ttctttactg tttgtcaatt ctattatttc aatacagaac aatagcttct ataactgaaa    4860
tatatttgct attgtatatt atgattgtcc ctcgaaccat gaacactcct ccagctgaat    4920 ttacaattc  ctctgtcatc tgccaggcca ttaagttatt catggaagat ctttgaggaa    4980
cactgcaagt tcatatcata aacacatttg aaattgagta ttgttttgca ttgtatggag    5040
ctatgttttg ctgtatcctc agaaaaaaag tttgttataa agcattcaca cccataaaaa    5100
gatagattta atattccag  ctataggaaa gaaagtgcgt ctgctcttca ctctagtctc    5160
agttggctcc ttcacatgca tgcttcttta tttctcctat tttgtcaaga aaataatagg    5220
tcacgtcttg ttctcactta tgtcctgcct agcatggctc agatgcacgt tgtagataca    5280
agaaggatca aatgaaacag acttctggtc tgttactaca accatagtaa taagcacact    5340
aactaataat tgctaattat gttttccatc tctaaggttc ccacattttt ctgttttctt    5400
aaagatccca ttatctggtt gtaactgaag ctcaatggaa catgagcaat atttcccagt    5460
cttctctccc atccaacagt cctgatggat tagcagaaca ggcagaaaac acattgttac    5520
ccagaattaa aaactaatat ttgctctcca ttcaatccaa aatggaccta ttgaaactaa    5580
aatctaaccc aatcccatta atgatttct  atggcgtcaa aggtcaaact tctgaaggga    5640
acctgtgggt gggtcacaat tcaggctata tattccccag ggctcagcca gtggatcaac    5700
atacagctag aaagctgtat tgcctttagc actcaagctc aaaagacaac tcagagttca    5760
ccatgggctc catcggcgca gcaagcatgg aattttgttt tgatgtattc aaggagctca    5820
aagtccacca tgccaatgag aacatcttct actgccccat tgccatcatg tcagctctag    5880
ccatggtata cctgggtgca aaagacagca ccaggacaca gataaataag gttgttcgct    5940
ttgataaact tccaggattc ggagacagta ttgaagctca gtgtggcaca tctgtaaacg    6000
ttcactcttc acttagagac atcctcaacc aaatcaccaa accaaatgat gtttattcgt    6060
```

```
tcagccttgc cagtagactt tatgctgaag agagataccc aatcctgcca gaatacttgc    6120
agtgtgtgaa ggaactgtat agaggaggct tggaacctat caactttcaa acagctgcag    6180
atcaagccag agagctcatc aattcctggg tagaaagtca gacaaatgga attatcagaa    6240
atgtccttca gccaagctcc gtggattctc aaactgcaat ggttctggtt aatgccattg    6300
tcttcaaagg actgtgggag aaaacattta aggatgaaga cacacaagca atgcctttca    6360
gagtgactga gcaagaaagc aaacctgtgc agatgatgta ccagattggt ttatttagag    6420
tggcatcaat ggcttctgag aaaatgaaga tcctggagct tccatttgcc agtgggacaa    6480
tgagcatgtt ggtgctgttg cctgatgaag tctcaggcct tgagcagctt gagagtataa    6540
tcaactttga aaaactgact gaatggacca gttctaatgt tatggaagag aggaagatca    6600
aagtgtactt acctcgcatg aagatggagg aaaaatacaa cctcacatct gtcttaatgg    6660
ctatgggcat tactgacgtg tttagctctt cagccaatct gtctggcatc tcctcagcag    6720
agagcctgaa gatatctcaa gctgtccatg cagcacatgc agaaatcaat gaagcaggca    6780
gagaggtggt agggtcagca gaggctggag tggatgctgc aagcgtctct gaagaattta    6840
gggctgacca tccattcctc ttctgtatca agcacatcgc aaccaacgcc gttctcttct    6900
ttggcagatg tgtttctccg cggccagcag atgacgcacc agcagatgac gcaccagcag    6960
atgacgcacc agcagatgac gcaccagcag atgacgcacc agcagatgac gcaacaacat    7020
gtatcctgaa aggctcttgt ggctggatcg gcctgctgga tgacgatgac aaatttgtga    7080
accaacacct gtgcggctca cacctggtgg aagctctcta cctagtgtgc ggggaacgag    7140
gcttcttcta cacacccaag acccgccggg aggcagagga cctgcaggtg gggcaggtgg    7200
agctgggcgg gggccctggt gcaggcagcc tgcagccctt ggccctggag gggtccctgc    7260
agaagcgtgg cattgtggaa caatgctgta ccagcatctg ctccctctac cagctggaga    7320
actactgcaa ctagggcgcc taagggcga attatcgcgg ccgctctaga ccaggcgcct    7380
ggatccagat cacttctggc taataaaaga tcagagctct agagatctgt gtgttggttt    7440
tttgtggatc tgctgtgcct tctagttgcc agccatctgt tgtttgcccc tcccccgtgc    7500
cttccttgac cctggaaggt gccactccca ctgtcctttc ctaataaaat gaggaaattg    7560
catcgcattg tctgagtagg tgtcattcta ttctgggggg tggggtgggg cagcacagca    7620
agggggagga ttgggaagac aatagcaggc atgctgggga tgcggtgggc tctatgggta    7680
cctctctctc tctctctctc tctctctctc tctctctctc tcggtacctc tctcgagggg    7740
gggcccggta cccaattcgc cctatagtga gtcgtattac gcgcgctcac tggccgtcgt    7800
tttacaacgt cgtgactggg aaaaccctgg cgttacccaa cttaatcgcc ttgcagcaca    7860
tccccctttc gccagctggc gtaatagcga agaggcccgc accgatcgcc cttcccaaca    7920
gttgcgcagc ctgaatggcg aatggaaatt gtaagcgtta atattttgtt aaaattcgcg    7980
ttaaattttt gttaaatcag ctcatttttt aaccaatagg ccgaaatcgg caaaatccct    8040
tataaatcaa agaatagac cgagataggg ttgagtgttg ttccagtttg gaacaagagt    8100
ccactattaa agaacgtgga ctccaacgtc aaagggcgaa aaaccgtcta tcagggcgat    8160
ggcccactac tccgggatca tatgacaaga tgtgtatcca ccttaactta atgattttta    8220
ccaaaatcat taggggattc atcagtgctc agggtcaacg agaattaaca ttccgtcagg    8280
aaagcttatg atgatgatgt gcttaaaaac ttactcaatg gctggttatg catatcgcaa    8340
tacatgcgaa aaacctaaaa gagcttgccg ataaaaaagg ccaatttatt gctatttacc    8400
gcggcttttt attgagcttg aaagataaat aaaatagata ggttttattt gaagctaaat    8460
```

| | |
|---|---|
| cttctttatc gtaaaaaatg ccctcttggg ttatcaagag ggtcattata tttcgcggaa | 8520 |
| taacatcatt tggtgacgaa ataactaagc acttgtctcc tgtttactcc cctgagcttg | 8580 |
| aggggttaac atgaaggtca tcgatagcag gataataata cagtaaaacg ctaaaccaat | 8640 |
| aatccaaatc cagccatccc aaattggtag tgaatgatta taaataacag caaacagtaa | 8700 |
| tgggccaata acaccggttg cattggtaag gctcaccaat aatccctgta aagcaccttg | 8760 |
| ctgatgactc tttgtttgga tagacatcac tccctgtaat gcaggtaaag cgatcccacc | 8820 |
| accagccaat aaaattaaaa cagggaaaac taaccaacct tcagatataa acgctaaaaa | 8880 |
| ggcaaatgca ctactatctg caataaatcc gagcagtact gccgtttttt cgcccattta | 8940 |
| gtggctattc ttcctgccac aaaggcttgg aatactgagt gtaaaagacc aagacccgta | 9000 |
| atgaaaagcc aaccatcatg ctattcatca tcacgatttc tgtaatagca ccacaccgtg | 9060 |
| ctggattggc tatcaatgcg ctgaaataat aatcaacaaa tggcatcgtt aaataagtga | 9120 |
| tgtataccga tcagcttttg ttcccttag tgagggttaa ttgcgcgctt ggcgtaatca | 9180 |
| tggtcatagc tgtttcctgt gtgaaattgt tatccgctca caattccaca caacatacga | 9240 |
| gccgaagca taaagtgtaa agcctggggt gcctaatgag tgagctaact cacattaatt | 9300 |
| gcgttgcgct cactgcccgc tttccagtcg ggaaacctgt cgtgccagct gcattaatga | 9360 |
| atcggccaac gcgcggggag aggcggtttg cgtattgggc gctcttccgc ttcctcgctc | 9420 |
| actgactcgc tgcgctcggt cgttcggctg cggcgagcgg tatcagctca ctcaaaggcg | 9480 |
| gtaatacggt tatccacaga atcagggggat aacgcaggaa agaacatgtg agcaaaaggc | 9540 |
| cagcaaaagg ccaggaaccg taaaaaggcc gcgttgctgg cgtttttcca taggctccgc | 9600 |
| cccctgacg agcatcacaa aaatcgacgc tcaagtcaga ggtggcgaaa cccgacagga | 9660 |
| ctataaagat accaggcgtt tccccctgga agctccctcg tgcgctctcc tgttccgacc | 9720 |
| ctgccgctta ccggatacct gtccgccttt ctcccttcgg gaagcgtggc gctttctcat | 9780 |
| agctcacgct gtaggtatct cagttcggtg taggtcgttc gctccaagct gggctgtgtg | 9840 |
| cacgaaccc ccgttcagcc cgaccgctgc gccttatccg gtaactatcg tcttgagtcc | 9900 |
| aacccggtaa gacacgactt atcgccactg gcagcagcca ctggtaacag gattagcaga | 9960 |
| gcgaggtatg taggcggtgc tacagagttc ttgaagtggt ggcctaacta cggctacact | 10020 |
| agaaggacag tatttggtat ctgcgctctg ctgaagccag ttaccttcgg aaaaagagtt | 10080 |
| ggtagctctt gatccggcaa acaaaccacc gctggtagcg gtggtttttt tgtttgcaag | 10140 |
| cagcagatta cgcgcagaaa aaaaggatct caagaagatc ctttgatctt ttctacgggg | 10200 |
| tctgacgctc agtggaacga aaactcacgt taagggattt tggtcatgag attatcaaaa | 10260 |
| aggatcttca cctagatcct tttaaattaa aaatgaagtt ttaaatcaat ctaaagtata | 10320 |
| tatgagtaaa cttggtctga cagttaccaa tgcttaatca gtgaggcacc tatctcagcg | 10380 |
| atctgtctat ttcgttcatc catagttgcc tgactccccg tcgtgtagat aactacgata | 10440 |
| cgggagggct taccatctgg ccccagtgct gcaatgatac cgcgagaccc acgctcaccg | 10500 |
| gctccagatt tatcagcaat aaaccagcca gccggaaggg ccgagcgcag aagtggtcct | 10560 |
| gcaactttat ccgcctccat ccagtctatt aattgttgcc gggaagctag agtaagtagt | 10620 |
| tcgccagtta atagtttgcg caacgttgtt gccattgcta caggcatcgt ggtgtcacgc | 10680 |
| tcgtcgtttg gtatggcttc attcagctcc ggttcccaac gatcaaggcg agttacatga | 10740 |
| tcccccatgt tgtgcaaaaa agcggttagc tccttcggtc ctccgatcgt tgtcagaagt | 10800 |
| aagttggccg cagtgttatc actcatggtt atggcagcac tgcataattc tcttactgtc | 10860 |

```
-continued atgccatccg taagatgctt ttctgtgact ggtgagtact caaccaagtc attctgagaa  10920
tagtgtatgc ggcgaccgag ttgctcttgc ccggcgtcaa tacgggataa taccgcgcca  10980
catagcagaa ctttaaaagt gctcatcatt ggaaaacgtt cttcggggcg aaaactctca  11040
aggatcttac cgctgttgag atccagttcg atgtaaccca ctcgtgcacc caactgatct  11100
tcagcatctt ttactttcac cagcgtttct gggtgagcaa aaacaggaag gcaaaatgcc  11160
gcaaaaaagg gaataagggc gacacggaaa tgttgaatac tcatactctt ccttttttcaa 11220 tattattgaa gcatttatca gggttattgt ctcatgagcg gatacatatt tgaatgtatt  11280
tagaaaaata aacaaatagg ggttccgcgc acatttcccc gaaaagtgcc ac           11332

<210> SEQ ID NO 50
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(36)
<223> OTHER INFORMATION: Maximum number of repeating GPGG units provided
      by SEQ ID NO: 32
<220> FEATURE:
<221> NAME/KEY: REPEAT
<222> LOCATION: (1)..(36)
<223> OTHER INFORMATION: Maximum number of 9 repeating GPGG units
      provided by SEQ ID NO: 32

<400> SEQUENCE: 50

Gly Pro Gly Gly Gly Pro Gly Gly Gly Pro Gly Gly Gly Pro Gly Gly
1               5                   10                  15

Gly Pro Gly Gly Gly Pro Gly Gly Gly Pro Gly Gly Gly Pro Gly Gly
            20                  25                  30

Gly Pro Gly Gly
        35
```

GENE THERAPY USING TRANSPOSON-BASED VECTORS

CROSS REFERENCE TO RELATED APPLICATIONS

This application is the U.S. National Phase of PCT/US2004/043092, filed on Dec. 24, 2004, which claims priority to U.S. Provisional Patent Application No. 60/532,504 filed on Dec. 24, 2003, U.S. Provisional Patent Application No. 60/565,371 filed on Apr. 26, 2004, and U.S. Provisional Patent Application No. 60/592,098 filed on Jul. 28, 2004, the contents of which are incorporated by reference herein.

FIELD OF THE INVENTION

The present invention relates generally to use of transposon-based vectors in the preparation of a medicament useful for providing therapy, including gene therapy, to animals and humans following administration of the medicament. The vectors of the present invention may be directed to specific tissues, organs and cells where a selected gene is stably incorporated and produces proteins, peptides or nucleic acids which have a therapeutic effect in the animal or human.

BACKGROUND OF THE INVENTION

Improved gene delivery technologies are needed for the treatment of disease in animals. Many diseases and conditions can be treated with gene-delivery technologies, which provide a gene of interest to an animal suffering from the disease or the condition. An example of such disease is Type 1 diabetes. Type 1 diabetes is an autoimmune disease that ultimately results in destruction of the insulin producing β-cells in the pancreas. Although animals with Type 1 diabetes may be treated adequately with insulin injections or insulin pumps, these therapies are only partially effective. In addition, hyper- and hypoglycemia occurs frequently despite intensive home blood glucose monitoring. Finally, careful dietary constraints are needed to maintain an adequate ratio of calories consumed. Development of gene therapies providing delivery of the insulin gene into the pancreas of diabetic animals could overcome many of these problems and result in improved life expectancy and quality of life.

Several of the prior art gene delivery technologies employed viruses that are associated with potentially undesirable side effects and safety concerns. The majority of current gene-delivery technologies useful for gene therapy rely on virus-based delivery vectors, such as adeno and adeno-associated viruses, retroviruses, and other viruses, which have been attenuated to no longer replicate. (Kay, M. A., et al. 2001. Nature Medicine 7:33-40).

There are multiple problems associated with the use of viral vectors. First, they are not tissue-specific. In fact, a gene therapy trial using adenovirus was recently halted because the vector was present in a patient's sperm (Gene trial to proceed despite fears that therapy could change child's genetic makeup. The New York Times, Dec. 23, 2001). Second, viral vectors are likely to be transiently incorporated, which necessitates re-treating a patient at specified time intervals. (Kay, M. A., et al. 2001. Nature Medicine 7:33-40). Third, there is a concern that a viral-based vector could revert to its virulent form and cause disease. Fourth, viral-based vectors require a dividing cell for stable integration. Fifth, viral-based vectors indiscriminately integrate into various cells, which can result in undesirable germline integration. Sixth, the required high titers needed to achieve the desired effect have resulted in the death of one patient and they are believed to be responsible for induction of cancer in a separate study. (Science, News of the Week, Oct. 4, 2002).

Accordingly, what is needed is a new method to produce transgenic animals and humans with stably incorporated genes, in which the vector containing those genes does not cause disease or other unwanted side effects. There is also a need for DNA constructs that would be stably incorporated into the tissues and cells of animals and humans, including cells in the resting state that are not replicating. There is a further recognized need in the art for DNA constructs capable of delivering genes to specific tissues and cells of animals and humans and for producing proteins in those animals and humans.

When incorporating a gene of interest into an animal or human for the production of a desired protein or when incorporating a gene of interest in an animal for the treatment of a disease, it is often desirable to selectively activate incorporated genes using inducible promoters. These inducible promoters are regulated by substances either produced or recognized by the transcription control elements within the cell in which the gene is incorporated. In many instances, control of gene expression is desired in transgenic animals and humans so that incorporated genes are selectively activated at desired times and/or under the influence of specific substances. Accordingly, what is needed is a means to selectively activate genes introduced into the genome of cells of a transgenic animal or human. This can be taken a step further to cause incorporation to be cell-specific, which prevents widespread gene incorporation throughout the body. This decreases the amount of DNA needed for a treatment, decreases the chance of incorporation in gametes, and targets gene delivery, incorporation, and expression to the desired tissue where the gene is needed to function.

RNAi has been targeted as a tool for several uses including treatment of genetic abnormalities and disease, cancer, and development. There are mainly two types of short RNAs that target complementary messengers in animals: small interfering RNAs and micro-RNAs. Both are produced by the cleavage of double-stranded RNA precursors by Dicer, a member of the Rnase III family of double-stranded specific endonucleases, and both guide the RNA-induced silencing complex to cleave specifically RNAs sharing sequence identity with them. RNAi technology can be used in therapeutic approaches to treat disease and various conditions. However, a major drawback to RNAi therapy has been the lack of a reliable delivery method of the short RNA sequences. Most researchers working in the field rely on producing short double stranded RNA (dsRNA) in the laboratory and then delivering these short dsRNAs either by direct injection, electroporation, by complexing with a transfecting reagent, etc. The result is gene silencing, but only as long as the dsRNA remains present in the cell, which generally begins to decrease after about 20 h. In order to obtain lasting therapeutic effects, the RNAi sequence must be expressed long term, preferably under a constitutive promoter. In order to accomplish RNAi expression in a plasmid-based vector and subsequent recognition by RNA induced silencing complex (RISC), the RNA must be double stranded. To obtain dsRNA from a vector, it must be expressed as a short hairpin RNA (shRNA), in which there is a sense strand, a hairpin loop region and an antisense strand (M. Izquierdo. 2004. Short interfering RNAs as a tool for cancer gene therapy. Cancer Gene Therapy pp 1-11; Miyagishi et al. 2004. J Gene Med 6:715-723). The hairpin region allows the antisense strand to loop back and bind to the complimentary sense strand.

SUMMARY OF THE INVENTION

The present invention addresses the problems described above by providing new, effective and efficient compositions comprising transposon-based vectors for providing therapy, including gene therapy, to animals and humans. The present invention provides methods of using these compositions for providing therapy to animals and humans. These transposon-based vectors are used in the preparation of a medicament useful for providing a desired effect to a recipient following administration. Gene therapy includes, but is not limited to, introduction of a gene into an animal using a transposon-based vector. Such genes are called exogenous genes although it is to be understood that these genes may also be found in the recipient animal. These genes may serve a variety of functions in the recipient such as coding for the production of nucleic acids, for example RNA, or coding for the production of proteins and peptides. An advantage of the present invention is that transgenic animals are produced with higher efficiencies than observed in the prior art, including efficient incorporation of large polynucleotide sequences. The present invention facilitates efficient incorporation of the polynucleotide sequences, including the genes of interest, promoters, insertion sequences and poly A, with transfection efficiencies of at least 30%. Transfection efficiencies greater than 30%, 40%, 50%. 60% and 70% have been observed.

Transgenic animals further include but are not limited to avians, fish, amphibians, reptiles, insects, and mammals. It is to be understood that humans are encompassed within the term "animal" and the term "mammal" in the present application. In another embodiment, the animal is a milk-producing animal, including but not limited to bovine, porcine, ovine and equine animals. Transgenic animals include all egg-laying animals and milk-producing animals. In one embodiment, the animal is an avian animal. In another embodiment, the animal is a mammal. Preferred animals may be pets, domestic animals, exotic animals, zoo animals, wild animals or any other type of animal in need of gene therapy. Animals are made transgenic through administration of a composition comprising a transposon-based vector designed for stable incorporation of a gene of interest for production of a desired protein, peptide or nucleic acid, together with an acceptable carrier.

The present invention addresses the problems described above by providing methods and compositions comprising transposon-based vectors for stable incorporation of an exogenous gene into a specific cell or tissue of an animal. It is to be understood that the terms cell-specific and tissue-specific are often used interchangeably by those of ordinary skill in the art. In the present application, cell-specific promoters indicate a promoter that is active in that cell. A promoter may be used to drive the transposase that may or may not drive the desired target protein. For example, a vitellogenin promoter or a glucose-6-phosphatase promoter (both promoters being found in hepatocytes) may be used to direct incorporation of the gene into the liver, but the promoter driving the target gene/protein, may be constitutive, cell-specific, or be induced by a hormone, antibiotic, etc., that is not specific to a hepatocyte.

In one embodiment of the present invention, the transposon-based vectors are designed for cell-specific gene expression, for example, by placing a selected gene under control of a cell-specific promoter, which further increases cell or tissue specificity of expression of the selected gene. In one embodiment of the present invention, the vectors are used for gene therapy of animals or humans, wherein the expression of the selected gene has a therapeutic effect on a cell or a tissue in which it is specifically incorporated, expressed, or both. The expression of the selected gene may also have a therapeutic effect on other cells or tissues, particularly when the expressed protein is secreted from the cell and can access other cells. In another embodiment, the vectors are used to integrate a desired gene into specific cells of an animal for production of biologic agents encoded by the gene of interest.

This invention provides polynucleotide cassettes or vectors containing at least one gene of interest and at least one pro polynucleotide sequences, wherein the at least one gene of interest is operably-linked to a pro nucleotide sequence. Each of the at least one gene of interest encodes a polypeptide. This invention also provides polynucleotide cassettes containing two or more genes of interest and two or more pro polynucleotide sequences, wherein each gene of interest is operably-linked to a pro nucleotide sequence. Each of the genes of interest encodes a polypeptide that forms a part of the multimeric protein. One discovery of the present invention is the use of pro portions of prepro signal sequences to facilitate appropriate processing, expression, and/or formation of multimeric proteins in an individual. Several examples of prepro polynucleotides from which a pro polynucleotide can be derived or be a part of are a cecropin prepro, lysozyme prepro, ovomucin prepro, ovotransferrin prepro, a signal peptide for tumor necrosis factor receptor (SEQ ID NO:1). Signal sequences for protein secretion are readily available through databases such as GenBank or the literature. Signal sequences for protein secretion can be identified by one of ordinary skill in the art, for example through comparison of mRNA to mature protein and identification of the sequence removed from the secreted protein. The prepro or pro polynucleotide can be a cecropin prepro or pro polynucleotide selected from the group consisting of cecropin A1, cecropin A2, cecropin B, cecropin C, cecropin D, cecropin E and cecropin F. In a preferred embodiment, the pro polynucleotide is a cecropin B pro polynucleotide having a sequence shown in SEQ ID NO:2 or SEQ ID NO:3. A preferred prepro polynucleotide is a cecropin B polynucleotide having a sequence shown in SEQ ID NO:4 or SEQ ID NO:5.

Another discovery of the present invention is that cecropin prepro sequences facilitate appropriate processing, expression, and/or formation of proteins, including multimeric proteins, in an individual. Accordingly, the present invention includes polynucleotide cassettes containing one or more genes of interest operably-linked to a cecropin prepro sequence. In one embodiment, the polynucleotide cassette contains two or more genes of interest operably-linked to a cecropin prepro sequence. Preferred cecropin prepro polynucleotides are provided in SEQ ID NO:4 and SEQ ID NO:5. The present invention also includes polynucleotide cassettes containing two or more genes of interest operably linked to a cecropin prepro polynucleotide, wherein pro sequences are located between the genes of interest.

These polynucleotide cassettes are administered to an individual for expression of polypeptide sequences and the formation of a protein or a multimeric protein.

In another embodiment of the present invention, the gene of interest incorporated into the cell is expressed and the resulting protein or peptide has regulatory properties affecting a function of the cell or tissue in which it is expressed.

In a further embodiment, the gene of interest incorporated into the cell is expressed, secreted and affects another cell.

In another embodiment of the present invention, the gene of interest incorporated into the cell is expressed as an inhibitory molecule, such as an RNAi may regulate the expression or overexpression of another substance.

Cell or tissue-specific expression of a gene of interest may be particularly advantageous because of the possible toxic or otherwise potentially negative effects of the gene of interest if it were expressed in an undesirable location. Control of expression in the desired cell or tissue is achieved by operably linking the gene of interest to a cell or tissue specific regulator.

In yet another embodiment of the present invention, the expression of the exogenous gene is blocked unless an animal is at a selected stage in its life cycle. For example, expression of an exogenous gene may not be desirable until an animal reaches puberty. In this embodiment, the expression of the exogenous gene is controlled by a promoter, which is activated specifically at the desired stage in the life of the animal. Alternatively, expression of an exogenous gene may not be desirable until a disease process begins or at a time when a substance, such as a hormone or an inflammatory molecule, is found in undesirable levels.

In yet another embodiment of the present invention, the expression of the exogenous gene is blocked unless an animal produces a substance. For example, expression of an exogenous gene may not be desirable until an animal begins producing cancer-related molecules. In this embodiment, the expression of the exogenous gene is controlled by a promoter, which is activated specifically by the cancer-related molecules. Such gene therapy fights the disease process at very early stages.

An additional advantage of the present invention is that a disease or a condition can be treated in a specific organ or tissue of an animal without risk of making other organs or tissues transgenic. This is particularly useful when concerns exist about passing a transgene to the progeny of the transgenic animal, or contaminating the environment with the transgene shed by the animal. The methods and compositions of the present invention are particularly advantageous in applications where germline integration of exogenous DNA is undesirable.

The compositions of the present invention may be introduced into an animal through any route of administration that serves to deliver the composition to the desired organs, tissues and cells. Such routes of administration include, but are not limited to, oral and parenteral routes such as intravascular, intravenous, intraarterial, intracardiac, intraperitoneal, intramuscular, anal, intracerebrovascular, intracerebroventricular, cutaneous, intradermal, subcutaneous, transdermal, into any duct system, into any cavity or space, such as the abdominopelvic, pleural, pericardial, peritoneal cavities or spaces, intrathecal, or into the respiratory system, the urinary system, the gastrointestinal system, the nervous system, the lymphatic system, the immune system, the reproductive system and the endocrine system.

Administration of the transposon based vectors into the cardiovascular system achieves rapid distribution throughout the animal to reach target tissues and cells receiving blood supply. Such administration may be into any chamber of the heart, for example into the left ventricle, the right ventricle, or the atrial chambers, for rapid distribution into the systemic circulation or the pulmonary circulation. The vectors may be administered into selected vessels, such as the cardiac vessels, into the aorta or into a selected vessel leading to a targeted group of cells, a tissue, an organ or a tumor. Administration into the left side of the heart may target the systemic circulation through the aorta and any of its branches, including but not limited to the coronary vessels, the ovarian or testicular arteries, the renal arteries, the arteries supplying the gastrointestinal and pelvic tissues, including the celiac, cranial mesenteric and caudal mesenteric vessels and their branches, the common iliac arteries and their branches to the pelvic organs, the gastrointestinal system and the lower extremity, the carotid, brachiocephalic and subclavian arteries. It is to be understood that the specific names of blood vessels change with the species under consideration and are known to one of ordinary skill in the art. Administration into the left ventricle or ascending aorta supplies any of the tissues receiving blood supply from the aorta and its branches, including but not limited to the testes, ovary, oviduct, and liver. Administration may occur through any means, for example by injection into the left ventricle, or by administration through a cannula or needle introduced into the left atrium, left ventricle, aorta or a branch thereof.

The compositions of the present invention may be administered to a reproductive organ including, but not limited to, an oviduct, an ovary, the testes, seminal vesicle, any accessory organ, or into the duct system of the mammary gland. The compositions of the present invention may be administered to a reproductive organ of an animal through the cloaca. The compositions of the present invention may be directly administered to an organ or can be administered to an artery or vein leading to the organ. A transfection reagent is optionally added to the composition before administration.

The transposon-based vectors of the present invention include a transposase, operably-linked to a first promoter, and a coding sequence for a protein or peptide of interest operably-linked to a second promoter, wherein the coding sequence for the protein or peptide of interest and its operably-linked promoter are flanked by transposase insertion sequences recognized by the transposase. The transposon-based vector also includes the following characteristics: a) one or more modified Kozak sequences 3' of the first promoter to enhance expression of the transposase; b) modifications of the codons for the first several N-terminal amino acids of the transposase, wherein the nucleotide at the third base position of each codon is changed to an A or a T without changing the corresponding amino acid; c) addition of one or more stop codons to enhance the termination of transposase synthesis; and/or, d) addition of an effective polyA sequence operably-linked to the transposase to further enhance expression of the transposase gene. In some embodiments, the effective polyA sequence is an avian optimized polyA sequence.

The present invention also provides for tissue-specific incorporation and/or expression of a gene of interest. Tissue-specific stable incorporation of a gene of interest may be achieved by placing the transposase gene under the control of a tissue-specific promoter, whereas tissue-specific expression of a gene of interest may be achieved by placing the gene of interest under the control of a tissue-specific promoter. Such tissues include all tissues within the body, for example, connective tissue, muscle, bone, lymphoid tissue, and nervous tissue. In some embodiments, the gene of interest is transcribed under the influence of an ovalbumin, or other oviduct specific, promoter. In other embodiments, promoters may be specific for cells in another organ including but not limited to the liver, brain, mammary gland, any endocrine organ, and thymus.

The present invention also provides for cell-specific incorporation and/or expression of a gene of interest. Cell-specific incorporation of a gene of interest may be achieved by placing the transposase gene under the control of a cell-specific promoter, whereas tissue-specific expression of a gene of interest may be achieved by placing the gene of interest under the control of a cell-specific promoter. Such promoters may include promoters specific for cells such as neurons, glia, hepatocytes, epithelial cells, cells of the immune system, fibroblasts, chondrocytes, synovial cells, osteoblasts, osteocytes, osteoclasts, muscle cells (including striated, smooth and cardiac muscle cells), granulocytes, lymphocytes, T lymphocytes, B-lymphocytes, thymocytes, germ bells, blast cells, cancerous cells, endocrine cells, white blood cells, pancreatic islet cells, acinar cells, splenocytes, follicular cells, and so on. Cell specific promoters are known to one of ordinary skill in the art.

The present invention advantageously produces a high number of transgenic animals having a gene of interest stably incorporated. In some embodiments wherein the transposon-based vector is administered to the ovary or the testes, these transgenic animals successfully pass the desired gene to their progeny. Accordingly, the present invention can be used to obtain transgenic animals having the gene of interest incorporated into the germline through transfection of the ovary or testes. These transgenic animals of the present invention produce large amounts of a desired molecule encoded by the transgene. Such germline transmission can produce generations of animals containing the desired gene. Such a gene may be useful in providing gene therapy to animals known to be susceptible to specific conditions, for example an immune deficiency or arthritis.

Gene therapy of cells other than germline cells may also be achieved by introducing the transposon-based vectors to these cells for stable incorporation of exogenous genes.

Any desired gene may be incorporated into the novel transposon-based vectors of the present invention in order to synthesize a desired molecule in the transgenic animals to provide gene therapy. Proteins, peptides and nucleic acids are preferred desired molecules to be produced by the transgenic animals of the present invention. In order to provide gene therapy to an animal, the gene desired to produce a desired molecule in the transgenic animal is selected and inserted into the transposon-based vectors of the present invention.

Nucleic acids may be made by the transgenic animals. Such nucleic acids include, but are not limited to, single stranded DNA, RNA, antisense nucleic acids, siRNA, and polynucleotide strands that affect cellular function. Some of these nucleic acids may affect cellular function by modulating transcription of a gene, for example by inhibiting the function of the gene which may be producing undesirable effects such as inappropriate amounts of molecules or molecules that may be deleterious to the animal.

Genes may be regulated by regulating a specific transcription factor. Cystic fibrosis, for example, is the result of a mutant protein. Even if RNAi is used, the cell is still synthesizing mutant RNA. However, if the transcription factor allowing expression of the mutant protein is blocked, then the mutant gene is shut down and the normal gene can be expressed under a different promoter.

A wide range of recombinant peptides and proteins can be produced in animals receiving the gene therapy of the present invention. Enzymes, hormones, antibodies, growth factors, serum proteins, commodity proteins, fusion proteins, fusion peptides, biological response modifiers, cytokines, chemoattractants, chemorepellents, receptor agonists, receptor antagonists, peptides and designed proteins may all be made through practice of the present invention.

Accordingly, it is an object of the present invention to provide novel transposon-based vectors useful in providing gene therapy to an animal.

It is an object of the present invention to provide novel transposon-based vectors for use in the preparation of a medicament useful in providing gene therapy to an animal or human.

It is another object of the present invention to provide novel transposon-based vectors that encode for the production of desired proteins or peptides in cells.

Yet another object of the present invention to provide novel transposon-based vectors that encode for the production of desired nucleic acids in cells.

It is a further object of the present invention to provide methods for cell and tissue specific incorporation of transposon-based DNA constructs comprising targeting a selected gene to a specific cell or tissue of an animal.

It is yet another object of the present invention to provide methods for cell and tissue specific expression of transposon-based DNA constructs comprising designing a DNA construct with cell specific promoters that enhance stable incorporation of the selected gene by the transposase and expressing the selected gene in the cell.

It is an object of the present invention to provide gene therapy for generations through germ line administration of a transposon-based vector.

Another object of the present invention is to provide gene therapy in animals through non germ line administration of a transposon-based vector.

It is further an object of the present invention to provide a method to produce transgenic animals through intraovarian or intratesticular administration of a transposon-based vector that are capable of producing transgenic progeny.

It is further an object of the present invention to provide a method to produce transgenic animals through cardiovascular administration of a transposon-based vector.

Another object of the present invention is to provide gene therapy in animals through administration of a transposon-based vector, wherein the animals produce desired proteins, peptides or nucleic acids.

Yet another object of the present invention is to provide gene therapy in animals through administration of a transposon-based vector, wherein the animals produce desired proteins or peptides that are recognized by receptors on target cells.

Still another object of the present invention is to provide gene therapy in animals through administration of a transposon-based vector, wherein the animals produce desired fusion proteins or fusion peptides, a portion of which are recognized by receptors on target cells, in order to deliver the other protein or peptide component of the fusion protein or fusion peptide to the cell to induce a biological response.

Yet another object of the present invention is to provide a method for gene therapy of animals through administration of transposon-based vectors comprising tissue specific promoters and a gene of interest to facilitate tissue specific incorporation and expression of a gene of interest to produce a desired protein, peptide or nucleic acid.

Another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid.

Still another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid, wherein the desired protein, peptide or nucleic acid has a desired biological effect in the animal.

Another object of the present invention is to provide transgenic animals that contain a stably incorporated transgene.

An advantage of the present invention is that transgenic animals are produced with higher efficiencies than observed in the prior art.

Another advantage of the present invention is that transgenic animals are produced with higher efficiencies than observed in the prior art, including large transgenes.

Another advantage of the present invention is that these transgenic animals possess high copy numbers of the transgene.

Another advantage of the present invention is that the transgenic animals produce large amounts of desired molecules encoded by the transgene.

Still another advantage of the present invention is that desired molecules are produced by the transgenic animals much more efficiently and economically than prior art methods, thereby providing a means for efficient gene therapy.

Yet another advantage of the present invention is that the desired proteins and peptides are produced rapidly after making animals transgenic through introduction of the vectors of the present invention.

These and other objects, features and advantages of the present invention will become apparent after a review of the following detailed description of the disclosed embodiments and claims.

BRIEF DESCRIPTION OF THE FIGURES

FIG. 4 depicts schematically a transposon based-vector for expression of an RNAi molecule. "Tet$_i$ pro" indicates a tetracycline inducible promoter whereas "pro" indicates the pro portion of a prepro sequence as described herein. "Ovgen" indicates approximately 60 base pairs of an ovalbumin gene, "Ovotrans" indicates approximately 60 base pairs of an ovotransferring gene and "Ovomucin" indicates approximately 60 base pairs of an ovomucin gene.

DETAILED DESCRIPTION OF THE INVENTION

Figure 1:
FIG. 1 depicts schematically a transposon-based vector containing a transposase operably linked to a first promoter and a gene of interest and poly A operably-linked to a second promoter, wherein the gene of interest and its operably-linked promoter are flanked by insertion sequences (IS) recognized by the transposase. "Pro" designates a promoter. In this and subsequent figures, the size of the actual nucleotide sequence is not necessarily proportionate to the box representing that sequence.

The present invention provides a new, effective and efficient method of providing gene therapy to animals through administration of a composition comprising a transposon-based vector designed for incorporation of a gene of interest and production of a desired molecule. These transposon-based vectors are used in the preparation of a medicament for administration to an animal or human to provide a beneficial effect in the recipient through production of a desired molecule. The present invention facilitates efficient incorporation of the polynucleotide sequences, including the genes of interest, promoters, insertion sequences and poly A, with transfection efficiencies of at least 30%. Transfection efficiencies greater than 30%, 40%, 50%, 60% and 70% have been observed. Desired molecules encoded by genes of interest include, but are not limited to, nucleic acids, proteins and peptides. Proteins include multimeric proteins. Multimeric proteins include associated multimeric proteins (two or more associated polypeptides) and multivalent multimeric proteins (a single polypeptide encoded by more than one gene of interest). Expression and/or formation of the multimeric protein in the individual is achieved by administering a polynucleotide cassette containing the genes of interest to the individual. The polynucleotide cassette may additionally contain one or more pro sequences, prepro sequences, cecropin prepro sequences, and/or cleavage site sequences. In a preferred embodiment, the polynucleotide cassette is administered through the vascular system. Nucleic acids that may be produced in transfected cells include single stranded DNA, RNA, antisense nucleic acids, siRNA, and polynucleotide strands that affect cellular function.

Definitions

It is to be understood that as used in the specification and in the claims, "a" or "an" can mean one or more, depending upon the context in which it is used. Thus, for example, reference to "a cell" can mean that at least one cell can be utilized.

The term "animal" includes a human in the present application.

The term "protein" includes multimeric protein" as described in PCT US03/41261. Multimeric proteins include associated multimeric proteins (two or more associated polypeptides) and multivalent multimeric proteins (a single polypeptide encoded by more than one gene of interest).

The term "nucleic acid" includes double stranded DNA, single stranded DNA, RNA, antisense nucleic acids, siRNA, and polynucleotide strands.

The term "antibody" is used interchangeably with the term "immunoglobulin" and is defined herein as a protein synthesized by an animal or a cell of the immune system in response to the presence of a foreign substance commonly referred to as an "antigen" or an "immunogen". The term antibody includes fragments of antibodies. Antibodies are characterized by specific affinity to a site on the antigen, wherein the site is referred to an "antigenic determinant" or an "epitope". Antigens can be naturally occurring or artificially engineered. Artificially engineered antigens include, but are not limited to, small molecules, such as small peptides, attached to haptens such as macromolecules, for example proteins, nucleic acids, or polysaccharides. Artificially designed or engineered variants of naturally occurring antibodies and artificially designed or engineered antibodies not occurring in nature are all included in the current definition. Such variants include conservatively substituted amino acids and other forms of substitution as described in the section concerning proteins and polypeptides.

The present invention provides novel transposon-based vectors and their use for specific and stable incorporation of a gene of interest into a specific cell to stably incorporate the gene.

The term "gene" is defined herein to include a coding region for a protein, peptide or polypeptide.

The term "transgenic animal" refers to an animal having at least a portion of the transposon-based vector DNA is incorporated into its DNA. While a transgenic animal includes an animal wherein the transposon-based vector DNA is incorporated into the germline DNA, a transgenic animal also includes an animal having DNA in one or more cells that contain a portion of the transposon-based vector DNA for any period of time. In a preferred embodiment, a portion of the transposon-based vector comprises a gene of interest. More preferably, the gene of interest is incorporated into the animal's DNA for a period of at least a few days, preferably the reproductive life of the animal, and preferably the life of the animal.

The term "vector" is used interchangeably with the terms "construct", "DNA construct", "genetic construct", and "polynucleotide cassette" to denote synthetic nucleotide sequences used for manipulation of genetic material, including but not limited to cloning, subcloning, sequencing, or introduction of exogenous genetic material into cells, tissues or organisms, such as animals. It is understood by one skilled in the art that vectors may contain synthetic DNA sequences, naturally occurring DNA sequences, or both. The vectors of the present invention are transposon-based vectors as described herein.

When referring to two nucleotide sequences, one being a regulatory sequence, the term "operably-linked" is defined herein to mean that the two sequences are associated in a manner that allows the regulatory sequence to affect expression of the other nucleotide sequence. It is not required that the operably-linked sequences be directly adjacent to one another with no intervening sequence(s).

The term "regulatory sequence" is defined herein as including promoters, enhancers and other expression control elements such as polyadenylation sequences, matrix attachment sites, insulator regions for expression of multiple genes on a single construct, ribosome entry/attachment sites, introns that are able to enhance expression, and silencers. Promoters may be cell specific or tissue specific to facilitate expression in a desired target.

Transposon-Based Vectors

While not wanting to be bound by the following statement, it is believed that the nature of the DNA construct is an important factor in successfully providing gene therapy to animals. The "standard" types of plasmid and viral vectors that have previously been almost universally used for transgenic work in all species have low efficiencies and may constitute a major reason for the low rates of transformation previously observed. The DNA (or RNA) constructs previously used often do not integrate into the host DNA, or integrate only at low frequencies. Other factors may have also played a part, such as poor entry of the vector into target cells. The present invention provides transposon-based vectors that can be administered to an animal that overcome the prior art problems relating to low transgene integration frequencies. In the present invention integration frequencies greater than 30%, 40%, 50%, 60% and also 70% are often obtained for vectors about 10 kb or less. In some cases, depending on the route of administration, integration frequencies of over 70%, 80% and even 90% are observed. If the vector is over 15 kb, then transfection rates of over 30% and over 40% are feasible. Two preferred transposon-based vectors of the present invention in which a transposase, gene of interest and other polynucleotide sequences may be introduced are termed pTnMCS (SEQ ID NO:6) and timed (SEQ ID NO:7).

The transposon-based vectors of the present invention produce integration frequencies an order of magnitude greater than has been achieved with previous vectors. More specifically, intratesticular injections performed with a prior art transposon-based vector (described in U.S. Pat. No. 5,719,055) resulted in 41% sperm positive roosters whereas intratesticular injections performed with the novel transposon-based vectors of the present invention resulted in 77% sperm positive roosters. Actual frequencies of integration were estimated by either or both comparative strength of the PCR signal from the sperm and histological evaluation of the testes and sperm by quantitative PCR.

The transposon-based vectors of the present invention include a transposase gene operably-linked to a first promoter, and a coding sequence for a desired protein or peptide operably-linked to a second promoter, wherein the coding sequence for the desired protein or peptide and its operably-linked promoter are flanked by transposase insertion sequences recognized by the transposase. The transposon-based vector also includes one or more of the following characteristics: a) one or more modified Kozak sequences comprising ACCATG (SEQ ID NO:8) 3' of the first promoter to enhance expression of the transposase; b) modifications of the codons for the first several N-terminal amino acids of the transposase, wherein the third base of each codon was changed to an A or a T without changing the corresponding amino acid; c) addition of one or more stop codons to enhance the termination of transposase synthesis; and/or, d) addition of an effective polyA sequence operably-linked to the transposase to further enhance expression of the transposase gene. The transposon-based vector may additionally or alternatively include one or more of the following Kozak sequences 3' of any promoter, including the promoter operably-linked to the transposase: ACCATGG (SEQ ID NO:9), AAGATGT (SEQ ID NO:11), ACGATGA (SEQ ID NO:12), AAGATGG (SEQ ID NO:13), GACATGA (SEQ ID NO:14), and ACCATGA (SEQ ID NO:15), ACCATGT (SEQ ID NO:16). In another embodiment, the transposon-based vector comprises an avian optimized polyA sequence and does not comprise a modified Kozak sequence.

FIG. 1 shows a schematic representation of several components of the transposon-based vector. The present invention further includes vectors containing more than one gene of interest, wherein a second or subsequent gene of interest is operably-linked to the second promoter or to a different promoter. It is also to be understood that the transposon-based vectors shown in the Figures are representative of the present invention and that the order of the vector elements may be different than that shown in the Figures, that the elements may be present in various orientations, and that the vectors may contain additional elements not shown in the Figures.

Transposases and Insertion Sequences

In a further embodiment of the present invention, the transposase found in the transposase-based vector is an altered target site (ATS) transposase and the insertion sequences are those recognized by the ATS transposase. However, the transposase located in the transposase-based vectors is not limited to a modified ATS transposase and can be derived from any transposase. Transposases known in the prior art include those found in AC7, Tn5SEQ1, Tn916, Tn951, Tn1721, Tn 2410, Tn1681, Tn1, Tn2, Tn3, Tn4, Tn5, Tn6, Tn9, Tn10, Tn30, Tn101, Tn903, Tn501, Tn1000 (γδ), Tn1681, Tn2901, AC transposons, Mp transposons, Spm transposons, En transposons, Dotted transposons, Mu transposons, Ds transposons, dSpm transposons and I transposons. According to the present invention, these transposases and their regulatory sequences are modified for improved functioning as follows: a) the addition one or more modified Kozak sequences comprising ACCATG (SEQ ID NO:8) 3' of the promoter operably-linked to the transposase; b) a change of the codons for the first several amino acids of the transposase, wherein the third base of each codon was changed to an A or a T without changing the corresponding amino acid; c) the addition of one or more stop codons to enhance the termination of transposase synthesis; and/or, d) the addition of an effective polyA sequence operably-linked to the transposase to further enhance expression of the transposase gene.

Although not wanting to be bound by the following statement, it is believed that the modifications of the first several N-terminal codons of the transposase gene increase transcription of the transposase gene, in part, by increasing strand dissociation. It is preferable that between approximately 1 and 20, more preferably 3 and 15, and most preferably between 4 and 12 of the first N-terminal codons of the transposase are modified such that the third base of each codon is changed to an A or a T without changing the encoded amino acid. In one embodiment, the first ten N-terminal codons of the transposase gene are modified in this manner. It is also preferred that the transposase contain mutations that make it less specific for preferred insertion sites and thus increases the rate of transgene insertion as discussed in U.S. Pat. No. 5,719,055.

In some embodiments, the transposon-based vectors are optimized for expression in a particular host by changing the methylation patterns of the vector DNA. For example, prokaryotic methylation may be reduced by using a methylation deficient organism for production of the transposon-based vector. The transposon-based vectors may also be methylated to resemble eukaryotic DNA for expression in a eukaryotic host.

Transposases and insertion sequences from other analogous eukaryotic transposon-based vectors that can also be modified and used are, for example, the Drosophila P element derived vectors disclosed in U.S. Pat. No. 6,291,243; the Drosophila mariner element described in Sherman et al. (1998); or the sleeping beauty transposon. See also Hackett et al. (1999); D. Lampe et al., 1999. Proc. Natl. Acad. Sci. USA, 96:11428-11433; S. Fischer et al., 2001. Proc. Natl. Acad. Sci. USA, 98:6759-6764; L. Zagoraiou et al., 2001. Proc. Natl. Acad. Sci. USA, 98:11474-11478; and D. Berg et al. (Eds.), Mobile DNA, Amer. Soc. Microbiol. (Washington, D.C., 1989). However, it should be noted that bacterial transposon-based elements are preferred, as there is less likelihood that a eukaryotic transposase in the recipient species will recognize prokaryotic insertion sequences bracketing the transgene.

Many transposases recognize different insertion sequences, and therefore, it is to be understood that a transposase-based vector will contain insertion sequences recognized by the particular transposase also found in the transposase-based vector. In a preferred embodiment of the invention, the insertion sequences have been shortened to about 70 base pairs in length as compared to those found in wild-type transposons that typically contain insertion sequences of well over 100 base pairs.

While the examples provided below incorporate a "cut and insert" Tn10 based vector that is destroyed following the insertion event, the present invention also encompasses the use of a "rolling replication" type transposon-based vector. Use of a rolling replication type transposon allows multiple copies of the transposon/transgene to be made from a single transgene construct and the copies inserted. This type of transposon-based system thereby provides for insertion of multiple copies of a transgene into a single genome. A rolling replication type transposon-based vector may be preferred when the promoter operably-linked to gene of interest is endogenous to the host cell and present in a high copy number or highly expressed. However, use of a rolling replication system may require tight control to limit the insertion events to non-lethal levels. Tn1, Tn2, Tn3, Tn4, Tn5, Tn9, Tn21, Tn501, Tn551, Tn951, Tn1721, Tn2410 and Tn2603 are examples of a rolling replication type transposon, although Tn5 could be both a rolling replication and a cut and insert type transposon.

Stop Codons and PolyA Sequences

In one embodiment, the transposon-based vector contains two stop codons operably-linked to the transposase and/or to the gene of interest. In an alternate embodiment, one stop codon of UAA or UGA is operably linked to the transposase and/or to the gene of interest. While not wanting to be bound by the following statement, it is thought that the stop codon UAG is less effective in translation termination and is therefore less desirable in the constructs described herein.

As used herein an "effective polyA sequence" refers to either a synthetic or non-synthetic sequence that contains multiple and sequential nucleotides containing an adenine base (an A polynucleotide string) and that increases expression of the gene to which it is operably-linked. A polyA sequence may be operably-linked to any gene in the transposon-based vector including, but not limited to, a transposase gene and a gene of interest. A preferred polyA sequence is optimized for use in the host animal or human and for the desired end product.

The goal is to use a poly A that gives a similar level of expression as the gene being replaced, or the desired result. With siRNA for example, only a few copies of the RNAi sequence are required, so the mRNA may not have to be extremely stable, and in fact may be detrimental or just a waste of energy for the cell (See Zhang et al., Nucleic Acids Research, database issue, Vol. 33:D116-D120 2005).

In one embodiment, the polyA sequence is optimized for use in an avian species and more specifically, a chicken. An avian optimized polyA sequence generally contains a minimum of 40 base pairs, preferably between approximately 40 and several hundred base pairs, and more preferably approximately 75 base pairs that precede the A polynucleotide string and thereby separate the stop codon from the A polynucleotide string. In one embodiment of the present invention, the polyA sequence comprises a conalbumin polyA sequence as provided in SEQ ID NO:17 and as taken from GenBank accession # Y00407, base pairs 10651-11058. In another embodiment, the polyA sequence comprises a synthetic polynucleotide sequence shown in SEQ ID NO:18. In yet another embodiment, the polyA sequence comprises an avian optimized polyA sequence provided in SEQ ID NO:19. A chicken optimized polyA sequence may also have a reduced amount of CT repeats as compared to a synthetic polyA sequence.

It is a surprising discovery of the present invention that such an avian optimized poly A sequence increases expression of a polynucleotide to which it is operably-linked in an avian as compared to a non-avian optimized polyA sequence. It is to be understood that polyA sequences may be optimized for other classes of animals, such as mammals, and used in the transposon-based vectors of the present invention to provide gene therapy. Accordingly, the present invention includes methods of or increasing incorporation of a gene of interest wherein the gene of interest resides in a transposon-based vector containing a transposase gene and wherein the transposase gene is operably linked to an avian optimized polyA sequence. The present invention also includes methods of increasing expression of a gene of interest in an avian that includes administering a gene of interest to the avian, wherein the gene of interest is operably-linked to an avian optimized polyA sequence. An avian optimized polyA nucleotide string is defined herein as a polynucleotide containing an A polynucleotide string and a minimum of 40 base pairs, preferably between approximately 40 and several hundred base pairs, and more preferably approximately 75 base pairs that precede the A polynucleotide string. The present invention further provides transposon-based vectors containing a gene of interest or transposase gene operably linked to an avian optimized polyA sequence.

Promoters and Enhancers

The first promoter operably-linked to the transposase gene and the second promoter operably-linked to the gene of interest can be a constitutive promoter or an inducible promoter. Constitutive promoters include, but are not limited to, immediate early cytomegalovirus (CMV) promoter, herpes simplex virus 1 (HSV1) immediate early promoter, SV40 promoter, lysozyme promoter, early and late CMV promoters, early and late HSV promoters, β-actin promoter, tubulin promoter, Rous-Sarcoma virus (RSV) promoter, and heat-shock protein (HSP) promoter. Inducible promoters include tissue-specific promoters, developmentally-regulated promoters and chemically inducible promoters. Examples of tissue-specific promoters include the glucose-6-phosphatase (G6P) promoter, vitellogenin promoter, ovalbumin promoter, ovomucoid promoter, conalbumin promoter, ovotransferrin promoter, prolactin promoter, kidney uromodulin promoter, and placental lactogen promoter. In one embodiment, the vitellogenin promoter includes a polynucleotide sequence of SEQ ID NO:20. The G6P promoter sequence may be deduced from a rat G6P gene untranslated upstream region provided in GenBank accession number U57552.1. Examples of developmentally-regulated promoters include the homeobox promoters and several hormone induced promoters. Examples of chemically inducible promoters include reproductive hormone induced promoters and antibiotic inducible promoters such as the tetracycline inducible promoter and the zinc-inducible metallothionine promoter.

Other inducible promoter systems include the Lac operator repressor system inducible by IPTG (isopropyl beta-D-thiogalactoside) (Cronin, A. et al. 2001. Genes and Development, v. 15), ecdysone-based inducible systems (Hoppe, U. C. et al. 2000. Mol. Ther. 1:159-164); estrogen-based inducible systems (Braselmann, S. et al. 1993. Proc. Natl. Acad. Sci. 90:1657-1661); progesterone-based inducible systems using a chimeric regulator, GLVP, which is a hybrid protein consisting of the GAL4 binding domain and the herpes simplex virus transcriptional activation domain, VP16, and a truncated form of the human progesterone receptor that retains the ability to bind ligand and can be turned on by RU486 (Wang, et al. 1994. Proc. Natl. Acad. Sci. 91:8180-8184); CID-based inducible systems using chemical inducers of dimerization (CIDs) to regulate gene expression, such as a system wherein rapamycin induces dimerization of the cellular proteins FKBP12 and FRAP (Belshaw, P. J. et al. 1996. J. Chem. Biol. 3:731-738; Fan, L. et al. 1999. Hum. Gene Ther. 10:2273-2285; Shariat, S. F. et al. 2001. Cancer Res. 61:2562-2571; Spencer, D. M. 1996. Curr. Biol. 6:839-847). Chemical substances that activate the chemically inducible promoters can be administered to the animal containing the transgene of interest via any method known to those of skill in the art.

Other examples of cell-specific and constitutive promoters include but are not limited to smooth-muscle SM22 promoter, including chimeric SM22alpha/telokin promoters (Hoggatt A. M. et al., 2002. Circ Res. 91(12):1151-9); ubiquitin C promoter (Biochim Biophys Acta, 2003. Jan. 3; 1625(1):52-63); Hsf2 promoter; murine COMP (cartilage oligomeric matrix protein) promoter; early B cell-specific mb-1 promoter (Sigvardsson M., et al., 2002. Mol. Cell Biol. 22(24): 8539-51); prostate specific antigen (PSA) promoter (Yoshimura I. et al., 2002, J. Urol. 168(6):2659-64); exorh promoter and pineal expression-promoting element (Asaoka Y., et al., 2002. Proc. Natl. Acad. Sci. 99(24):15456-61); neural and liver ceramidase gene promoters (Okino N. et al., 2002. Biochem. Biophys. Res. Commun. 299(1):160-6); PSP94 gene promoter/enhancer (Gabril M. Y. et al., 2002. Gene Ther. 9(23):1589-99); promoter of the human FAT/CD36 gene (Kuriki C., et al., 2002. Biol. Pharm. Bull. 25(11): 1476-8); VL30 promoter (Staplin W. R. et al., 2002. Blood Oct. 24, 2002); and, IL-10 promoter (Brenner S., et al., 2002. J. Biol. Chem. Dec. 18, 2002). Additional promoters are shown in Table 1.

Examples of avian promoters include, but are not limited to, promoters controlling expression of egg white proteins, such as ovalbumin, ovotransferrin (conalbumin), ovomucoid, lysozyme, ovomucin, g2 ovoglobulin, g3 ovoglobulin, ovoflavoprotein, ovostatin (ovomacroglobin), cystatin, avidin, thiamine-binding protein, glutamyl aminopeptidase minor glycoprotein 1, minor glycoprotein 2; and promoters controlling expression of egg-yolk proteins, such as vitellogenin, very low-density lipoproteins, low density lipoprotein, cobalamin-binding protein, riboflavin-binding protein, biotin-binding protein (Awade, 1996. Z. Lebensm. Unters. Forsch. 202:1-14). An advantage of using the vitellogenin promoter is that it is active during the egg-laying stage of an animal's life-cycle, which allows for the production of the protein of interest to be temporally connected to the import of the protein of interest into the egg yolk when the protein of interest is equipped with an appropriate targeting sequence. In some embodiments, the avian promoter is an oviduct-specific promoter. As used herein, the term "oviduct-specific promoter" includes, but is not limited to, ovalbumin; ovotransferrin (conalbumin); ovomucoid; O1, O2, O3, O4 or O5 avidin; ovomucin; g2 ovoglobulin; g3 ovoglobulin; ovoflavoprotein; and ovostatin (ovomacroglobin) promoters.

When germline transformation occurs via intraovarian or intratesticular administration, or when hepatocytes are targeted for incorporation of components of a vector through non-germ line administration, liver-specific promoters may be operably-linked to the gene of interest to achieve liver-specific expression of the transgene. Liver-specific promoters of the present invention include, but are not limited to, the following promoters, vitellogenin promoter, G6P promoter, cholesterol-7-alpha-hydroxylase (CYP7A) promoter, phenylalanine hydroxylase (PAH) promoter, protein C gene promoter, insulin-like growth factor I (IGF-I) promoter, bilirubin UDP-glucuronosyltransferase promoter, aldolase B promoter, furin promoter, metallothionine promoter, albumin promoter, and insulin promoter.

Also included in the present invention are promoters that can be used to target expression of a protein of interest into the milk of a milk-producing animal including, but not limited to, β lactoglobin promoter, whey acidic protein promoter, lactalbumin promoter and casein promoter.

When germline transformation occurs via intraovarian or intratesticular administration, or when cells of the immune system are targeted through non-germ line administration, immune system-specific promoters may be operably-linked to the gene of interest to achieve immune system-specific expression of the transgene. Accordingly, promoters associated with cells of the immune system may also be used. Acute phase promoters such as interleukin (IL)-1 and IL-2 may be employed. Promoters for heavy and light chain Ig may also be employed. The promoters of the T cell receptor components CD4 and CD8, B cell promoters and the promoters of CR2 (complement receptor type 2) may also be employed. Immune system promoters are preferably used when the desired protein is an antibody protein.

It is to be understood that any cell may be targeted for incorporation of a desired gene to provide gene therapy. Such cells may include, without limitation, endocrine cells or cancer cells. Promoters specific for selected endocrine cells, such as insulin-producing islet cells, hypophyseal growth hormone producing cells, or estrogen-producing follicular cells are known to one of ordinary skill in the art and may be incorporated into the transposon-based vectors of the present invention in order to provide gene therapy, by modulating hormone synthesis and secretion. Endocrine disorders and associated conditions of over or underproduction of hormones are known to one of ordinary skill in the art and many such conditions are described in textbooks such as Williams Textbook of Endocrinology, $10^{th}$ ed., Williams, R. H. et al., eds. 2002, W.B. Saunders. Specific cancerous cells, such as ovarian cancer cells, are known to produce and release specific molecules. Promoters specific for these cells, and other cancerous cells, are known to one of ordinary skill in the art and may be incorporated into the transposon-based vectors of the present invention in order to provide gene therapy, perhaps by producing inhibitory RNA in these cells or by producing proteins or peptides that interfere with cancer cell function or replication.

Additional gene targets, especially related to cancer, are oncogenes and also genes involved in cellular functions such as cell division, microtubule production and spindle formation, growth factors, growth factor receptors, oncoproteins and signal transduction pathways associated with transducing signals associated with function of cancerous cells. It is to be understood that a gene target may be a particular protein or enzyme involved in a multistep process associate with cell function. For example, an enzyme that is a component in a metabolic pathway of several enzymes may be disrupted using inhibitory RNA, thereby affecting the function of this metabolic pathway.

Also included in this invention are modified promoters/enhancers wherein elements of a single promoter are duplicated, modified, or otherwise changed. In one embodiment, steroid hormone-binding domains of the ovalbumin promoter are moved from about −3.5 kb to within approximately the first 1000 base pairs of the gene of interest. Modifying an existing promoter with promoter/enhancer elements not found naturally in the promoter, as well as building an entirely synthetic promoter, or drawing promoter/enhancer elements from various genes together on a non-natural backbone, are all encompassed by the current invention.

Accordingly, it is to be understood that the promoters contained within the transposon-based vectors of the present invention may be entire promoter sequences or fragments of promoter sequences. For example, in one embodiment, the promoter operably linked to a gene of interest is an approximately 900 base pair fragment of a chicken ovalbumin promoter (SEQ ID NO:21). The constitutive and inducible promoters contained within the transposon-based vectors may also be modified by the addition of one or more modified Kozak sequences of ACCATG (SEQ ID NO:8).

As indicated above, the present invention includes transposon-based vectors containing one or more enhancers. These enhancers may or may not be operably-linked to their native promoter and may be located at any distance from their operably-linked promoter. A promoter operably-linked to an enhancer and a promoter modified to eliminate repressive regulatory effects are referred to herein as an "enhanced promoter." The enhancers contained within the transposon-based vectors may be enhancers found in birds, such as an ovalbumin enhancer, but are not limited to these types of enhancers. In one embodiment, an approximately 675 base pair enhancer element of an ovalbumin promoter is cloned upstream of an ovalbumin promoter with 300 base pairs of spacer DNA separating the enhancer and promoter. In one embodiment, the enhancer used as a part of the present invention comprises base pairs 1-675 of a chicken ovalbumin enhancer from GenBank accession #S82527.1. The polynucleotide sequence of this enhancer is provided in SEQ ID NO:22.

Also included in some of the transposon-based vectors of the present invention are cap sites and fragments of cap sites. In one embodiment, approximately 50 base pairs of a 5' untranslated region wherein the capsite resides are added on the 3' end of an enhanced promoter or promoter. An exemplary 5' untranslated region is provided in SEQ ID NO:23. A putative cap-site residing in this 5' untranslated region preferably comprises the polynucleotide sequence provided in SEQ ID NO:24.

In one embodiment of the present invention, the first promoter operably-linked to the transposase gene is a constitutive promoter and the second promoter operably-linked to the gene of interest is a cell specific promoter. In the second embodiment, use of the first constitutive promoter allows for constitutive activation of the transposase gene and incorporation of the gene of interest into virtually all cell types, including the germline of the recipient animal. Although the gene of interest is incorporated into the germline generally, the gene of interest may only be expressed in a tissue-specific manner to achieve gene therapy. A transposon-based vector having a constitutive promoter operably-linked to the transposase gene can be administered by any route, and in one embodiment, the vector is administered to an ovary, to an artery leading to the ovary or to a lymphatic system or fluid proximal to the ovary. In another embodiment, the transposon-based vector having a constitutive promoter operably-linked to the transposase gene can be administered to vessels supplying the liver, muscle, brain, lung, kidney, heart or any other desired organ, tissue or cellular target.

It should be noted that cell- or tissue-specific expression as described herein does not require a complete absence of expression in cells or tissues other than the preferred cell or tissue. Instead, "cell-specific" or "tissue-specific" expression refers to a majority of the expression of a particular gene of interest in the preferred cell or tissue, respectively.

When incorporation of the gene of interest into the germline is not preferred, the first promoter operably-linked to the transposase gene can be a tissue-specific promoter. For example, transfection of a transposon-based vector containing a transposase gene operably-linked to a liver specific promoter such as the G6P promoter or vitellogenin promoter provides for activation of the transposase gene and incorporation of the gene of interest in the cells of the liver but not into the germline and other cells generally. In another example, transfection of a transposon-based vector containing a transposase gene operably-linked to an oviduct specific promoter such as the ovalbumin promoter provides for activation of the transposase gene and incorporation of the gene of interest in the cells of the oviduct but not into the germline and other cells generally. In this embodiment, the second promoter operably-linked to the gene of interest can be a constitutive promoter or an inducible promoter. In one embodiment, both the first promoter and the second promoter are an ovalbumin promoter. In embodiments wherein tissue-specific expression or incorporation is desired, it is preferred that the transposon-based vector is administered directly to the tissue of interest, to an artery leading to the organ or tissue of interest or to fluids surrounding the organ or tissue of interest. In one embodiment, the tissue of interest is the oviduct and administration is achieved by direct injection into the oviduct or an artery leading to the oviduct. In another embodiment, the tissue of interest is the liver and administration is achieved by direct injection into the portal vein or hepatic artery. In another embodiment, the tissue of interest is cardiac muscle tissue in the heart and administration is achieved by direct injection into the coronary arteries. In another embodiment, the tissue of interest is neural tissue and administration is achieved by direct injection into a cerebrovascular or spinovascular artery. In yet another embodiment, the target is a solid tumor and the administration is achieved by injection into a vessel supplying the tumor or by injection into the tumor. In yet another embodiment, the target is a diffuse cancer such as ovarian cancer spread throughout the abdominopelvic cavity and the administration is achieved by injection into the abdominopelvic cavity. In yet another embodiment, the target is the lung, for example the surfactant-producing cells, and the administration is achieved by injection into the right ventricle, the pulmonary artery or a branch thereof, or by aerosol administration into the respiratory system. In still another embodiment, the target is a lymph node and the administration is achieved by injection into lymphatic vessels supplying that node.

Accordingly, cell specific promoters may be used to enhance transcription in selected tissues. In birds, for example, promoters that are found in cells of the fallopian tube, such as ovalbumin, conalbumin, ovomucoid and/or lysozyme, are used in the vectors to ensure transcription of the gene of interest in the epithelial cells and tubular gland cells of the fallopian tube, leading to synthesis of the desired protein encoded by the gene and deposition into the egg white. In mammals, promoters specific for the epithelial cells of the alveoli of the mammary gland, such as prolactin, insulin, beta lactoglobin, whey acidic protein, lactalbumin, casein, and/or placental lactogen, are used in the design of vectors used for transfection of these cells for the production of desired proteins for deposition into the milk. In liver cells, the G6P promoter may be employed to drive transcription of the gene of interest for protein production. Proteins made in the liver of birds may be delivered to the egg yolk.

In order to achieve higher or more efficient expression of the transposase gene, the promoter and other regulatory sequences operably-linked to the transposase gene may be those derived from the host. These host specific regulatory sequences can be tissue specific as described above or can be of a constitutive nature. For example, an avian actin promoter and its associated polyA sequence can be operably-linked to a transposase in a transposase-based vector for transfection into an avian. Examples of other host specific promoters that could be operably-linked to the transposase include the myosin and DNA or RNA polymerase promoters.

Directing Sequences

In some embodiments of the present invention, the gene of interest is operably-linked to a directing sequence or a sequence that provides proper conformation to the desired protein encoded by the gene of interest. As used herein, the term "directing sequence" refers to both signal sequences and targeting sequences. An egg directing sequence includes, but is not limited to, an ovomucoid signal sequence, an ovalbumin signal sequence, a cecropin pre pro signal sequence, and a vitellogenin targeting sequence. The term "signal sequence" refers to an amino acid sequence, or the polynucleotide sequence that encodes the amino acid sequence, that directs the protein to which it is linked to the endoplasmic reticulum in a eukaryote, and more preferably the translocational pores in the endoplasmic reticulum, or the plasma membrane in a prokaryote, or mitochondria, such as for the purpose of gene therapy for mitochondrial diseases. Signal and targeting sequences can be used to direct a desired protein into, for example, the bloodstream, when the transposon-based vectors are administered to the liver of an animal.

Signal sequences can also be used to direct a desired protein into, for example, a secretory pathway for secretion and release of the desired protein. For example appropriate signal sequences can be employed to provide gene therapy for enhanced secretion of growth hormone from selected cells, for example growth hormone cells, or liver cells. This therapy is useful for treating deficiencies in circulating growth hormone levels and reduced stature. Liver specific promoters may be used to enhance production and release of antibodies or hepatic proteins such as globulins.

Figure 2:
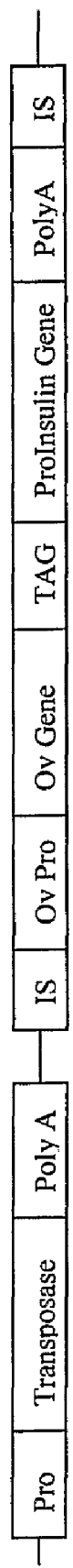
FIG. 2 depicts schematically a transposon-based vector for targeting deposition of a polypeptide in an egg white wherein Ov pro is the ovalbumin promoter, Ov protein is the ovalbumin protein and PolyA is a polyadenylation sequence. The TAG sequence includes a spacer sequence, the gp41 hairpin loop from HIV I and a protease cleavage site.

Signal sequences can also be used to direct a desired protein into, for example, a secretory pathway for incorporation into the egg yolk or the egg white, when the transposon-based vectors are administered to a bird or other egg-laying animal. One example of such a transposon-based vector is provided in FIG. 3 wherein the gene of interest is operably linked to the ovomucoid signal sequence. The present invention also includes a gene of interest operably-linked to a second gene containing a signal sequence. An example of such an embodiment is shown in FIG. 2 wherein the gene of interest is operably-linked to the ovalbumin gene that contains an ovalbumin signal sequence. Other signal sequences that can be included in the transposon-based vectors include, but are not limited to the ovotransferrin and lysozyme signal sequences. In one embodiment, the signal sequence is an ovalbumin signal sequence including a sequence shown in SEQ ID NO:25. In another embodiment, the signal sequence is a modified ovalbumin signal sequence including a sequence shown in SEQ ID NO:26 or SEQ ID NO:27.

As also used herein, the term "targeting sequence" refers to an amino acid sequence, or the polynucleotide sequence encoding the amino acid sequence, which amino acid sequence is recognized by a receptor located on the exterior of a cell. Binding of the receptor to the targeting sequence results in uptake of the protein or peptide operably-linked to the targeting sequence by the cell. One example of a targeting sequence is a vitellogenin targeting sequence that is recognized by a vitellogenin receptor (or the low density lipoprotein receptor) on the exterior of an oocyte. In one embodiment, the vitellogenin targeting sequence includes the polynucleotide sequence of SEQ ID NO:28. In another embodiment, the vitellogenin targeting sequence includes all or part of the vitellogenin gene. Other targeting sequences include VLDL and Apo E, which are also capable of binding the vitellogenin receptor. Since the ApoE protein is not endogenously expressed in birds, its presence may be used advantageously to identify birds carrying the transposon-based vectors of the present invention.

Genes of Interest Encoding Desired Proteins

A gene of interest selected for stable incorporation is designed to encode any desired protein or peptide or nucleic acid or to regulate any cellular response. In some embodiments, the desired proteins or peptides are released from cells into the surrounding environment, the lymphatic system or the vascular system. In some embodiments, the desired proteins or peptides are deposited in an egg or in milk. In other embodiments the desired proteins or peptides may be directed to an axon, to a hepatocyte cell membrane for release into the bloodstream, to the membrane of a beta lymphocyte for release into the circulation. It is to be understood that the present invention encompasses transposon-based vectors containing multiple genes of interest. The multiple genes of interest may each be operably-linked to a separate promoter and other regulatory sequence(s) or may all be operably-linked to the same promoter and other regulatory sequences(s). In one embodiment, multiple gene of interest are linked to a single promoter and other regulatory sequence(s) and each gene of interest is separated by a cleavage site or a pro portion of a signal sequence. A gene of interest may contain modifications of the codons for the first several N-terminal amino acids of the gene of interest, wherein the third base of each codon is changed to an A or a T without changing the corresponding amino acid.

Protein and peptide hormones are a preferred class of proteins in the present invention. Such protein and peptide hormones are synthesized throughout the endocrine system and include, but are not limited to, hypothalamic hormones and hypophysiotropic hormones, anterior, intermediate and posterior pituitary hormones, pancreatic islet hormones, hormones made in the gastrointestinal system, renal hormones, thymic hormones, parathyroid hormones, adrenal cortical and medullary hormones. Specifically, hormones that can be produced using the present invention include, but are not limited to, chorionic gonadotropin, corticotropin, erythropoietin, glucagons, IGF-1, oxytocin, platelet-derived growth factor, calcitonin, follicle-stimulating hormone, luteinizing hormone, thyroid-stimulating hormone, insulin, gonadotropin-releasing hormone and its analogs, vasopressin, octreotide, somatostatin, prolactin, adrenocorticotropic hormone, antidiuretic hormone, thyrotropin-releasing hormone (TRH), growth hormone-releasing hormone (GHRH), parathyroid hormone (PTH), glucagons, calcitrol, calciferol, atrial-natriuretic peptide, gastrin, secretin, cholecystokinin (CCK), neuropeptide Y, ghrelin, $PYY_{3-36}$, angiotensinogen, thrombopoietin, and leptin. It is to be understood that proteins that are normally folded or have chains or component parts that combine to form the active protein may be produced in a linear manner, for example luteinizing hormone (LH).

Other multimeric proteins that may be produced using the present invention are as follows: factors involved in the synthesis or replication of DNA, such as DNA polymerase alpha and DNA polymerase delta; proteins involved in the production of mRNA, such as TFIID and TFIIH; cell, nuclear and other membrane-associated proteins, such as hormone and other signal transduction receptors, active transport proteins and ion channels, multimeric proteins in the blood, including hemoglobin, fibrinogen and von Willibrand's Factor; proteins that form structures within the cell, such as actin, myosin, and tubulin and other cytoskeletal proteins; proteins that form structures in the extra cellular environment, such as collagen, elastin and fibronectin; proteins involved in intra- and extra-cellular transport, such as kinesin and dynein, the SNARE family of proteins (soluble NSF attachment protein receptor) and clathrin; proteins that help regulate chromatin structure, such as histones and protamines, Swi3p, Rsc8p and moira; multimeric transcription factors such as Fos, Jun and CBTF (CCAAT box transcription factor); multimeric enzymes such as acetylcholinesterase and alcohol dehydrogenase; chaperone proteins such as GroE, Gro EL (chaperonin 60) and Gro ES (chaperonin 10); anti-toxins, such as snake venom, botulism toxin, *Streptococcus* super antigens; lysins (enzymes from bacteriophage and viruses); as well as most allosteric proteins. By using appropriate polynucleotide sequences, species-specific hormones may be made by transgenic animals.

Figure 3:
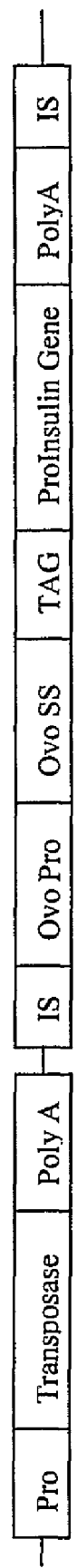
FIG. 3 depicts schematically a transposon-based vector for targeting deposition of a polypeptide in an egg white wherein Ovo pro is the ovomucoid promoter and Ovo SS is the ovomucoid signal sequence. The TAG sequence includes a spacer, the gp41 hairpin loop from HIV I and a protease cleavage site.
Figure 5:
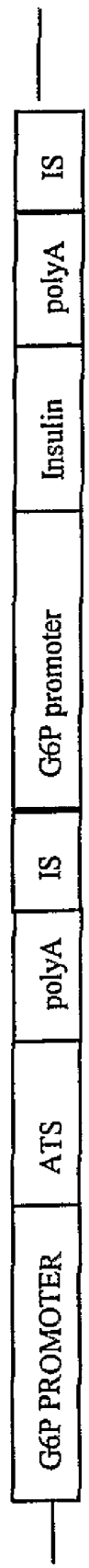
FIG. 5 is a schematic of a vector for stable transformation of liver cells for production of insulin. This vector provides for stable transformation of hepatocytes and allows the production of insulin in response to blood glucose levels.

In one embodiment of the present invention, the gene of interest is a proinsulin gene and the desired molecule is insulin. Proinsulin consists of three parts: a C-peptide and two strands of amino acids (the alpha and beta chains) that later become linked together to form the insulin molecule. FIGS. 2 and 3 are schematics of transposon-based vector constructs containing a proinsulin gene operably-linked to an ovalbumin promoter and ovalbumin protein or an ovomucoid promoter and ovomucoid signal sequence, respectively. In these embodiments, proinsulin is expressed in the oviduct tubular gland cells and then deposited in the egg white. One example of a proinsulin polynucleotide sequence is shown in SEQ ID NO:29, wherein the C-peptide cleavage site spans from Arg at position 31 to Arg at position 65. In other embodiments, the construct is designed for stable incorporation into hepatocytes and production of insulin for release into the vascular system.

Figure 6:
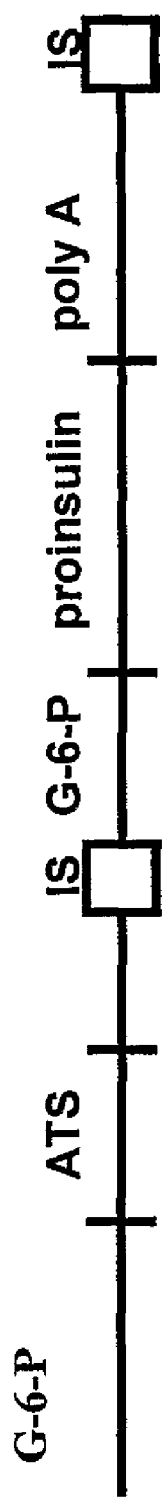
FIG. 6 depicts schematically a transposon-based vector targeted to hepatocytes for use in gene therapy for diabetes. A glucose-6-phosphatase (G-6-P) promoter is placed upstream of the transposase (ATS) and another G-6-P promoter is upstream of the proinsulin gene and the polyadenylation sequence (PolyA). Insertion sequences (IS) recognized by the transposase flank the G-6-P promoter, proinsulin gene and PolyA.

In another embodiment of the present invention a vector is constructed for use in gene therapy for diabetes (FIG. 6). A hepatocyte specific promoter is placed upstream of the transposase (ATS). The hepatocyte specific promoter could be a glucose-6-phosphatase promoter, liver specific albumin promoter, serum alpha-fetoprotein promoter, or other hepatocyte specific promoter. Such a specific promoter permits gene incorporation into the genome of hepatocytes since the transposase would not be expressed in other cell types. The promoter driving expression of the proinsulin gene is more specific, such as the glucose-6-phosphotase promoter. This promoter is desirable because it responds to blood glucose levels similar to beta islet cells of the pancreas. The proinsulin also contains a signal sequence to allow secretion from the liver cell. For instance, a signal sequence can be an albumin signal sequence or alpha-fetoprotein signal sequence. Likewise, the poly A is from a liver specific protein in order to optimize mRNA stability for the amount of desired expression. This is easily determined by one skilled in the art. The proinsulin and liver specific sequences are from the species of animal targeted for gene therapy, i.e., human sequence for human gene therapy, canine sequence for canine gene therapy or feline sequences for gene therapy in felines.

Figure 7:
FIG. 7 depicts schematically a transposon-based vector targeted to hepatocytes for use in gene therapy for production of growth hormone and treatment of growth hormone deficiencies. A glucose-6-phosphatase (G-6-P) promoter is placed upstream of the transposase (ATS) and an albumin promoter is upstream of the human growth hormone (hGH) gene and the polyadenylation sequence (PolyA). Insertion sequences (IS) recognized by the transposase flank the albumin promoter, GH gene and PolyA.

In another embodiment of the present invention a vector is constructed for use in gene therapy for treatment of growth hormone deficiency by expressing growth hormone from hepatocytes (FIG. 7). A liver specific promoter limits incorporation of the gene to hepatocytes. To further limit expression to hepatocytes, the vector is delivered as linear DNA as opposed to supercoiled DNA. Linear DNA has the added advantage of being destroyed more quickly than supercoiled DNA, so that if the DNA were delivered to a cell and the promoter was leaky (a low basal level of expression), the chances of expression before degradation would be minimized. The selection of growth hormone expression level is related to the dosage desired, i.e. strong constitutive promoter for larger doses, low to intermediate constitutive promoter for smaller doses. The signal sequence and poly A are hepatocyte derived for proper secretion and mRNA stability, respectively.

Figure 8:
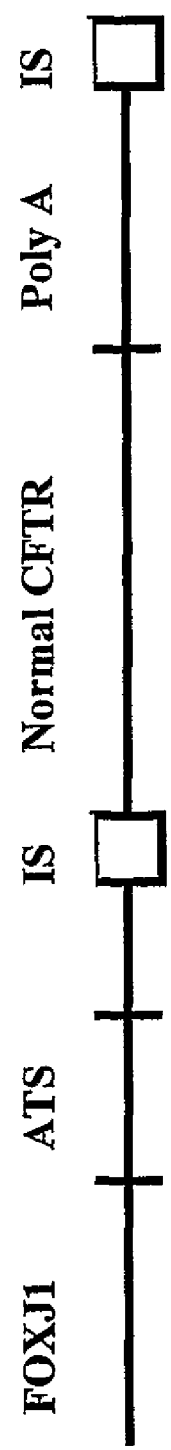
FIG. 8 depicts schematically a transposon-based vector targeted to respiratory epithelial cells for use in gene therapy for treatment of cystic fibrosis. A ciliated cell-specific promoter (FOXJ1) is placed upstream of the transposase (ATS), normal CFTR gene and the polyadenylation sequence (PolyA). Insertion sequences (IS) recognized by the transposase flank the normal cystic fibrosis transmembrane conductance regulator gene (CFTR) and PolyA.

In another embodiment of the present invention a vector is constructed for use in gene therapy for treatment of cystic fibrosis by specifically expressing the normal CFTR gene in respiratory epithelial cells (FIG. 8). To incorporate the desired transgene into respiratory epithelial cells, the ciliated cell-specific promoter (FOXJ1), or another lung specific promoter, is used to drive expression of the transposase. To treat the disease, a normal CFTR gene is delivered to the respiratory epithelial cells.

Figure 9:
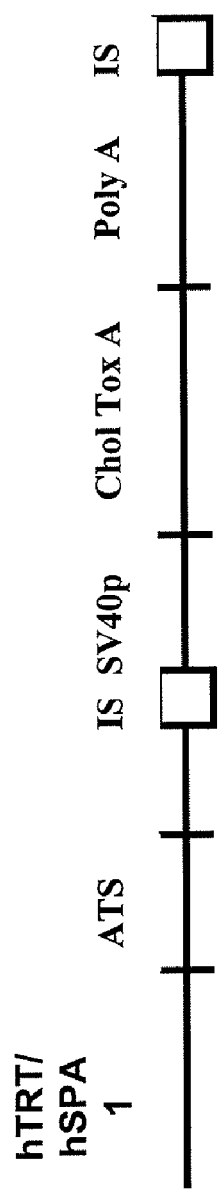
FIG. 9 depicts schematically a transposon-based vector targeted to cancer cells for use in gene therapy for treatment of cancer. Human telomerase reverse transcriptase/human surfactant protein A1 (HTRT/hSPA1) is placed upstream of the transposase (ATS). A SV40p promoter is placed upstream of the a gene for cholera toxin and the polyadenylation sequence (PolyA). Insertion sequences (IS) recognized by the transposase flank the SV40p promoter, cholera toxin gene and PolyA.

In another embodiment of the present invention a vector is constructed for use in gene therapy for treatment of cancer by specifically expressing the cholera toxin gene in cancer cells (FIG. 9). By linking the transposase to a cancer specific promoter, only cancer cells are stably transformed with the target gene. The target gene can encode for a toxin, such as cholera toxin A, expressed constitutively or under control of a cancer specific promoter to selectively kill the transfected cancer cells. In another embodiment, the transposase is placed under control of a cell specific promoter so that only one cell is transformed. In one embodiment, the target gene is a secreted fusion peptide, such as a peptide that has a component recognized by a surface receptor on a cancer cell and a lytic component that would destroy the cell following the binding of the other part of the fusion peptide to the cell surface receptor. In one embodiment, the target gene could encode for betaLH/Phor14, which is a ligand/lytic peptide combination that targets a receptor on a cancer cell with LH receptors and kills that cell with little or no damage to surrounding healthy tissue.

Serum proteins including lipoproteins such as high density lipoprotein (HDL), HDL-Milano and low density lipoprotein, apolipoprotein, albumin, clotting cascade factors, factor VIII, factor IX, fibrinogen, and globulins are also included in the group of desired proteins of the present invention. Immunoglobulins are one class of desired globulin molecules and include but are not limited to IgG, IgM, IgA, IgD, IgE, IgY, lambda chains, kappa chains and fragments thereof; bi-specific antibodies, and fragments thereof; scFv fragments, Fc fragments, and Fab fragments as well as dimeric, trimeric and oligomeric forms of antibody fragments. Desired antibodies include, but are not limited to, naturally occurring antibodies, animal-specific antibodies, human antibodies, humanized antibodies, autoantibodies and hybrid antibodies. Genes encoding modified versions of naturally occurring antibodies or fragments thereof and genes encoding artificially designed antibodies or fragments thereof may be incorporated into the transposon-based vectors of the present invention. Desired antibodies also include antibodies with the ability to bind specific ligands, for example, antibodies against proteins associated with cancer-related molecules, such as anti-her 2, or anti-CA125. Accordingly, the present invention encompasses a transposon-based vector containing one or more genes encoding a heavy immunoglobulin (Ig) chain and a light Ig chain. Further, more than one gene encoding for more than one antibody may be administered in one or more transposon-based vectors of the present invention. In this manner, antibodies may be made in liver cells or another cell selected for transfection, such as fibroblasts and released locally or gain access to the circulation. In one embodiment, a transposon-based vector contains a heavy Ig chain and a light Ig chain, both operably linked to a promoter.

Antibodies used as therapeutic reagents include but are not limited to antibodies for use in cancer immunotherapy against specific antigens, or for providing passive immunity to an animal against an infectious disease or a toxic agent. Antibodies may be made by the animal receiving the transposon-based vectors to facilitate the animal's immune response to a selected antigen. Animals receiving gene therapy to enhance resistance to a disease or to fight an ongoing disease, such as cancer, may receive a transposon-based vector containing genes encoding antibodies that bind to epitopes on cancer cells.

Antibodies that may be made with the practice of the present invention include, but are not limited to primary antibodies, secondary antibodies, designer antibodies, anti-protein antibodies, anti-peptide antibodies, anti-DNA antibodies, anti-RNA antibodies, anti-hormone antibodies, anti-hypophysiotropic peptides, antibodies against non-natural antigens, anti-anterior pituitary hormone antibodies, anti-posterior pituitary hormone antibodies, anti-venom antibodies, anti-tumor marker antibodies, antibodies directed against epitopes associated with infectious disease, including, anti-viral, anti-bacterial, anti-protozoal, anti-fungal, anti-parasitic, anti-receptor, anti-lipid, anti-phospholipid, anti-growth factor, anti-cytokine, anti-monokine, anti-idiotype, and anti-accessory (presentation) protein antibodies. Antibodies made with the present invention, as well as light chains or heavy chains, may also be used to inhibit enzyme activity.

Antibodies that may be produced using the present invention include, but are not limited to, antibodies made against the following proteins: Bovine γ-Globulin, Serum; Bovine IgG, Plasma; Chicken γ-Globulin, Serum; Human γ-Globulin, Serum; Human IgA, Plasma; Human IgA$_1$, Myeloma; Human IgA$_2$, Myeloma; Human IgA$_2$, Plasma; Human IgD, Plasma; Human IgE, Myeloma; Human IgG, Plasma; Human IgG, Fab Fragment, Plasma; Human IgG, F(ab')$_2$ Fragment, Plasma; Human IgG, Fc Fragment, Plasma; Human IgG$_1$, Myeloma; Human IgG$_2$, Myeloma; Human IgG$_3$, Myeloma; Human IgG$_4$, Myeloma; Human IgM, Myeloma; Human IgM, Plasma; Human Immunoglobulin, Light Chain κ, Urine; Human Immunoglobulin, Light Chains κ and λ, Plasma; Mouse γ-Globulin, Serum; Mouse IgG, Serum; Mouse IgM, Myeloma; Rabbit γ-Globulin, Serum; Rabbit IgG, Plasma; and Rat γ-Globulin, Serum. In one embodiment, the transposon-based vector comprises the coding sequence of light and heavy chains of a murine monoclonal antibody that shows specificity for human seminoprotein (GenBank Accession numbers AY129006 and AY129304 for the light and heavy chains, respectively).

A further non-limiting list of antibodies that recognize other antibodies is as follows: Anti-Chicken IgG, heavy (H) & light (L) Chain Specific (Sheep); Anti-Goat γ-Globulin (Donkey); Anti-Goat IgG, Fc Fragment Specific (Rabbit); Anti-Guinea Pig γ-Globulin (Goat); Anti-Human Ig, Light Chain, Type κ Specific; Anti-Human Ig, Light Chain, Type λ Specific; Anti-Human IgA, α-Chain Specific (Goat); Anti-Human IgA, Fab Fragment Specific; Anti-Human IgA, Fc Fragment Specific; Anti-Human IgA, Secretory; Anti-Human IgE, ε-Chain Specific (Goat); Anti-Human IgE, Fc Fragment Specific; Anti-Human IgG, Fc Fragment Specific (Goat); Anti-Human IgG, γ-Chain Specific (Goat); Anti-Human IgG, Fc Fragment Specific; Anti-Human IgG, Fd Fragment Specific; Anti-Human IgG, H & L Chain Specific (Goat); Anti-Human IgG$_1$, Fc Fragment Specific; Anti-Human IgG$_2$, Fc Fragment Specific; Anti-Human IgG$_2$, Fd Fragment Specific; Anti-Human IgG$_3$, Hinge Specific; Anti-Human IgG$_4$, Fc Fragment Specific; Anti-Human IgM, Fc Fragment Specific; Anti-Human IgM, μ-Chain Specific; Anti-Mouse IgE, ε-Chain Specific; Anti-Mouse γ-Globulin (Goat); Anti-Mouse IgG, γ-Chain Specific (Goat); Anti-Mouse IgG, γ-Chain Specific (Goat) F(ab')$_2$ Fragment; Anti-Mouse IgG, H & L Chain Specific (Goat); Anti-Mouse IgM, μ-Chain Specific (Goat); Anti-Mouse IgM, H & L Chain Specific (Goat); Anti-Rabbit γ-Globulin (Goat); Anti-Rabbit IgG, Fc Fragment Specific (Goat); Anti-Rabbit IgG, H & L Chain Specific (Goat); Anti-Rat γ-Globulin (Goat); Anti-Rat IgG, H & L Chain Specific; Anti-Rhesus Monkey γ-Globulin (Goat); and, Anti-Sheep IgG, H & L Chain Specific.

Another non-limiting list of the antibodies that may be produced using the present invention is provided in product catalogs of companies such as Phoenix Pharmaceuticals, Inc. (530 Harbor Boulevard, Belmont, Calif.), Peninsula Labs (San Carlos Calif.), SIGMA (St. Louis, Mo.), Cappel ICN (Irvine, Calif.), and Calbiochem (La Jolla, Calif.), which are all available electronically via the internet and which are incorporated herein by reference in their entirety. The polynucleotide sequences encoding these antibodies may be obtained from the scientific literature, from patents, and from databases such as GenBank. Alternatively, one of ordinary skill in the art may design the polynucleotide sequence to be incorporated into the genome by choosing the codons that encode for each amino acid in the desired antibody. Antibodies made by the transgenic animals of the present invention include antibodies that may be used as therapeutic reagents, for example in cancer immunotherapy against specific antigens. Some of these antibodies include, but are not limited to, antibodies which bind the following ligands: adrenomedulin, amylin, calcitonin, amyloid, calcitonin gene-related peptide, cholecystokinin, gastrin, gastric inhibitory peptide, gastrin releasing peptide, interleukin, interferon, cortistatin, somatostatin, endothelin, sarafotoxin, glucagon, glucagon-like peptide, insulin, atrial natriuretic peptide, BNP, CNP, neurokinin, substance P, leptin, neuropeptide Y, melanin concentrating hormone, melanocyte stimulating hormone, orphanin, endorphin, dynorphin, enkephalin, enkephalin, leumorphin, peptide F, PACAP, PACAP-related peptide, parathyroid hormone, urocortin, corticotrophin releasing hormone, PHM, PHI, vasoactive intestinal polypeptide, secretin, ACTH, angiotensin, angiostatin, bombesin, endostatin, bradykinin, FMRF amide, galanin, gonadotropin releasing hormone (GnRH) associated peptide, GnRH, growth hormone releasing hormone, inhibin, granulocyte-macrophage colony stimulating factor (GM-CSF), motilin, neurotensin, oxytocin, vasopressin, osteocalcin, pancreastatin, pancreatic polypeptide, peptide YY, proopiomelanocortin, transforming growth factor, vascular endothelial growth factor, vesicular monoamine transporter, vesicular acetylcholine transporter, ghrelin, NPW, NPB, C3d, prokinetican, thyroid stimulating hormone, luteinizing hormone, follicle stimulating hormone, prolactin, growth hormone, beta-lipotropin, melatonin, kallikriens, kinins, prostaglandins, erythropoietin, p146 (SEQ ID NO:30 amino acid sequence, SEQ ID NO:31, nucleotide sequence), estrogen, testosterone, corticosteroids, mineralocorticoids, thyroid hormone, thymic hormones, connective tissue proteins, nuclear proteins, actin, avidin, activin, agrin, albumin, and prohormones, propeptides, splice variants, fragments and analogs thereof.

The following is yet another non-limiting list of antibodies that can be produced by the methods of present invention: abciximab (ReoPro), abciximab anti-platelet aggregation monoclonal antibody, anti-CD11a (hu1124), anti-CD18 antibody, anti-CD20 antibody, anti-cytomegalovirus (CMV) antibody, anti-digoxin antibody, anti-hepatitis B antibody, anti-HER-2 antibody, anti-idiotype antibody to GD3 glycolipid, anti-IgE antibody, anti-IL-2R antibody, antimetastatic cancer antibody (mAb 17-1A), anti-rabies antibody, anti-respiratory syncytial virus (RSV) antibody, anti-Rh antibody, anti-TCR, anti-TNF antibody, anti-VEGF antibody and Fab fragment thereof, rattlesnake venom antibody, black widow spider venom antibody, coral snake venom antibody, antibody against very late antigen-4 (VLA-4), C225 humanized antibody to EGF receptor, chimeric (human & mouse) antibody against TNFα, antibody directed against GPIIb/IIIa receptor on human platelets, gamma globulin, anti-hepatitis B immunoglobulin, human anti-D immunoglobulin, human antibodies against S aureus, human tetanus immunoglobulin, humanized antibody against the epidermal growth receptor-2, humanized antibody against the α subunit of the interleukin-2 receptor, humanized antibody CTLA4IG, humanized antibody to the IL-2 R α-chain, humanized anti-CD40-ligand monoclonal antibody (5c8), humanized mAb against the epidermal growth receptor-2, humanized mAb to rous sarcoma virus, humanized recombinant antibody (IgG1k) against respiratory syncytial virus (RSV), lymphocyte immunoglobulin (anti-thymocyte antibody), lymphocyte immunoglobulin, mAb against factor VII, MDX-210 bi-specific antibody against HER-2, MDX-22, MDX-220 bi-specific antibody against TAG-72 on tumors, MDX-33 antibody to FcγR1 receptor, MDX-447 bi-specific antibody against EGF receptor, MDX-447 bispecific humanized antibody to EGF receptor, MDX-RA immunotoxin (ricin A linked) antibody, Medi-507 antibody (humanized form of BTI-322) against CD2 receptor on T-cells, monoclonal antibody LDP-02, muromonab-CD3(OKT3) antibody, OKT3 ("muromomab-CD3") antibody, PRO 542 antibody, ReoPro ("abciximab") antibody, and TNF-IgG fusion protein. It is to be understood that wherever the term "humanized" appears in the present patent application with regard to an antibody or molecule, that an antibody or molecule may be designed to be specific for any animal using selected polynucleotide sequences in the gene of interest included in the transposon-based vectors. Antibodies may be made against any selected antigen known to one of ordinary skill in the art.

The antibodies prepared using the methods of the present invention may also be designed to possess specific labels that may be detected through means known to one of ordinary skill in the art so that their location and distribution can be assessed following gene therapy and expression of the antibodies. The antibodies may also be designed to possess specific sequences useful for purification through means known to one of ordinary skill in the art. Specialty antibodies designed for binding specific antigens may also be made in transgenic animals using the transposon-based vectors of the present invention.

Production of a monoclonal antibody using the transposon-based vectors of the present invention can be accomplished in a variety of ways. In one embodiment, two vectors may be constructed: one that encodes the light chain, and a second vector that encodes the heavy chain of the monoclonal antibody. These vectors may then be incorporated into the genome of the target animal by methods disclosed herein. In an alternative embodiment, the sequences encoding light and heavy chains of a monoclonal antibody may be included on a single DNA construct. For example, the coding sequence of light and heavy chains of a murine monoclonal antibody that show specificity for human seminoprotein can be expressed using transposon-based constructs of the present invention (GenBank Accession numbers AY129006 and AY129304 for the light and heavy chains, respectively).

The transposon based vectors may include genes encoding proteins and peptides synthesized by the immune system including those synthesized by the thymus, lymph nodes, spleen, and the gastrointestinal associated lymph tissues (GALT) system. The immune system proteins and peptides proteins that can be made in transgenic animals using the transposon-based vectors of the present invention include, but are not limited to, alpha-interferon, beta-interferon, gamma-interferon, alpha-interferon A, alpha-interferon 1, G-CSF, GM-CSF, interlukin-1 (IL-1), IL-2, IL-3, IL-4, IL-5, IL-6, IL-7, IL-8, IL-9, IL-10, IL-11, IL-12, IL-13, TNF-α, and TNF-β. Other cytokines included in the present invention include cardiotrophin, stromal cell derived factors including stromal cell derived factor alpha, macrophage derived chemokine (MDC), melanoma growth stimulatory activity (MGSA), macrophage inflammatory proteins 1 alpha (MIP-1 alpha), 2, 3 alpha, 3 beta, 4 and 5, heat shock proteins (HSP) of different molecular weights (HSP-70, HSP-80, HSP-90 and others). Cell repellant molecules may also be made using the present invention, such as interleukins, stromal cell derived factor alpha and HSPs.

Lytic peptides, such as p146, are also included in the desired molecules that may be produced using the vectors and methods of the present invention. Lytic peptides are known to one of ordinary skill in the art and may be administered for gene therapy, for example to lyse cancer cells. In one embodiment, the p146 peptide comprises an amino acid sequence of SEQ ID NO:30. The present invention also encompasses a transposon-based vector comprising a p146 nucleic acid comprising a polynucleotide sequence of SEQ ID NO:31. Other lytic peptides and the class of proteins called lysins may be made with the transposon-based vectors of the present invention.

Enzymes are another class of proteins that may be made through gene therapy of the transposon-based vectors of the present invention. Such enzymes include but are not limited to adenosine deaminase, alpha-galactosidase, cellulase, collagenase, dnaseI, hyaluronidase, lactase, L-asparaginase, pancreatin, papain, streptokinase B, subtilisin, superoxide dismutase, thrombin, trypsin, urokinase, fibrinolysin, glucocerebrosidase and plasminogen activator. Many diseases, such as genetic diseases, involve problems in the production of enzymes. Through the practice of the present invention, administration of the transposon based vectors encoding specific enzymes provides gene therapy to the animal or human. Examples of such conditions are known to one of ordinary skill in the art and include phenylketonuria, Tay-Sachs disease, and severe combined immunodeficiency disease, associated respectively with phenylalanine hydroxylase, hexosaminidase, and adenine deaminase. Other genetic disorders are described in Robbins Pathologic Basis of Disease, Cotran et al. eds. $6^{th}$ ed., pp 139-187, 1999 Saunders, and in Harrison's Principles of Internal Medicine, Fauci et al. eds. $14^{th}$ ed. pp. 365-409, 1998, McGraw Hill. In some embodiments wherein the enzyme could have deleterious effects, additional amino acids and a protease cleavage site are added to the carboxy end of the enzyme of interest in order to prevent expression of a functional enzyme. Subsequent digestion of the enzyme with a protease results in activation of the enzyme.

Extracellular matrix proteins are one class of desired proteins that may be made through the gene therapy methods of the present invention. Examples include but are not limited to collagen, fibrin, elastin, laminin, and fibronectin and subtypes thereof. Animals receiving gene therapy for conditions such as arthritis or clotting disorders may make some of these matrix proteins. Gene therapy may be administered to stimulate formation of cartilage, such as articular cartilage, or for deposition of new bone. Intracellular proteins and structural proteins are other classes of desired proteins in the present invention.

Growth factors are another desired class of proteins that may be made through the gene therapy methods of the present invention and include, but are not limited to, transforming growth factor-α ("TGF-α"), transforming growth factor-β (TGF-β), platelet-derived growth factors (PDGF), fibroblast growth factors (FGF), including FGF acidic isoforms 1 and 2, FGF basic form 2 and FGF 4, 8, 9 and 10, nerve growth factors (NGF) including NGF 2.5s, NGF 7.0s and beta NGF and neurotrophins, brain derived neurotrophic factor, cartilage derived factor, growth factors for stimulation of the production of red blood cells, growth factors for stimulation of the production of white blood cells, bone growth factors (BGF), basic fibroblast growth factor, vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, beta3, skeletal growth factor, bone matrix derived growth factors, bone derived growth factors, erythropoietin (EPO) and mixtures thereof.

Another desired class of proteins that may be made may be made through the gene therapy of the present invention include, but are not limited to, leptin, leukemia inhibitory factor (LIF), tumor necrosis factor alpha and beta, ENBREL, angiostatin, endostatin, thrombospondin, osteogenic protein-1, bone morphogenetic proteins 2 and 7, osteonectin, somatomedin-like peptide, and osteocalcin.

Yet another desired class of proteins are blood proteins or clotting cascade protein including albumin, Prekallikrein, High molecular weight kininogen (HMWK) (contact activation cofactor; Fitzgerald, Flaujeac Williams factor), Factor I (Fibrinogen), Factor II (prothrombin), Factor III (Tissue Factor), Factor IV (calcium), Factor V (proaccelerin, labile factor, accelerator (Ac-) globulin), Factor VI (Va) (accelerin), Factor VII (proconvertin), serum prothrombin conversion accelerator (SPCA), cothromboplastin), Factor VIII (antihemophiliac factor A, antihemophilic globulin (AHG)), Factor IX (Christmas Factor, antihemophilic factor B, plasma thromboplastin component (PTC)), Factor X (Stuart-Prower Factor), Factor XI (Plasma thromboplastin antecedent (PTA)), Factor XII (Hageman Factor), Factor XIII (protransglutaminase, fibrin stabilizing factor (FSF), fibrinoligase), von Willibrand factor, Protein C, Protein S, Thrombomodulin, Antithrombin III.

A non-limiting list of the peptides and proteins that may be made may be made through the use of the gene therapy methods of the present invention is provided in product catalogs (electronically available over the internet) of companies such as Phoenix Pharmaceuticals, Inc. (530 Harbor Boulevard, Belmont, Calif.), Peninsula Labs (San Carlos Calif.), SIGMA, (St. Louis, Mo.), Cappel ICN (Irvine, Calif.), and Calbiochem (La Jolla, Calif.). The polynucleotide sequences encoding these proteins and peptides of interest may be obtained from the scientific literature, from patents, and from databases, such as GenBank. Alternatively, one of ordinary skill in the art may design the polynucleotide sequence to be incorporated into the genome by choosing the codons that encode for each amino acid in the desired protein or peptide.

Some of these desired proteins or peptides that may be made through the use of the gene therapy methods of the present invention include but are not limited to the following: adrenomedulin, amylin, calcitonin, amyloid, calcitonin gene-related peptide, cholecystokinin, gastrin, gastric inhibitory peptide, gastrin releasing peptide, interleukin, interferon, cortistatin, somatostatin, endothelin, sarafotoxin, glucagon, glucagon-like peptide, insulin, atrial natriuretic peptide, BNP, CNP, neurokinin, substance P, leptin, neuropeptide Y, melanin concentrating hormone, melanocyte stimulating hormone, orphanin, endorphin, dynorphin, enkephalin, leumorphin, peptide F, PACAP, PACAP-related peptide, parathyroid hormone, urocortin, corticotrophin releasing hormone, PHM, PHI, vasoactive intestinal polypeptide, secretin, ACTH, angiotensin, angiostatin, bombesin, endostatin, bradykinin, FMRF amide, galanin, gonadotropin releasing hormone (GnRH) associated peptide, GnRH, growth hormone releasing hormone, inhibin, granulocyte-macrophage colony stimulating factor (GM-CSF), motilin, neurotensin, oxytocin, vasopressin, osteocalcin, pancreastatin, pancreatic polypeptide, peptide YY, proopiomelanocortin, transforming growth factor, vascular endothelial growth factor, vesicular monoamine transporter, vesicular acetylcholine transporter, ghrelin, NPW, NPB, C3d, prokinetican, thyroid stimulating hormone, luteinizing hormone, follicle stimulating hormone, prolactin, growth hormone, beta-lipotropin, melatonin, kallikriens, kinins, prostaglandins, erythropoietin, p146 (SEQ ID NO:30, amino acid sequence, SEQ ID NO:31, nucleotide sequence), thymic hormones, connective tissue proteins, nuclear proteins, actin, avidin, activin, agrin, albumin, apolipoproteins, apolipoprotein A, apolipoprotein B, and prohormones, propeptides, splice variants, fragments and analogs thereof.

Other desired proteins that may be made by the transgenic animals receiving gene therapy according to the present invention include bacitracin, polymixin b, vancomycin, cyclosporine, anti-RSV antibody, alpha-1 antitrypsin (AAT), anti-cytomegalovirus antibody, anti-hepatitis antibody, anti-inhibitor coagulant complex, anti-rabies antibody, anti-Rh (D) antibody, adenosine deaminase, anti-digoxin antibody, antivenin crotalidae (rattlesnake venom antibody), antivenin latrodectus (black widow spider venom antibody), antivenin micrurus (coral snake venom antibody), aprotinin, corticotropin (ACTH), diphtheria antitoxin, lymphocyte immune globulin (anti-thymocyte antibody), protamine, thyrotropin, capreomycin, α-galactosidase, gramicidin, streptokinase, tetanus toxoid, tyrothricin, IGF-1, proteins of varicella vaccine, anti-TNF antibody, anti-IL-2r antibody, anti-HER-2 antibody, OKT3 ("muromonab-CD3") antibody, TNF-IgG fusion protein, ReoPro ("abciximab") antibody, ACTH fragment 1-24, desmopressin, gonadotropin-releasing hormone, histrelin, leuprolide, lypressin, nafarelin, peptide that binds GPIIb/GPIIIa on platelets (integrilin), goserelin, capreomycin, colistin, anti-respiratory syncytial virus, lymphocyte immune globulin (Thymoglovin, Atgam), panorex, alpha-antitrypsin, botulinin, lung surfactant protein, tumor necrosis receptor-IgG fusion protein (enbrel), gonadorelin, proteins of influenza vaccine, proteins of rotavirus vaccine, proteins of *haemophilus* b conjugate vaccine, proteins of poliovirus vaccine, proteins of pneumococcal conjugate vaccine, proteins of meningococcal C vaccine, proteins of influenza vaccine, megakaryocyte growth and development factor (MGDF), neuroimmunophilin ligand-A (NIL-A), brain-derived neurotrophic factor (BDNF), glial cell line-derived neurotrophic factor (GDNF), leptin (native), leptin B, leptin C, IL-1RA (interleukin-1RA), R-568, novel erythropoiesis-stimulating protein (NESP), humanized mAb to rous sarcoma virus (MEDI-493), glutamyl-tryptophan dipeptide IM862, LFA-3TIP immunosuppressive, humanized anti-CD40-ligand monoclonal antibody (5c8), gelsonin enzyme, tissue factor pathway inhibitor (TFPI), proteins of meningitis B vaccine, antimetastatic cancer antibody (mAb 17-1A), chimeric (human & mouse) mAb against TNFα, mAb against factor VII, relaxin, capreomycin, glycopeptide (LY333328), recombinant human activated protein C (rhAPC), humanized mAb against the epidermal growth receptor-2, altepase, anti-CD20 antigen, C2B8 antibody, insulin-like growth factor-1, atrial natriuretic peptide (anaritide), tenectaplase, anti-CD11a antibody (hu 1124), anti-CD18 antibody, mAb LDP-02, anti-VEGF antibody, Fab fragment of anti-VEGF Ab, APO2 ligand (tumor necrosis factor-related apoptosis-inducing ligand), rTGF-β (transforming growth factor-β), alpha-antitrypsin, ananain (a pineapple enzyme), humanized mAb CTLA41G, PRO 542 (mAb), D2E7 (mAb), calf intestine alkaline phosphatase, α-L-iduronidase, α-L-galactosidase (human glutamic acid decarboxylase, acid sphingomyelinase, bone morphogenetic protein-2 (rhBMP-2), proteins of HIV vaccine, T cell receptor (TCR) peptide vaccine, TCR peptides, V beta 3 and V beta 13.1. (IR502), (IR501), BI 1050/1272 mAb against very late antigen-4 (VLA-4), C225 humanized mAb to EGF receptor, anti-idiotype antibody to GD3 glycolipid, antibacterial peptide against *H. pylori*, MDX-447 bispecific humanized mAb to EGF receptor, anti-cytomegalovirus (CMV), Medi-491 B19 parvovirus vaccine, humanized recombinant mAb (IgG1k) against respiratory syncytial virus (RSV), urinary tract infection vaccine (against "pili" on *Escherechia coli* strains), proteins of lyme disease vaccine against *B. burgdorferi* protein (DbpA), proteins of Medi-501 human papilloma virus-11 vaccine (HPV), *Streptococcus pneumoniae* vaccine, Medi-507 mAb (humanized form of BTI-322) against CD2 receptor on T-cells, MDX-33 mAb to FcγR1 receptor, MDX-RA immunotoxin (ricin A linked) mAb, MDX-210 bi-specific mAb against HER-2, MDX-447 bi-specific mAb against EGF receptor, MDX-22, MDX-220 bi-specific mAb against TAG-72 on tumors, colony-stimulating factor (CSF) (molgramostim), humanized mAb to the IL-2 R α-chain (basiliximab), mAb to IgE (IGE 025A), myelin basic protein-altered peptide (MSP771A), humanized mAb against the epidermal growth receptor-2, humanized mAb against the α subunit of the interleukin-2 receptor, low molecular weight heparin, anti-hemophilic factor, and bactericidal/permeability-increasing protein (r-BPI).

The peptides and proteins made by animals receiving gene therapy using the present invention may be labeled using labels and techniques known to one of ordinary skill in the art. Some of these labels are described in the "Handbook of Fluorescent Probes and Research Products", ninth edition, Richard P. Haugland (ed) Molecular Probes, Inc. Eugene, Oreg.), which is incorporated herein in its entirety. Some of these labels may be genetically engineered into the polynucleotide sequence for the expression of the selected protein or peptide. The peptides and proteins may also have label-incorporation "handles" incorporated to allow labeling of an otherwise difficult or impossible to label protein.

It is to be understood that the various classes of desired peptides and proteins, as well as specific peptides and proteins described in this section may be modified as described below by inserting selected codons for desired amino acid substitutions into the gene incorporated into the transgenic animal.

Genes of Interest Encoding Desired Nucleic Acids and Other Molecule

The present invention may also be used to produce desired molecules other than proteins and peptides including, but not limited to, lipoproteins such as high density lipoprotein (HDL), HDL-Milano, and low density lipoprotein, lipids, carbohydrates, siRNA and ribozymes. In these embodiments, a gene of interest encodes a nucleic acid molecule or a protein that directs production of the desired molecule.

Nucleic Acids

RNAi technology can be directed against numerous aberrant genes, including those that allow proliferation of tumor cells. A variety of strategies can be used to inhibit cancer. These include the inhibition of overexpressed oncogenes, blocking cell division by interfering with cyclin E and related genes or promoting apoptosis by suppressing antiapoptotic genes. RNAi against multidrug resistance genes or chemoresistance targets may also provide useful cancer treatments. A non-limiting list of gene and protein targets for cancer therapy is found in Table 2 (M. Izquierdo. 2004. Short interfering RNAs as a tool for cancer gene therapy. Cancer Gene Therapy pp 1-11).

There are guidelines for designing dsRNA for use as RNAi therapy. These rules are known to one of ordinary skill in the art. Generally, the dsRNA cannot be shorter than 21 nucleotides (nt) or longer than 30 nt so the antiviral interferon response is not triggered. Other features to be avoided include, tight stem loops, inverted repeats, high sequence homology with other genes, and a lack of 4 or more consecutive T or A to avoid premature pol III transcription termination. Features to include are: 1) Initiation with a G or C after an AA in the 5' flanking sequence; 2) sense strand base preferences at positions 3 (A), 10 (U), 13 (A), and 19 (A); and 3) low G/C content (30-60%) (M. Izquierdo. 2004. Short interfering RNAs as a tool for cancer gene therapy. Cancer Gene Therapy pp 1-11).

The present invention provides a new and effective method for delivering shRNA using transposon-based vectors. This method can be used to treat various conditions and diseases and is a method of providing gene therapy. shRNA would be administered using a transposon based vector targeted to a specific cell type. The transposase (ATS) can be expressed by a cell-specific promoter (Table 1) to limit incorporation into a specific cell, and/or a cell-specific promoter could be used to express an shRNA to a gene listed in this document or any gene to be targeted for inactivation. In addition to the genes listed as targets for cancer therapy (see also Table 3), genes such as apoB (apolipoprotein B) to lower cholesterol (Akinc, et al. 2004. Nature 432(7017): 155-156), viral genes to eliminate hepatitis B and C (Shlomai and Shaul. 2004. Liver Int 6:526-31), metabolism and obesity genes (Campion, et al. 2004 Nutr. Rev 62:321-330), HIV (Berkhout. 2004. Curr Opin Mol Ther 6:141-145; Takaku. 2004. Antivir Chem Chemother. 15:57-65), cardiac disease through down regulation of phospholamban (PL; Poller et al. 2004. Z Kardiol 93: 171-193), and 5' nontranslated region (5' NTR) of hepatitis C (Kronke et al. 2004. J Virol. 78:3436-3446).

The present invention further encompasses gene therapy to produce inhibitory molecules to inhibit endogenous (i.e., non-vector) protein production. Such therapy may be used to inhibit a gene that is over expressed. These inhibitory molecules include antisense nucleic acids, siRNA, polynucleotide strands that affect cellular function and inhibitory proteins. In one embodiment, the endogenous protein whose expression is inhibited is an egg white protein including, but not limited to ovalbumin, ovotransferrin, ovomucin, ovoinhibitor, cystatin, ovostatin, lysozyme, ovoglobulin G2, ovoglobulin G3, avidin, or thiamin binding protein. In one embodiment, a transposon-based vector containing an ovalbumin DNA sequence, that upon transcription forms a double stranded RNA molecule, is transfected into an animal, such as a bird, and the bird's production of endogenous ovalbumin protein is reduced by the interference RNA mechanism (RNAi). In other embodiments, a transposon-based vector encodes an inhibitory RNA molecule that inhibits the expression of more than one egg white protein. One exemplary construct is provided in FIG. 4 wherein "Ovgen" indicates approximately 60 base pairs of an ovalbumin gene, "Ovotrans" indicates approximately 60 base pairs of an ovotransferrin gene and "Ovomucin" indicates approximately 60 base pairs of an ovomucin gene. These ovalbumin, ovotransferrin and ovomucin can be from any avian species, and in some embodiments, are from a chicken or quail. The term "pro" indicates the pro portion of a prepro sequence. One exemplary prepro sequence is that of cecropin and comprising base pairs 563-733 of the Cecropin cap site and Prepro provided in Genbank accession number XO7404.

Additionally, inducible knockouts or knockdowns of the endogenous protein may be created to achieve a reduction or inhibition of endogenous protein production. The approach may be used for inhibition of any selected endogenous protein in animals receiving gene therapy.

Modified Desired Proteins and Peptides Made by Animals Receiving Gene Therapy

"Proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein.

Typically, the amino acids making up a protein are numbered in order, starting at the amino terminal and increasing in the direction toward the carboxy terminal of the protein. Thus, when one amino acid is said to "follow" another, that amino acid is positioned closer to the carboxy terminal of the protein than the preceding amino acid.

The term "residue" is used herein to refer to an amino acid (D or L) or an amino acid mimetic that is incorporated into a protein by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above, individual substitutions, deletions or additions which alter, add or delete a single amino acid or a small percentage of amino acids (typically less than about 5%, more typically less than about 1%) in an encoded sequence are conservatively modified variations where the alterations result in the substitution of an amino acid with a chemically similar amino acid. Such substitutions may be engineered by selecting the desired nucleotides for insertion into the gene of interest in animals receiving gene therapy. Conservative substitutions in polynucleotide sequences are included within the scope of the present invention, wherein codons in a sequence may be replaced with other codons encoding for conservatively substituted amino acids, as explained below in the conservative substitution table. In other words, a codon in a polynucleotide sequence encoding for an alanine may be substituted with a codon encoding for a valine. Conservative substitution tables providing functionally similar amino acids are well known in the art. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A conservative substitution is a substitution in which the substituting amino acid (naturally occurring or modified) is structurally related to the amino acid being substituted, i.e., has about the same size and electronic properties as the amino acid being substituted. Thus, the substituting amino acid would have the same or a similar functional group in the side chain as the original amino acid. A "conservative substitution" also refers to utilizing a substituting amino acid which is identical to the amino acid being substituted except that a functional group in the side chain is protected with a suitable protecting group.

Suitable protecting groups are described in Green and Wuts, "Protecting Groups in Organic Synthesis", John Wiley and Sons, Chapters 5 and 7, 1991, the teachings of which are incorporated herein by reference. Preferred protecting groups are those which facilitate transport of the peptide through membranes, for example, by reducing the hydrophilicity and increasing the lipophilicity of the peptide, and which can be cleaved, either by hydrolysis or enzymatically (Ditter et al., 1968. J. Pharm. Sci. 57:783; Ditter et al., 1968. J. Pharm. Sci. 57:828; Differ et al., 1969. J. Pharm. Sci. 58:557; King et al., 1987. Biochemistry 26:2294; Lindberg et al., 1989. Drug Metabolism and Disposition 17:311; Tunek et al., 1988. Biochem. Pharm. 37:3867; Anderson et al., 1985 Arch. Biochem. Biophys. 239:538; and Singhal et al., 1987. FASEB J. 1:220). Suitable hydroxyl protecting groups include ester, carbonate and carbamate protecting groups. Suitable amine protecting groups include acyl groups and alkoxy or aryloxy carbonyl groups, as described above for N-terminal protecting groups. Suitable carboxylic acid protecting groups include aliphatic, benzyl and aryl esters, as described below for C-terminal protecting groups. In one embodiment, the carboxylic acid group in the side chain of one or more glutamic acid or aspartic acid residues in a peptide of the present invention is protected, preferably as a methyl, ethyl, benzyl or substituted benzyl ester, more preferably as a benzyl ester.

Provided below are groups of naturally occurring and modified amino acids in which each amino acid in a group has similar electronic and steric properties. Thus, a conservative substitution can be made by substituting an amino acid with another amino acid from the same group. Such substitutions may be engineered through selection of the appropriate nucleotides in constructing the gene of interest for introduction into animals receiving gene therapy. It is to be understood that these groups are non-limiting, i.e. that there are additional modified amino acids which could be included in each group.

Group I includes leucine, isoleucine, valine, methionine and modified amino acids having the following side chains: ethyl, n-propyl n-butyl. Preferably, Group I includes leucine, isoleucine, valine and methionine.

Group II includes glycine, alanine, valine and a modified amino acid having an ethyl side chain. Preferably, Group II includes glycine and alanine.

Group III includes phenylalanine, phenylglycine, tyrosine, tryptophan, cyclohexylmethyl glycine, and modified amino residues having substituted benzyl or phenyl side chains. Preferred substituents include one or more of the following: halogen, methyl, ethyl, nitro, —$NH_2$, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl isopropyl, cyclohexyl, benzyl or substituted benzyl), glutamine, asparagine, —CO—NH— alkylated glutamine or asparagines (e.g., methyl, ethyl, n-propyl and iso-propyl) and modified amino acids having the side chain —$(CH_2)_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, methyl aspartate, ethyl aspartate, benzyl aspartate and methyl glutamate, ethyl glutamate and benzyl glutamate, glutamine and asparagine.

Group V includes histidine, lysine, ornithine, arginine, N-nitroarginine, β-cycloarginine, γ-hydroxyarginine, N-amidinocitruline and 2-amino-4-guanidinobutanoic acid, homologs of lysine, homologs of arginine and homologs of ornithine. Preferably, Group V includes histidine, lysine, arginine and ornithine. A homolog of an amino acid includes from 1 to about 3 additional or subtracted methylene units in the side chain.

Group VI includes serine, threonine, cysteine and modified amino acids having C1-C5 straight or branched alkyl side chains substituted with —OH or —SH, for example, —$CH_2CH_2OH$, —$CH_2CH_2CH_2OH$ or —$CH_2CH_2OHCH_3$. Preferably, Group VI includes serine, cysteine or threonine.

In another aspect, suitable substitutions for amino acid residues include "severe" substitutions. A "severe substitution" is a substitution in which the substituting amino acid (naturally occurring or modified) has significantly different size and/or electronic properties compared with the amino acid being substituted. Thus, the side chain of the substituting amino acid can be significantly larger (or smaller) than the side chain of the amino acid being substituted and/or can have functional groups with significantly different electronic properties than the amino acid being substituted. Examples of severe substitutions of this type include the substitution of phenylalanine or cyclohexylmethyl glycine for alanine, isoleucine for glycine, a D amino acid for the corresponding L amino acid, or —NH—CH[(—CH$_2$)$_5$—COOH]—CO— for aspartic acid. Alternatively, a functional group may be added to the side chain, deleted from the side chain or exchanged with another functional group. Examples of severe substitutions of this type include adding of valine, leucine or isoleucine, exchanging the carboxylic acid in the side chain of aspartic acid or glutamic acid with an amine, or deleting the amine group in the side chain of lysine or ornithine. In yet another alternative, the side chain of the substituting amino acid can have significantly different steric and electronic properties that the functional group of the amino acid being substituted. Examples of such modifications include tryptophan for glycine, lysine for aspartic acid and —(CH$_2$)$_4$COOH for the side chain of serine. These examples are not meant to be limiting.

In another embodiment, for example in the synthesis of a peptide 26 amino acids in length, the individual amino acids may be substituted according in the following manner:

$AA_1$ is serine, glycine, alanine, cysteine or threonine;
$AA_2$ is alanine, threonine, glycine, cysteine or serine;
$AA_3$ is valine, arginine, leucine, isoleucine, methionine, ornithine, lysine, N-nitroarginine, β-cycloarginine, γ-hydroxyarginine, N-amidinocitruline or 2-amino-4-guanidinobutanoic acid;
$AA_4$ is proline, leucine, valine, isoleucine or methionine;
$AA_5$ is tryptophan, alanine, phenylalanine, tyrosine or glycine;
$AA_6$ is serine, glycine, alanine, cysteine or threonine;
$AA_7$ is proline, leucine, valine, isoleucine or methionine;
$AA_8$ is alanine, threonine, glycine, cysteine or serine;
$AA_9$ is alanine, threonine, glycine, cysteine or serine;
$AA_{10}$ is leucine, isoleucine, methionine or valine;
$AA_{11}$ is serine, glycine, alanine, cysteine or threonine;
$AA_{12}$ is leucine, isoleucine, methionine or valine;
$AA_{13}$ is leucine, isoleucine, methionine or valine;
$AA_{14}$ is glutamine, glutamic acid, aspartic acid, asparagine, or a substituted or unsubstituted aliphatic or aryl ester of glutamic acid or aspartic acid;
$AA_{15}$ is arginine, N-nitroarginine, β-cycloarginine, γ-hydroxy-arginine, N-amidinocitruline or 2-amino-4-guanidino-butanoic acid
$AA_{16}$ is proline, leucine, valine, isoleucine or methionine;
$AA_{17}$ is serine, glycine, alanine, cysteine or threonine;
$AA_{18}$ is glutamic acid, aspartic acid, asparagine, glutamine or a substituted or unsubstituted aliphatic or aryl ester of glutamic acid or aspartic acid;
$AA_{19}$ is aspartic acid, asparagine, glutamic acid, glutamine, leucine, valine, isoleucine, methionine or a substituted or unsubstituted aliphatic or aryl ester of glutamic acid or aspartic acid;
$AA_{20}$ is valine, arginine, leucine, isoleucine, methionine, ornithine, lysine, N-nitroarginine, β-cycloarginine, γ-hydroxyarginine, N-amidinocitruline or 2-amino-4-guanidinobutanoic acid;
$AA_{21}$ is alanine, threonine, glycine, cysteine or serine;
$AA_{22}$ is alanine, threonine, glycine, cysteine or serine;
$AA_{23}$ is histidine, serine, threonine, cysteine, lysine or ornithine;
$AA_{24}$ is threonine, aspartic acid, serine, glutamic acid or a substituted or unsubstituted aliphatic or aryl ester of glutamic acid or aspartic acid;
$AA_{25}$ is asparagine, aspartic acid, glutamic acid, glutamine, leucine, valine, isoleucine, methionine or a substituted or unsubstituted aliphatic or aryl ester of glutamic acid or aspartic acid; and
$AA_{26}$ is cysteine, histidine, serine, threonine, lysine or ornithine.

It is to be understood that these amino acid substitutions may be made for longer or shorter peptides than the 26 mer in the preceding example above, and for proteins.

In one embodiment of the present invention, codons for the first several N-terminal amino acids of the transposase are modified such that the third base of each codon is changed to an A or a T without changing the corresponding amino acid. It is preferable that between approximately 1 and 20, more preferably 3 and 15, and most preferably between 4 and 12 of the first N-terminal codons of the gene of interest are modified such that the third base of each codon is changed to an A or a T without changing the corresponding amino acid. In one embodiment, the first ten N-terminal codons of the gene of interest are modified in this manner.

When several desired proteins, protein fragments or peptides are encoded in the gene of interest to be incorporated into the genome, one of skill in the art will appreciate that the proteins, protein fragments or peptides may be separated by a spacer molecule such as, for example, a peptide, consisting of one or more amino acids. Generally, the spacer will have no specific biological activity other than to join the desired proteins, protein fragments or peptides together, or to preserve some minimum distance or other spatial relationship between them. However, the constituent amino acids of the spacer may be selected to influence some property of the molecule such as the folding, net charge, or hydrophobicity. The spacer may also be contained within a nucleotide sequence with a purification handle or be flanked by cleavage sites, such as proteolytic cleavage sites.

Such polypeptide spacers may have from about 1 to about 100 amino acids, preferably 3 to 20 amino acids, and more preferably 4-15 amino acids. The spacers in a polypeptide are independently chosen, but are preferably all the same. The spacers should allow for flexibility of movement in space and are therefore typically rich in small amino acids, for example, glycine, serine, proline or alanine. Preferably, peptide spacers contain at least 60%, more preferably at least 80% glycine or alanine. In addition, peptide spacers generally have little or no biological and antigenic activity. Preferred spacers are (Gly-Pro-Gly-Gly)$_x$ (SEQ ID NO:32) and (Gly$_4$-Ser)$_y$, wherein x is an integer from about 3 to about 9 and y is an integer from about 1 to about 8. Specific examples of suitable spacers include

```
(Gly-Pro-Gly-Gly)3
                                        SEQ ID NO: 33
Gly Pro Gly Gly Gly Pro Gly Gly Gly Pro Gly Gly (Gly4-Ser)3
                                        SEQ ID NO: 34
Gly Gly Gly Gly Ser Gly Gly Gly Gly Ser Gly Gly

Gly Gly Ser
or (Gly4-Ser)4
                                        SEQ ID NO: 35
Gly Gly Gly Gly Ser Gly Gly Gly Gly Ser Gly Gly

Gly Gly Ser Gly Gly Gly Gly Ser.
```

Nucleotide sequences encoding for the production of residues which may be useful in purification of the expressed recombinant protein in animals receiving gene therapy may also be built into the vector. Such sequences are known in the art and include the glutathione binding domain from glutathione S-transferase, polylysine, hexa-histidine or other cationic amino acids, thioredoxin, hemagglutinin antigen and maltose binding protein.

Additionally, nucleotide sequences may be inserted into the gene of interest to be incorporated so that the protein or peptide can also include from one to about six amino acids that create signals for proteolytic cleavage. In this manner, if a gene is designed to make one or more peptides or proteins of interest in the transgenic animal, specific nucleotide sequences encoding for amino acids recognized by enzymes may be incorporated into the gene to facilitate cleavage of the large protein or peptide sequence into desired peptides or proteins or both. For example, nucleotides encoding a proteolytic cleavage site can be introduced into the gene of interest so that a signal sequence can be cleaved from a protein or peptide encoded by the gene of interest. Nucleotide sequences encoding other amino acid sequences which display pH sensitivity or chemical sensitivity may also be added to the vector to facilitate separation of the signal sequence from the peptide or protein of interest.

Proteolytic cleavage sites include cleavage sites recognized by exopeptidases such as carboxypeptidase A, carboxypeptidase B, aminopeptidase I, and dipeptidylaminopeptidase; endopeptidases such as trypsin, V8-protease, enterokinase, factor Xa, collagenase, endoproteinase, subtilisin, and thrombin; and proteases such as Protease 3C IgA protease (Igase) Rhinovirus 3C(preScission)protease. Chemical cleavage sites are also included in the definition of cleavage site as used herein. Chemical cleavage sites include, but are not limited to, site cleaved by cyanogen bromide, hydroxylamine, formic acid, and acetic acid.

In one embodiment of the present invention, a TAG sequence is linked to the gene of interest. The TAG sequence serves three purposes: 1) it allows free rotation of the peptide or protein to be isolated so there is no interference from the native protein or signal sequence, i.e. vitellogenin, 2) it provides a "purification handle" to isolate the protein using column purification, and 3) it includes a cleavage site to remove the desired protein from the signal and purification sequences. Accordingly, as used herein, a TAG sequence includes a spacer sequence, a purification handle and a cleavage site. The spacer sequences in the TAG proteins contain one or more repeats shown in SEQ ID NO:36. A preferred spacer sequence comprises the sequence provided in SEQ ID NO:37. One example of a purification handle is the gp41 hairpin loop from HIV I. Exemplary gp41 polynucleotide and polypeptide sequences are provided in SEQ ID NO:38 and SEQ ID NO:39, respectively. However, it should be understood that any antigenic region may be used as a purification handle, including any antigenic region of gp41. Preferred purification handles are those that elicit highly specific antibodies. Additionally, the cleavage site can be any protein cleavage site known to one of ordinary skill in the art and includes an enterokinase cleavage site comprising the Asp Asp Asp Asp Lys sequence (SEQ ID NO:40) and a furin cleavage site. Constructs containing a TAG sequence are shown in FIGS. 2 and 3. In one embodiment of the present invention, the TAG sequence comprises a polynucleotide sequence of SEQ ID NO:41.

Gene Therapy

Administration of the transposon based vectors of the present invention to achieve gene therapy in animals may be used to treat numerous genetic and non-genetic disorders.

DNA constructs of the present invention can be used to transform any animal cell, including but not limited to: cells producing hormones, cytokines, growth factors, or any other biologically active substance; cells of the immune system; cells of the nervous system; muscle (striatal, cardiac, smooth) cells; vascular system cells; endothelial cells; skin cells; mammary cells; and lung cells, including bronchial and alveolar cells. Transformation of any endocrine cell by a transposon-based DNA construct is contemplated as a part of a present invention. DNA constructs of the present invention can be used to modulate, including both stimulation and inhibition, production of any substance, including but not limited to a hormone, a cytokine, or a growth factor, by an animal cell. Modulation of a regulated signal within a cell or a tissue, such as production of a second messenger, is also contemplated as a part of the present invention. In one aspect of the present invention, cells of the immune system may be the target for incorporation of a desired gene or genes encoding for production of antibodies. Accordingly, the thymus, bone marrow, beta lymphocytes (or B cells), gastrointestinal associated lymphatic tissue (GALT), Peyer's patches, bursa Fabricius, lymph nodes, spleen, and tonsil, and any other lymphatic tissue, may all be targets for administration of the compositions of the present invention. Use of the DNA constructs of the present invention is contemplated for treatment of any animal disease or condition that results from underproduction (such as diabetes) or overproduction (such as hyperthyroidism) of a hormone or other endogenous biologically active substance. Use of DNA constructs of the present invention to integrate nucleotide sequences encoding RNA molecules, such as anti-sense RNA or short interfering RNA, is also contemplated as a part of the present invention.

Genetic Disorders

Genetic disorders are well known to one of ordinary skill in the art and may include, but are not limited to, general classes of mutations, Mendelian disorders, disorders with multifactorial inheritance, cytogenetic disorders, and single gene disorders with nonclassic inheritance. Many genetic disorders are described in Robbins Pathologic Basis of Disease, Cotran et al. eds. $6^{th}$ ed., pp 139-187, 1999 Saunders, and in Harrison's Principles of Internal Medicine, Fauci et al. eds. $14^{th}$ ed. pp. 365-409, 1998, McGraw Hill. Genetic disorders that may be treated with the method of the present invention include, but are not limited to those presented in Table 3, which also identifies the gene and often the chromosome associated with the specific genetic disorder.

Mendelian disorders include autosomal dominant disorders autosomal recessive disorders and X-linked disorders. Such disorders may include defective enzymes, defects in receptor and transport systems, alterations in the structure, function or quality of non-enzyme proteins, and genetically determined adverse reactions to drugs. Some of these conditions are related to familial hypercholesterolemia, lysosomal storage diseases, glycogen storage diseases and neurofibromatosis. Provision of gene therapy using the method of the present invention may address, for example, supplementation of an animal with a protein or enzyme that the animal needs in view of its inadequate or faulty production of the protein. Practice of the present invention can be used to inactivate the defective gene through use of siRNA and then the transposon based vector can be used to insert the normal gene in order to restore function.

Other Disorders

The present invention also provides gene therapy for animals that may not possess a demonstrable genetic deficiency. However, such animals may require supplementation of specific proteins that may be produced in inadequate amounts or in a defective form that renders them biologically inactive or marginally active. Alternatively, animals may produce too much of a protein that causes a disease or condition that renders the animal sick. Such animals may require gene therapy to reduce the transcription of a gene that makes the protein. Such animals may require gene therapy to produce proteins or peptides to blunt or block the activity of the overabundant protein.

Diseases and Conditions

Numerous diseases and conditions may be treated with the gene therapy method of the present invention, including, but not limited to, diseases and conditions of the following systems: cardiovascular system (atherosclerosis, hypercholesterolemia, disorders of LDL, HDL and apolipoprotein synthesis and metabolism, hypertension); reproductive system (reproductive health and dysfunction, fertility, infertility, menopause, menarche, puberty, superovulation, timing of ovulation, inducement of ovulation, inducement of sterilization (especially of companion animals), mastitis, cancers of the reproductive system); endocrine and neuroendocrine systems (hypopituitary disorders, hypothalamic disorders, hypogonadism, precocious puberty, dwarfism, infertility, lactation, diabetes, thyroid disease, adrenal cortical or adrenal medullary disease, appetite, feeding, drinking, temperature regulation); metabolic system (digestive disorders, inborn errors of metabolism, disorders of intermediate metabolism, fat metabolism, Crohn's disease; phenylketonuria, chronic wasting disease, phosphofructokinase deficiency, pyruvic kinase deficiency; nervous system (Parkinson's disease, Alzheimer's disease, Huntington's disease, encephalopathy, bovine spongiform encephalopathy, conditions related to neurotransmitter transporter systems such as catecholamine transporters and reuptake mechanisms (serotonin, norepinephrine, dopamine) such as depression, psychosis, neurosis, addiction, alcoholism, motivation, bulimia, hyperphagia); immune system (feline immunodeficiency virus, simian immunodeficiency virus, immunodeficiency disorders including severe immunodeficiency disorders and severe combined immunodeficiency disorders, leukemia, autoimmune disorders, allergies, lupus, multiple sclerosis, scleroderma, disorders involving various immunoglobulins, interleukins, cytokines and lymphokines); hematologic and related disorders (sickle cell anemia, clotting disorders, von Willibrand's Disease); musculoskeletal system (arthritis, rheumatoid arthritis, osteoarthritis, muscular dystrophy); cancer (ovarian, prostate, breast, colon, brain, lung, kidney, skin); respiratory system (lung cancer, laryngeal cancer, cystic fibrosis); obesity; aging; cosmetic treatment of skin and hair; any form of cancer (skin (melanoma, basal, squamous), bladder, colon, stomach, esophageal, liver, pancreatic, testicular, prostate, ovarian, cervical, uterine, breast, lung, laryngeal, thyroid, adrenal, renal, penile, head, neck, brain (neural, glial); disorders involving receptors, particularly membrane bound receptors; and, infectious diseases (parasitic disease, bacterial infectious disease, viral disease, pneumovirus, Eastern equine encephalitis, West Nile virus, malaria, lyme disease, ehrlichosis, retroviral infections, rabies, and diseases borne by invertebrates such as ticks, fleas, flies and mosquitoes.

The transposon-based vectors of the present invention can be used for the treatment of various genetic disorders. For example, one or more LTR-vector complexes can be administered to an animal for the treatment of a single gene disorder including, but not limited to, animal equivalents of Huntington's disease, alpha-1-antitrypsin deficiency Alzheimer's disease, various forms or breast cancer, cystic fibrosis, galactosemia, congenital hypothyroidism, maple syrup urine disease, neurofibromatosis 1, phenylketonuria, sickle cell disease, and Smith-Lemli-Opitz (SLO/RSH) Syndrome any metabolic errors, autoimmune diseases, shipping fever in cattle, mastitis, bacterial or viral diseases, alteration of skin pigment in animals, production of animals with enhanced growth characteristics and nutrient utilization. In these embodiments, the transposon-based vector contains a non-mutated, or non-disease causing form of the gene known to cause such disorder. The transposon-based vectors of the present invention can also be used to treat multiple gene disorders. The transposon-based vectors of the present invention can be used as DNA vaccines and are useful in organ-specific disease treatments and localized disease treatments.

Preferably, the transposase contained within the transposase-based vector is operably linked to an inducible promoter such as a tissue specific promoter such that the non-mutated gene of interest is inserted into a specific tissue wherein the mutated gene is expressed in vivo. Additionally, the DNA constructs of the present invention can be used to provide cells or tissues with "beacons", such as receptor molecules, for binding of therapeutic agents in order to provide tissue and cell specificity for the therapeutic agents. Several promoters and exogenous genes can be combined in one vector to produce progressive, controlled, treatments, from a single vector delivery.

In avians, for example, one or more LTR-vector complexes are administered to an avian for the treatment of a viral or bacterial infection/disease including, but not limited to, Colibacillosis (Coliform infections), Mycoplasmosis (CRD, Air sac, Sinusitis), Fowl Cholera, Necrotic Enteritis, Ulcerative Enteritis (Quail disease), Pullorum Disease, Fowl Typhoid, Botulism, Infectious Coryza, Erysipelas, Avian Pox, Newcastle Disease, Infectious Bronchitis, Quail Bronchitis, Lymphoid Leukosis, Marek's Disease (Visceral Leukosis), Infectious Bursal Disease (Gumboro), Avian Encephalomyelitis (AE, Avian Influenza (AI), Avian Leukosis Virus (LLAg, LLAb, ALV-J), Reticuloendotheliosis Virus (REV), Avian Pneumovirus (APV), Chicken Anemia Virus (CAV), Infectious Bronchitis Virus (IBV), Infectious Bursal Disease Virus—Gumboro Disease (IBD, IBD-XR), *Mycoplasma* (MG, MS, MG/MS, MM), Newcastle Disease Virus (NDV, NDV-T), *Ornithobacterium rhinotracheale* (ORT), *Pasteurella multocida* (PM, PM-T), Reovirus (REO), and *Salmonella enteritidis* (SE).

In swine, for example, one or more transposon-based vectors are administered for the treatment of a viral or bacterial infection/disease including, but not limited to, Pseudorabies Virus—Aujeszky's Disease (PRV-V, PRV-S, PRV gl (gE)), Porcine Reproductive and Respiratory Syndrome (PRRS 2XR), Classical Swine Fever Virus (CSFV Ab, CSFV Ag), Swine Influenza (SIV H1N1), *Mycoplasma hyopneumoniae* (*M. hyo.*), and Swine *Salmonella*.

In ruminants, for example, one or more transposon-based vectors are administered for the treatment of a viral or bacterial infection/disease including, but not limited to, Bovine Leukemia Virus (BLV), Infectious Bovine Rhinotracheitis (IBR, IBR gB, IBR gE), *Brucella abortus* (*B. abortus*), *Mycobacterium paratuberculosis*—Johne's Disease (*M. pt.*), *Neospora caninum*, and Bovine Viral Diarrhea Virus (BVDV).

In horses, for example, one or more transposon-based vectors are administered for the treatment of a viral or bacterial infection/disease including, but not limited to, Equine Infectious Anemia (EIA).

Numerous genetic diseases that affect humans are shown in Table 3.

Methods of Administering Compositions Comprising Transposon-Based Vectors to Provide Therapy The compositions of the present invention, comprising a vector, a transfecting reagent and an acceptable carrier may be delivered to a desired location in an animal receiving gene therapy through administration via a selected route. Accordingly, the compositions may be administered in a variety of ways including, but not limited to the following: through a vascular system, a duct system, within the lumen of an organ, into an organ, tissue or cell, into a body cavity, into the cerebrospinal fluid, topically, through the gastrointestinal system, through the reproductive system, through the urinary system, intraperitoneally, and through the respiratory system.

The vector can be administered into the vascular system. In a preferred embodiment, the vector is administered into the cardiovascular system and specifically into one or more chambers of the heart. Administration of the vector into the cardiovascular system and specifically into one or more chambers of the heart, results in the distribution of the vector to the organs and tissues and cells receiving blood supply from the vessel or the heart. In a preferred embodiment, administration of the vector into the left ventricle of the heart results in distribution of the vector to the organs supplied by branches of the aorta, for example the celiac, gonadal, superior (cranial) mesenteric and inferior (caudal) mesenteric arteries. Such distribution targets include the liver, ovary, oviduct and testes, among other organs. Administration through the internal mammary artery transfects secretory cells of the lactating mammary gland to perform a desired function, such as to synthesize and secrete a desired protein or peptide into the milk. Administration through the internal mammary artery would also target breast cancer cells. Administration of the compositions into the artery supplying the ovary or to the fallopian tube to supply those tissues. In this manner, follicles are transfected to create a germline transgenic animal. Alternatively, supplying the compositions through the artery leading to the fallopian tube preferably transfects the epithelial cells. Such transfected epithelial cells manufacture a desired protein or peptide for deposition in the egg white. Administration of the compositions through the portal vein or hepatic artery targets uptake and transformation of hepatic cells. Intravascular administration further includes administration in to any vein, including but not limited to veins in the systemic circulation and veins in the hepatic portal circulation. Intravascular administration further includes administration into the cerebrovascular system, including the carotid arteries, the vertebral arteries and branches thereof.

Intravascular administration may be coupled with methods known to influence the permeability of vascular barriers such as the blood brain barrier and the blood testes barrier, in order to enhance transfection of cells that are difficult to affect through vascular administration. Such methods are known to one of ordinary skill in the art and include use of hyperosmotic agents, mannitol, hypothermia, nitric oxide, alkylglycerols, lipopolysaccharides (Haluska et al., Clin. J. Oncol. Nursing 8(3): 263-267, 2004; Brown et al., Brain Res., 1014: 221-227, 2004; Ikeda et al., Acta Neurochir. Suppl. 86:559-563, 2004; Weyerbrock et al., J. Neurosurg. 99(4):728-737, 2003; Erdlenbruch et al., Br. J. Pharmacol. 139(4):685-694, 2003; Gaillard et al., Microvasc. Res. 65(1):24-31, 2003; Lee et al., Biol. Reprod. 70(2):267-276, 2004)).

Intravascular administration may also be coupled with methods known to influence vascular diameter, such as use of beta blockers, nitric oxide generators, prostaglandins and other reagents that increase vascular diameter and blood flow.

In one embodiment, the animal is an egg-laying animal, and more preferably, an avian, and the transposon-based vectors comprising the polynucleotide cassettes are administered into the vascular system, preferably into the heart. In one embodiment, between approximately 1 and 300 µg, 1 and 200 µg, 5 and 200 µg, or 5 and 150 µg of a transposon-based vector containing the polynucleotide cassette is administered to the vascular system, preferably into the heart. In a chicken, it is preferred that between approximately 1 and 300 µg, or 5 and 200 µg are administered to the vascular system, preferably into the heart, more preferably into the left ventricle. The total injection volume for administration into the left ventricle of a chicken may range from about 10 µl to about 3.0 ml, or from about 100 µl to about 1.5 ml, or from about 200 µl to about 1.0 ml, or from about 200 µl to about 800 µl. It is to be understood that the total injection volume may vary depending on the duration of the injection. Longer injection durations may accommodate higher total volumes. In a quail, it is preferred that between approximately 1 and 200 µg, or 5 and 150 µg are administered to the vascular system, preferably into the heart, more preferably into the left ventricle. The total injection volume for administration into the left ventricle of a quail may range from about 10 µl to about 1.0 ml, or from about 100 µl to about 800 µl, or from about 200 µl to about 600 µl. It is to be understood that the total injection volume may vary depending on the duration of the injection. Longer injection durations may accommodate higher total volumes. The microgram quantities represent the total amount of the vector with the transfection reagent.

Other, non-avian animals will require different volumes and amounts for injection and these values can be extrapolated on a body weight or surface area basis as known to one of ordinary skill in the art. For example, an intravascular administration into a rat may occur through a cannula inserted into the right or left atrium or ventricle and may comprise a volume of from about 0.05 ml to 4 ml containing 1 and 300 µg is injected gradually.

Administration may also occur through non vascular routes. For example, administration through the urethra and into the bladder targets the transitional epithelium of the bladder. Administration through the vagina and cervix targets the lining of the uterus. For example, administration may occur directly into a muscle to transfect striated muscle cells for production of a desired protein.

In one embodiment of the present invention, a transposon-based vector comprising a gene encoding proinsulin is administered to diabetic animals receiving gene therapy for incorporation into liver cells in order to treat or cure diabetes. The specific incorporation of the proinsulin gene into the liver is accomplished by placing the transposase of the transposon-based vector under control of liver-specific promoter, such as the glucose-6-phosphatase promoter (G6P). This approach is useful for treatment of both type I and type II diabetes. The G6P promoter has been shown to be glucose responsive (Arguad, D., et al. 1996, *Diabetes* 45: 1563-1571), and thus, glucose-regulated insulin production is achieved using DNA constructs of the present invention. Integrating a proinsulin gene into liver cells circumvents the problem of destruction of pancreatic islet cells in the course of type 1 diabetes.

In another embodiment, shortly after diagnosis of type I diabetes, the cells of the immune system destroying β-cells of the pancreas are selectively removed using the DNA constructs of the present invention, thus allowing normal β-cells to repopulate the pancreas.

For treatment of type II diabetes, the DNA constructs of the present invention are specifically incorporated into the pancreas by placing the transposase of the transposon-based vector under the control of a pancreas-specific promoter, such as an insulin promoter. In this embodiment, the vector is delivered to a diabetic animal via injection into an artery supplying the pancreas. For delivery, the vector is complexed with a transfection agent. The artery distributes the complex throughout the pancreas, where individual cells receive the vector DNA. Following uptake into the target cell, the insulin promoter is recognized by transcriptional machinery of the cell, the transposase encoded by the vector is expressed, and stable integration of the proinsulin gene occurs. It is expected that a small percentage of the DNA construct would be transported to other tissues, and that these tissues would be transfected. However, these tissues would not be stably transfected due to failure of these other cells to activate the insulin promoter. The DNA would likely be lost when the cell dies or degraded over time.

In addition to the transposon-based vectors described above, the present invention also includes methods of administering the transposon-based vectors to an animal, methods of producing a transgenic animal wherein a gene of interest is incorporated into the germline of the animal and methods of producing a transgenic animal wherein a gene of interest is incorporated into cells other than the germline cells (somatic cells) of the animal. For example, the transposon-based vectors of the present invention are administered to a reproductive organ of an animal via any method known to those of skill in the art. Preferred reproductive organs include a testis, an ovary, an oviduct, a mammary gland, and a fallopian tube.

In some embodiments, a transposon-based vector is directly administered to the reproductive organ. Direct administration encompasses injection into the organ, and in one embodiment, a transposon-based vector is injected into the lumen of the oviduct, and more preferably, the lumen of the magnum or the infundibulum of the oviduct. The transposon-based vectors may additionally or alternatively be placed in an artery supplying the reproductive organ. Administering the vectors to the artery supplying the ovary results in transfection of follicles and oocytes in the ovary to create a germline transgenic animal. Alternatively, supplying the vectors through an artery leading to the oviduct would preferably transfect the tubular gland and epithelial cells. Such transfected cells manufacture a desired protein or peptide for deposition in the egg white. In one embodiment, a transposon-based vector is administered into the lumen of the magnum or the infundibulum of the oviduct and to an artery supplying the oviduct. Indirect administration to the oviduct epithelium may occur through the cloaca. Direct administration into the mammary gland may be achieved through introduction into the duct system of the mammary gland or an artery supplying the mammary gland.

The transposon-based vectors may be administered in a single administration, multiple administrations, continuously, or intermittently. The transposon-based vectors may be administered by injection, via a catheter, an osmotic minipump or any other method. In some embodiments, the transposon-based vector is administered to an animal in multiple administrations, each administration containing the vector and a different transfecting reagent.

The transposon-based vectors may be administered to the animal at any desirable time for gene therapy during the lifetime of the animal.

In one embodiment, between approximately 1 µg and 5 mg, 1 µg and 3 mg, 1 µg and 1 mg, of transposon-based vector DNA is administered to the animal. Intraoviduct administration of the transposon-based vectors of the present invention resulted in incorporation of the gene of interest into the cells of the oviduct as evidenced by a PCR positive signal in the oviduct tissue, demonstrating that the present invention is effective in providing genetic therapy to the animal. In other embodiments, the transposon-based vector is administered to an artery that supplies the oviduct. These methods of administration may also be combined with any methods for facilitating transfection, including without limitation, electroporation, gene guns, injection of naked DNA, and use of dimethyl sulfoxide (DMSO).

According to the present invention, the transposon-based vector is administered in conjunction with an acceptable carrier and/or transfection reagent. Acceptable carriers include, but are not limited to, water, saline, Hanks Balanced Salt Solution (HBSS), Tris-EDTA (TE) and lyotropic liquid crystals. Transfection reagents commonly known to one of ordinary skill in the art that may be employed include, but are not limited to, the following: cationic lipid transfection reagents, cationic lipid mixtures, polyamine reagents, liposomes and combinations thereof; SUPERFECT®, Cytofectene, BioPORTER®, GenePORTER®, NeuroPORTER®, and perfectin from Gene Therapy Systems; lipofectamine, cellfectin, DMRIE-C oligofectamine, and PLUS reagent from InVitrogen; Xtreme gene, fugene, DOSPER and DOTAP from Roche; Lipotaxi and Genejammer from Strategene; and Escort from SIGMA. In one embodiment, the transfection reagent is SUPERFECT®. The ratio of DNA to transfection reagent may vary based upon the method of administration. In one embodiment, the transposon-based vector is administered to the oviduct and the ratio of DNA to transfection reagent can be from 1:1.5 to 1:15, preferably 1:2 to 1:5, all expressed as wt/vol. Transfection may also be accomplished using other means known to one of ordinary skill in the art, including without limitation electroporation, gene guns, injection of naked DNA, and use of dimethyl sulfoxide (DMSO).

Depending upon the cell or tissue type targeted for transfection, the form of the transposon-based vector may be important. Plasmids harvested from bacteria are generally closed circular supercoiled molecules, and this is the preferred state of a vector for gene delivery because of the ease of preparation. In some instances, transposase expression and insertion may be more efficient in a relaxed, closed circular configuration or in a linear configuration. In still other instances, a purified transposase protein may be co-injected with a transposon-based vector containing the gene of interest for more immediate insertion. This could be accomplished by using a transfection reagent complexed with both the purified transposase protein and the transposon-based vector.

Testing for and Breeding Animals Carrying the Transgene

Following administration of a transposon-based vector to an animal receiving gene therapy, DNA is extracted from the animal to confirm integration of the gene of interest. Advantages provided by the present invention include the high rates of integration, or incorporation, and transcription of the gene of interest when administered to a bird via an intraoviduct or intraovarian route (including intraarterial administrations to arteries leading to the oviduct or ovary). The construct of FIG. 2, when administered to Japanese quail hens, resulted in expression of the fusion peptide in the oviduct cells and subsequent secretion and deposition in the egg white. Assaying of the egg white on and SDS PAGE gel demonstrated the presence of the expressed protein. The sequence of the fusion protein was verified by MALDI-TOF analysis by an independent third party. The proinsulin/ENT TAG protein from a transgenic hen was isolated following ammonium sulfate precipitation and ion exchange chromatography. The transposon-based vector was successfully administered to a hen, and the gene of interest successfully integrated. The protein encoded by the gene of interest was produced and deposited in egg white produced by the transgenic hen.

Actual frequencies of integration may be estimated both by comparative strength of the PCR signal, and by histological evaluation of the tissues by quantitative PCR. Another method for estimating the rate of transgene insertion is the so-called primed in situ hybridization technique (PRINS). This method determines not only which cells carry a transgene of interest, but also into which chromosome the gene has inserted, and even what portion of the chromosome. Briefly, labeled primers are annealed to chromosome spreads (affixed to glass slides) through one round of PCR, and the slides are then developed through normal in situ hybridization procedures. This technique combines the best features of in situ PCR and fluorescence in situ hybridization (FISH) to provide distinct chromosome location and copy number of the gene in question. The 28s rRNA gene will be used as a positive control for spermatogonia to confirm that the technique is functioning properly. Using different fluorescent labels for the transgene and the 28s gene causes cells containing a transgene to fluoresce with two different colored tags.

Breeding experiments are also conducted to determine if germline transmission of the transgene has occurred. In a general bird breeding experiment performed according to the present invention, each male bird was exposed to 2-3 different adult female birds for 3-4 days each. This procedure was continued with different females for a total period of 6-12 weeks. Eggs are collected daily for up to 14 days after the last exposure to the transgenic male, and each egg is incubated in a standard incubator. The resulting embryos are examined for transgene presence at day 3 or 4 using PCR. It is to be understood that the above procedure can be modified to suit animals other than birds and that selective breeding techniques may be performed to amplify gene copy numbers and protein output.

Production of Desired Proteins or Peptides in Egg White

In one embodiment, the transposon-based vectors of the present invention may be administered to a bird receiving gene therapy for production of desired proteins or peptides in the egg white. These transposon-based vectors preferably contain one or more of an ovalbumin promoter, an ovomucoid promoter, an ovalbumin signal sequence and an ovomucoid signal sequence. Oviduct-specific ovalbumin promoters are described in B. O'Malley et al., 1987. EMBO J., vol. 6, pp. 2305-12; A. Qiu et al., 1994. Proc. Nat. Acad. Sci. (USA), vol. 91, pp. 4451-4455; D. Monroe et al., 2000. Biochim. Biophys. Acta, 1517 (1):27-32; H. Park et al., 2000. Biochem., 39:8537-8545; and T. Muramatsu et al., 1996. Poult. Avian Biol. Rev., 6:107-123. Examples of transposon-based vectors designed for production of a desired protein in an egg white are shown in FIGS. 2 and 3.

Production of Desired Proteins or Peptides in Egg Yolk

The present invention is particularly advantageous for production of recombinant peptides and proteins of low solubility in the egg yolk. Such proteins include, but are not limited to, membrane-associated or membrane-bound proteins, lipophilic compounds; attachment factors, receptors, and components of second messenger transduction machinery. Low solubility peptides and proteins are particularly challenging to produce using conventional recombinant protein production techniques (cell and tissue cultures) because they aggregate in water-based, hydrophilic environments. Such aggregation necessitates denaturation and re-folding of the recombinantly-produced proteins, which may deleteriously affect their structure and function. Moreover, even highly soluble recombinant peptides and proteins may precipitate and require denaturation and renaturation when produced in sufficiently high amounts in recombinant protein production systems. The present invention provides an advantageous resolution of the problem of protein and peptide solubility during production of large amounts of recombinant proteins.

In one embodiment of the present invention wherein germline transfection is obtained via intraovarian administration of the transposon-based vector, deposition of a desired protein into the egg yolk is accomplished in offspring by attaching a sequence encoding a protein capable of binding to the yolk vitellogenin receptor to a gene of interest that encodes a desired protein. This transposon-based vector can be used for the receptor-mediated uptake of the desired protein by the oocytes. In a preferred embodiment, the sequence ensuring the binding to the vitellogenin receptor is a targeting sequence of a vitellogenin protein. The invention encompasses various vitellogenin proteins and their targeting sequences. In a preferred embodiment, a chicken vitellogenin protein targeting sequence is used, however, due to the high degree of conservation among vitellogenin protein sequences and known cross-species reactivity of vitellogenin targeting sequences with their egg-yolk receptors, other vitellogenin targeting sequences can be substituted. One example of a construct for use in the transposon-based vectors of the present invention and for deposition of an insulin protein in an egg yolk is a transposon-based vector containing a vitellogenin promoter, a vitellogenin targeting sequence, a TAG sequence, a pro-insulin sequence and a synthetic polyA sequence. The present invention includes, but is not limited to, vitellogenin targeting sequences residing in the N-terminal domain of vitellogenin, particularly in lipovitellin I. In one embodiment, the vitellogenin targeting sequence contains the polynucleotide sequence of SEQ ID NO:28. In a preferred embodiment, the transposon-based vector contains a transposase gene operably-linked to a constitutive promoter and a gene of interest operably-linked to a liver-specific promoter and a vitellogenin targeting sequence.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Preparation of Transposon-Based Vector pTnMod

A vector was designed for inserting a desired coding sequence into the genome of eukaryotic cells, given below as SEQ ID NO:7. The vector of SEQ ID NO:7, termed pTnMod, was constructed and its sequence verified.

This vector employed a cytomegalovirus (CMV) promoter. A modified Kozak sequence (ACCATG) (SEQ ID NO:8) was added to the promoter. The nucleotide in the wobble position in nucleotide triplet codons encoding the first 10 amino acids of transposase was changed to an adenine (A) or thymine (T), which did not alter the amino acid encoded by this codon. Two stop codons were added and a synthetic polyA was used to provide a strong termination sequence. This vector uses a promoter designed to be active soon after entering the cell (without any induction) to increase the likelihood of stable integration. The additional stop codons and synthetic polyA insures proper termination without read through to potential genes downstream.

The first step in constructing this vector was to modify the transposase to have the desired changes. Modifications to the transposase were accomplished with the primers High Efficiency forward primer (Hef) Altered transposase (ATS)-Hef 5' ATCTCGAGACCATGTGTGAACT TGATATTTTACATGATTCTCTTTACC 3' (SEQ ID NO:42) and Altered transposase-High efficiency reverse primer (Her) 5' GATTGATCATTATCATAATTTC-CCCAAAGCGTAACC 3' (SEQ ID NO:43, a reverse complement primer). The sequence ACCATG (SEQ ID NO:8) contains the Kozak sequence and start codon for the transposase and the underlined bases represent changes in the wobble position to an A or T of codons for the first 10 amino acids (without changing the amino acid coded by the codon). Primer ATS-Her (SEQ ID NO:43) contains an additional stop codon TAA in addition to native stop codon TGA and adds a Bcl I restriction site to allow directional cloning. These primers were used in a PCR reaction with pTnLac (p defines plasmid, to defines transposon, and lac defines the beta fragment of the lactose gene, which contains a multiple cloning site) as the template for the transposase and a FailSafe™ PCR System (which includes enzyme, buffers, dNTP's, $MgCl_2$ and PCR Enhancer; Epicentre Technologies, Madison, Wis.). Amplified PCR product was electrophoresed on a 1% agarose gel, stained with ethidium bromide, and visualized on an ultraviolet transilluminator. A band corresponding to the expected size was excised from the gel and purified from the agarose using a Zymo Clean Gel Recovery Kit (Zymo Research, Orange, Calif.). Purified DNA was digested with restriction enzymes Xho I (5') and Bcl I (3') (New England Biolabs, Beverly, Mass.) according to the manufacturer's protocol. Digested DNA was purified from restriction enzymes using a Zymo DNA Clean and Concentrator kit (Zymo Research).

Plasmid gWhiz (Gene Therapy Systems, San Diego, Calif.) was digested with restriction enzymes Sal I and BamH I (New England Biolabs), which are compatible with Xho I and Bcl I, but destroy the restriction sites. Digested gWhiz was separated on an agarose gel, the desired band excised and purified as described above. Cutting the vector in this manner facilitated directional cloning of the modified transposase (mATS) between the CMV promoter and synthetic polyA.

To insert the mATS between the CMV promoter and synthetic polyA in gWhiz, a Stratagene T4 Ligase Kit (Stratagene, Inc. La Jolla, Calif.) was used and the ligation set up according to the manufacturer's protocol. Ligated product was transformed into E. coli Top10 competent cells (Invitrogen Life Technologies, Carlsbad, Calif.) using chemical transformation according to Invitrogen's protocol. Transformed bacteria were incubated in 1 ml of SOC (GIBCO BRL, CAT#15544-042) medium for 1 hour at 37° C. before being spread to LB (Luria-Bertani media (broth or agar)) plates supplemented with 100 µg/ml ampicillin (LB/amp plates). These plates were incubated overnight at 37° C. and resulting colonies picked to LB/amp broth for overnight growth at 37° C. Plasmid DNA was isolated using a modified alkaline lysis protocol (Sambrook et al., 1989), electrophoresed on a 1% agarose gel, and visualized on a U.V. transilluminator after ethidium bromide staining. Colonies producing a plasmid of the expected size (approximately 6.4 kbp) were cultured in at least 250 ml of LB/amp broth and plasmid DNA harvested using a Qiagen Maxi-Prep Kit (column purification) according to the manufacturer's protocol (Qiagen, Inc., Chatsworth, Calif.). Column purified DNA was used as template for sequencing to verify the changes made in the transposase were the desired changes and no further changes or mutations occurred due to PCR amplification. For sequencing, Perkin-Elmer's Big Dye Sequencing Kit was used. All samples were sent to the Gene Probes and Expression Laboratory (LSU School of Veterinary Medicine) for sequencing on a Perkin-Elmer Model 377 Automated Sequencer.

Once a clone was identified that contained the desired mATS in the correct orientation, primers CMVf-NgoM IV and Syn-polyA-BstE II were used to PCR amplify the entire CMV promoter, mATS, and synthetic polyA for cloning upstream of the transposon in pTnLac. The PCR was conducted with FailSafe™ as described above, purified using the Zymo Clean and Concentrator kit, the ends digested with NgoM IV and BstE II (New England Biolabs), purified with the Zymo kit again and cloned upstream of the transposon in pTnLac as described below.

Plasmid pTnLac was digested with NgoM IV and BstE II to remove the ptac promoter and transposase and the fragments separated on an agarose gel. The band corresponding to the vector and transposon was excised, purified from the agarose, and dephosphorylated with calf intestinal alkaline phosphatase (New England Biolabs) to prevent self-annealing. The enzyme was removed from the vector using a Zymo DNA Clean and Concentrator-5. The purified vector and CMVp/mATS/polyA were ligated together using a Stratagene T4 Ligase Kit and transformed into E. coli as described above.

Colonies resulting from this transformation were screened (mini-preps) as describe above and clones that were the correct size were verified by DNA sequence analysis as described above. The vector was given the name pTnMod (SEQ ID NO:7) and includes the following components:

Base pairs 1-130 are a remainder of F1(−) on from pBluescriptII sk(−) (Stratagene), corresponding to base pairs 1-130 of pBluescriptII sk(−).

Base pairs 131-132 are a residue from ligation of restriction enzyme sites used in constructing the vector.

Base pairs 133-1777 are the CMV promoter/enhancer taken from vector pGWiz (Gene Therapy Systems), corresponding to bp 229-1873 of pGWiz. The CMV promoter was modified by the addition of an ACC sequence upstream of ATG.

Base pairs 1778-1779 are a residue from ligation of restriction enzyme sites used in constructing the vector.

Base pairs 1780-1785 are the Kozak sequence of SEQ ID NO: 8, and base pairs 1783-2987 are the coding sequence for the transposase, modified from Tn10 (GenBank accession J01829) by optimizing codons for stability of the transposase mRNA and for the expression of protein. More specifically, in each of the codons for the first ten amino acids of the transposase, G or C was changed to A or T when such a substitution would not alter the amino acid that was encoded.

Base pairs 2988-2993 are two engineered stop codons.

Base pair 2994 is a residue from ligation of restriction enzyme sites used in constructing the vector.

Base pairs 2995-3410 are a synthetic polyA sequence taken from the pGWiz vector (Gene Therapy Systems), corresponding to bp 1922-2337 of 10 pGWiz.

Base pairs 3415-3718 are non-coding DNA that is residual from vector pNK2859.

Base pairs 3719-3761 are non-coding λ DNA that is residual from pNK2859.

Base pairs 3762-3831 are the 70 bp of the left insertion sequence recognized by the transposon Tn10.

Base pairs 3832-3837 are a residue from ligation of restriction enzyme sites used in constructing the vector.

Base pairs 3838-4527 are the multiple cloning site from pBluescriptII sk(20), corresponding to bp 924-235 of pBluescriptII sk(−). This multiple cloning site may be used to insert any coding sequence of interest into the vector.

Base pairs 4528-4532 are a residue from ligation of restriction enzyme sites used in constructing the vector.

Base pairs 4533-4602 are the 70 bp of the right insertion sequence recognized by the transposon Tn 10.

Base pairs 4603-4644 are non-coding λ DNA that is residual from pNK2859.

Base pairs 4645-5488 are non-coding DNA that is residual from pNK2859.

Base pairs 5489-7689 are from the pBluescriptll sk(−) base vector—(Stratagene, Inc.), corresponding to bp 761-2961 of pBluescriptll sk(−).

Completing pTnMod is a pBlueScript backbone that contains a colE I origin of replication and an antibiotic resistance marker (ampicillin).

It should be noted that all non-coding DNA sequences described above can be replaced with any other non-coding DNA sequence(s). Missing nucleotide sequences in the above construct represent restriction site remnants.

All plasmid DNA was isolated by standard procedures. Briefly, *Escherichia coli* containing the plasmid was grown in 500 mL aliquots of LB broth (supplemented with an appropriate antibiotic) at 37° C. overnight with shaking. Plasmid DNA was recovered from the bacteria using a Qiagen Maxi-Prep kit (Qiagen, Inc., Chatsworth, Calif.) according to the manufacturer's protocol. Plasmid DNA was resuspended in 500 µL of PCR-grade water and stored at −20° C. until used.

EXAMPLE 2

Transposon-Based Vector pTnMCS

Another transposon-based vector was designed for inserting a desired coding sequence into the genome of eukaryotic cells. This vector was termed pTnMCS and its constituents are provided below. The sequence of the pTnMCS vector is provided in SEQ ID NO:6. The pTnMCS vector contains an avian optimized polyA sequence operably-linked to the transposase gene. The avian optimized polyA sequence contains approximately 40 nucleotides that precede the A nucleotide string. Bp 1-130 Remainder of F1 (−) ori of pBluescriptII sk(−) (Stratagene) bp1-130 Bp 133-1777 CMV promoter/enhancer taken from vector pGWIZ (Gene Therapy Systems) bp 229-1873

Bp 1783-2991 Transposase, from Tn10 (GenBank accession #J01829) bp 108-1316
Bp 2992-3344 Non coding DNA from vector pNK2859
Bp 3345-3387 Lambda DNA from pNK2859
Bp 3388-3457 70 bp of IS10 left from Tn10
Bp 3464-3670 Multiple cloning site from pBluescriptII sk(−), thru the XmaI site bp 924-718
Bp 3671-3715 Multiple cloning site from pBluescriptII sk(−), from the XmaI site thru the XhoI site. These base pairs are usually lost when cloning into pTnMCS bp 717-673
Bp 3716-4153 Multiple cloning site from pBluescriptII sk(−), from the XhoI site bp 672-235
Bp 4159-4228 70 bp of IS10 right from Tn10
Bp 4229-4270 Lambda DNA from pNK2859
Bp 4271-5114 Non-coding DNA from pNK2859
Bp 5115-7315 pBluescript sk (−) base-vector (Stratagene, Inc.) bp 761-2961.

EXAMPLE 3

Gene Therapy to Treat Cancer in an Animal
Preparation of the Transposon-Based Vector The following genes were cloned into the transposon-based vector of the present invention: an SV40 promoter linked to the preprosequence of cecropin B together with either a gene of interest encoding Phor14:beta human chorionic gonadotropin (bHCG), a gene of interest encoding gonadotropin releasing hormone (GnRH):Phor 11, or a gene of interest encoding GnRH:Phor 14, each linked to a cecropin B poly A. The Phor peptides are lytic peptides. In this manner, three different vectors were created: 1) pTnPhor14:bHCG; 2) pTnGnRH:Phor 11; and, 3) pTnGnRH:Phor 14. The base vector used was pBTnLac. The SV40 promoter is a constitutive promoter expressed at a moderate level. The cecropin B prepro peptide was selected to permit a peptide to be transported out of the cell. The cecropin B poly A was selected to terminate mRNA synthesis. These vectors in turn stimulate production of the fusion peptides, GnRH:Phor 11 (SEQ ID NO:44), GnRH:Phor 14 (SEQ ID NO:45), and Phor14:bHCG (SEQ ID NO:46). These transposon-based vectors were designed to provide an alternative to conventional chemotherapy in animals with tumors that express a receptor for luteinizing hormone (LH) or GnRH at their surface, for example prostatic, ovarian, breast, pancreatic and some small cell lung carcinomas.

Mice, fish, cats and dogs have received these compositions without any adverse side effects. Temporary sterility was induced in these animals as evidenced by a disrupted reproductive cycle.

The goal of this gene therapy was to administer the transposon-based vector complexed with a transfecting agent to the animal through any desired route (for example intravenous, intraperitoneal, intraarterial, or intramuscular) so that the animal makes the fusion protein. Next, the cells of the animal that expressed a receptor for LH or GnRH recognized and bound the LH or GnRH component of the fusion peptide and delivered the fusion peptide containing the lytic peptide component to the cell, eventually resulting in lysis of the cell.

This approach to gene therapy permits very specific targeting of cells for destruction since cells expressing receptors specific for a ligand are affected without affecting other cells as in conventional chemotherapy or radiotherapy. Further, this approach permits sustained delivery of the fusion peptides over time since the transgene is stably incorporated.

Use of the Transposon-based Vector in Gene Therapy for Treatment of Cancer in a Dog and in a Cat A dog with breast cancer metastasized throughout the body was treated. An aged female retriever of about 85 pounds body weight was diagnosed with widespread inflammatory mammary carcinoma. The initial diagnosis was confirmed with a skin biopsy of nodular lesions on the left lateral chest wall. The biopsy demonstrated tumor nodules surrounded by fibrous tissue and tumor emboli within dermal lymphatic vessels. The tumor was composed of large, irregular, darkly blue stained cells with nuclear atypia and a high mitotic rate. The dog was administered the genetic constructs encoding for SEQ ID NO: 45 and SEQ ID NO: 46, i.v., at a dose of 50 ug of each construct in about 150 ul of transfection reagent (Superfect). Ten days later the dog suddenly died. Within three hours, the skin lesion near the original biopsy site was removed and fixed. Histological analysis of sections from this biopsy revealed advanced and severe necrosis of the tumor cells both within the fibrous lesions and within the lymphatic vessels. Adjacent, normal non-neoplastic cells and tissues were non-necrotic. The death of tumor cells was estimated at more than 90%.

A cat with breast cancer metastasized throughout the body was treated. The cat was diagnosed with widespread inflammatory mammary carcinoma. The initial diagnosis was confirmed with a skin biopsy of nodular lesions. The cat was administered the genetic constructs encoding for SEQ ID NO: 45 and SEQ ID NO: 46, i.v. at a dose of 50 ug of each construct in about 150 ul of transfection reagent (Superfect). A subsequent histological analysis of sections from this biopsy revealed advanced and severe necrosis of the tumor cells both within the fibrous lesions and within the lymphatic vessels. Adjacent, normal non-neoplastic cells and tissues were non-necrotic.

The results demonstrate the efficiency of the gene therapy method of the present invention to treat cancer in an animal.

EXAMPLE 4

Development of a Vector for Tissue-specific Insulin Gene Incorporation into Animal Liver FIG. 6 shows a scheme of a pTnMod-based vector for targeting an insulin gene into the liver. Using transposase (ATS) under control of liver-specific promoter, such as liver glucose-6-phosphatase (G6P) promoter, allows for tissue-specific incorporation of the insulin gene in the liver. The insulin gene is also placed under control of a glucose-6 phosphatase (G6P) promoter.

The G6P promoter is cloned from rat genomic liver DNA. Rat genomic liver DNA is prepared according to procedures known to one of ordinary skill in the art. The promoter is cloned by amplifying the gene sequence using specific primers in a PCR reaction using methods known to one of ordinary skill in the art.

Alternatively, rat G6P promoter sequence is deduced from rat G6P gene untranslated upstream region provided in GenBank accession number U57552.1 and a corresponding synthetic oligonucleotide is prepared by methods known to one of ordinary skill in the art, preferably by any one of a number of commercial suppliers of synthetic oligonucleotides.

The gene encoding human proinsulin is amplified from human cDNA according to methods known in the art, for example, by using PCR with the primers specific for a proinsulin gene sequence, which is shown in SEQ ID NO:29. Briefly, total mRNA is isolated from a human pancreas according to procedures standard in the art. This mRNA is used to produce cDNA according to procedures standard in the art. Alternatively, the promoter sequence is amplified by PCR from a commercially available human pancreatic cDNA library, such as the one supplied by Clontech Laboratories, Inc. under 2000 catalog number 7115-1, Human Pancreas QUICK-Clone cDNA.

Proinsulin is PCR-amplified from cDNA using specific primers designed in accordance with the proinsulin DNA sequence. The gene encoding proinsulin is cloned into the multiple cloning site (MCS) of pGWiz downstream of the G6P promoter sequence and upstream of the polyadenylation sequence (polyA).

Each of the identified components is sequenced, and cloned into pTnMod according to the scheme shown in FIG. 6. Transposase (ATS) of the pTnMod vector is also placed under the control of the G6P promoter, which is obtained as described above, by subcloning G6P promoter sequence upstream of the pTnMod transposase sequence. Insertion sequences are denoted IS.

Any other desired components are prepared and incorporated into the vector by methods known to one of ordinary skill in the art. This vector is termed pTnModIns. Sufficient amounts of substantially pure TnModIns DNA are prepared using methods common in the art.

EXAMPLE 5

Treatment of Rats with the Vector for Tissue-specific Insulin Gene Incorporation Diabetic rats are obtained made diabetic by administering the drug streptozotocin (Zanosar; Upjohn, Kalamazoo, Mich.) at approximately 200 mg/kg.

The rats are bred and maintained according to standard procedures. pTnModIns DNA, an appropriate carrier, and, optionally, a transfection agent, are injected into rats' singhepatic (if using G6P) artery with the purpose of stable transformation. Incorporation of the insulin gene into the rat genome and levels of insulin expression are ascertained by a variety of methods known in the art. Blood and tissue samples from live or sacrificed animals are tested. A combination of PCR, Southern and Northern blots, in-situ hybridization and related nucleic acid analysis methods are used to determine incorporation of the vector-derived proinsulin DNA and levels of transcription of the corresponding mRNA in various organs and tissues of the rats. A combination of SDS-PAGE gels, Western Blot analysis, radioimmunoassay, and ELISA and other methods known to one of ordinary skill in the art are used to determine the presence of insulin and the amount produced. Additional transfections of pTnModIns are used to increase protein expression if the initial amounts of the expressed insulin are not satisfactory, or if the level of expression tapers off. The physiological condition of the rats is closely examined post-transfection to register positive or any negative effects of the gene therapy. Animals are examined over extended periods of time post-transfection in order to monitor the stability of gene incorporation and protein expression.

EXAMPLE 6

Intracardiac Injection of a Transposon-based Vector for Gene Therapy and Production of Transgenic Quail Direct cardiac injection coupled with a transposon-based vector was used to provide direct incorporation into either liver, oviduct, or ovaries and progenitor cells of each. The technique may also be used to transform the progenitor cells (spermatogonia) in the testes to give rise to transgenic sperm. Stable incorporation of the vector DNA in progenitor cells results in long term production of transgenic liver cells, ova and oviduct cells, including tubular gland cells, and sperm; presumably for the life of the bird.

Five Japanese quail from Louisiana State University (LSU) stock and five from Bull Run stock were anesthetized and injected in the left ventricle of the heart in with 20 μg of the transposon-based vector and transfection reagent in a total volume of 0.35 ml. A needle approximately ⅝ inches (25 gauge) in length was used for injections of LSU quail. A needle approximately 1 inch (22 gauge) in length was used for injections of Bull Run quail. The needles were connected to a 1 ml tuberculin syringe containing the transfection mixture. Birds were held in the hand with the keel up. Feathers in the area of the left breast were grasped and a few down feathers removed over the injection site. The area sprayed with ethanol.

The injector placed his left hand over the bird with the tip of the forefinger placed on the anterior tip of the keel. The thumb was used to palpate the triangle-shaped, posterior end of the caudolateral process of the sternum. The caudolateral process was followed forward to where it joined the body of the sternum. This marked the U shaped bony border of the lateral notch. The U of the lateral notch is formed by the thoracic process and the caudolateral process. While maintaining the thumb in the lateral notch, an imaginary line was drawn straight down from the forefinger. Another imaginary line was drawn at the angle of the caudolateral process from the tip of the thumb forward. The site where the needle was placed was the intersection of these lines. This is approximately 2 cm towards the bird's head from the tip of the thumb.

The needle and syringe were held parallel to the table. The needle was inserted into the superficial pectoralis muscle. Without completely withdrawing the needle, it was repositioned slightly to one side or the other until an intercostal space was found.

The needle was placed into the left breast muscle at about a 45° angle. When the needle was about halfway in, the needle hit the sternum. Next, the needle was partially removed and repositioned at a steeper angle until the sternum was no longer encountered. At this angle the needle dropped into the left ventricle of the heart. A flash of blood appeared in the syringe and pulsed in the hub at the rate of the heartbeat. The plunger on the syringe was slowly depressed. If there was an air bubble above the solution inside the syringe, the plunger was stopped before the air was pushed out into the blood. The needle was removed and disposed in a biohazard sharps container. The bird was returned to its cage and monitored for any signs of distress. (See A Color Atlas of Avian Anatomy. John McLelland. W.B. Saunders Company, 1991 for view of the anatomy of this area).

The vector CMVp/pp/HC/ProLys/LC/CPA (SEQ ID NO: 47), which encodes monoclonal antibody RM-2, was injected into the left ventricle of female Japanese quail. These birds were held for 2 days post-injection and sacrificed by cervical dislocation. Immediately after sacrifice, the visceral cavity of each bird was opened and a piece of liver, ovary, and oviduct was removed. For oviduct, a section from the magnum was removed and scissors were used to make a longitudinal cut that opened the tube and allowed it to lay flat. Once the luminal folds were exposed, the tops of the folds were removed and used for tissue extraction. Using the tops of these folds ensured that the most abundant cell type was the tubular gland cell.

Approximately 5 mg of each tissue type was used for genomic DNA isolation using a Qiagen Genomic DNA isolation kit. DNA was quantified and used in a PCR reaction with primers HC-1 and HC-4 that amplify a section of the human IgG heavy chain. The vector used for these injections served as a positive control in the PCR reactions. One LSU bird (Bird 2211) and one Bull Run bird (bird 2895) did not receive an injection and were used as negative controls.

In order to determine if gene incorporation (transposition) was occurring, instead of maintenance of the vector, PCR was conducted using a primer anchored in the gene of interest and the transposase. The result was a greatly reduced PCR reaction when compared to the PCR result from the heavy chain indicating the vector was being destroyed while the target gene was being mainted in the recipient chromosome.

PCR was conducted on the liver of quail injected in the left ventricle with a transposon-based vector encoding for the monoclonal MCS(CMVp/pp/HC/ProLys/LC/CPA) SEQ ID NO:48. Primers designed to the heavy chain of the monoclonal resulted in the correct PCR fragment in all of the injected birds and the positive vector control. All control birds, PCR controls, and kit controls resulted in a negative PCR reaction. This PCR reaction proved DNA uptake by the liver in birds that received a cardiac injection. One bird was slightly weaker on an oviduct sample. These results clearly demonstrate DNA presence in high quantities two days post-cardiac injection.

In order to determine if transposition occurred, the same quantity of DNA was used in the PCR reaction containing primers HC 1 and HC 4 as was used in the PCR reaction containing primers mATS3'F and mATS5'R (these primers amplify a segment of DNA within the transposase). If no transposition occurred, then the bands in each reaction would be very similar in intensity. If transposition occurred, then the bands would not be similar. In order to make sure there was not a problem with the buffer chosen, 3 buffers from an optimization kit were used. Due to the band intensity from the initial PCR, the number of cycles was decreased from 45 to 30 in order to detect any small differences that might occur.

As seen in the transposition PCR, the band corresponding to the transposase was present, but at a concentration much less than the heavy chain fragment that was amplified. The results also demonstrate that the transposase is degraded which the gene encoding for the heavy chain is stably incorporated. This indicates that transposition has occurred and that the majority of the amplicon was due to copies integrated into the quail genome. Using such a delivery system combined with a transposon-based vector allows rapid expression of a gene for protein production in the liver or oviduct, or allows production of transgenic hens and roosters equivalent to G2 offspring if a traditional route of transfecting one animal and crossing to increase gene copy number is used.

EXAMPLE 7

Intracardiac Injection of a Transposon-based Vector for Gene Therapy and Production of Proinsulin in Transgenic Chickens A total of 6 mature white leghorn hens were anesthetized and injected into the left ventricle of the heart with 1 ml total volume (consisting 50 μg of DNA, 150 μl of Superfect supplemented with HBSS to 1 ml). The methods are similar to those described in the preceding example for quail.

Briefly, a needle approximately 1 inch (22 gauge) in length was used for injections of chickens. The needles were connected to a 1 ml tuberculin syringe containing the transfection mixture. Birds were held at the base of the wings on a table. Feathers in the area of the feather track about halfway down the breast were grasped and a few down feathers removed over the injection site. The area sprayed with ethanol.

The injector placed his left hand over the bird with the tip of the forefinger placed on the anterior tip of the keel. The thumb was used to palpate the triangle-shaped, posterior end of the caudolateral process of the sternum. The caudolateral process was followed forward to where it joined the body of the sternum. This marked the U shaped bony border of the lateral notch. The U of the lateral notch is formed by the thoracic process and the caudolateral process. While maintaining the thumb in the lateral notch, an imaginary line was drawn straight down from the forefinger. Another imaginary line was drawn at the angle of the caudolateral process from the tip of the thumb forward. The site where the needle was placed was the intersection of these lines. This is approximately 2 cm towards the bird's head from the tip of the thumb.

The needle and syringe were held parallel to the table. The needle was inserted into the superficial pectoralis muscle. Without completely withdrawing the needle, it was repositioned slightly to one side or the other until an intercostal space was found.

The needle was placed into the left breast muscle at about a 45° angle. When the needle was about halfway in, the needle hit the sternum. Next, the needle was partially removed and repositioned at a steeper angle until the sternum was no longer encountered. At this angle the needle dropped into the left ventricle of the heart. A flash of blood appeared in the syringe and pulsed in the hub at the rate of the heartbeat. The plunger on the syringe was slowly depressed. If there was an air bubble above the solution inside the syringe, the plunger was stopped before the air was pushed out into the blood. The needle was removed and disposed in a biohazard sharps container. The bird was returned to its cage and monitored for any signs of distress. (See A Color Atlas of Avian Anatomy. John McLelland. W.B. Saunders Company, 1991 for view of the anatomy of this area).

The vector SEQ ID NO: 49 encoded for chicken ovalbumin::ent Tag::proinsulin fusion protein (Vector: pTnMCS (ChOVep/OVg'/ent/pro-ins/syn poly A) (Clone MCS6). Twenty-four hours post-injection, two birds were sacrificed and liver, ovary and oviduct tissue was removed from each bird. Genomic DNA was extracted from each tissue as described previously. PCR was conducted and a sample of that reaction was electrophoresed on a 2% gel. The remaining 4 chickens are laying eggs that are currently being evaluated for the presence of the fusion protein.

PCR was conducted on DNA isolated from the liver, oviduct and ovary of two chickens (2004, 2005) injected in the left ventricle with a transposon-based vector encoding for ovalbumin::ent Tag::proinsulin fusion protein SEQ ID NO:49. The result was a positive PCR reaction from each DNA sample, regardless of the tissue type and the vector control. All kit and PCR controls were negative indicating no contamination had occurred. The results show band amplified by PCR that indicate that the gene encoding for proinsulin is present in the liver, ovary and oviduct of each of the two chickens examined.

SEQ ID NO: 49 pTnMCS(Chicken OVep+OVg'+ENT+ proins+syn polyA) was constructed as follows:
Bp 1-3670 from-vector pTnMCS, bp 1-3670
Bp 3676-4350 Chicken Ovalbumin enhancer taken from GenBank accession # S82527.1 bp 1-675
Bp 4357-5692 Chicken Ovalbumin promoter taken from GenBank accession # J00895-M24999 bp 1-1336
Bp 5699-6917 Chicken Ovalbumin gene from GenBank Accession # V00383.1 bp
2-1220. (This sequence includes the 5'UTR, containing putative cap site, bp 5699-5762.)
Bp 6924-7073 Synthetic spacer sequence and hairpin loop of HIV gp41 with an added enterokinase cleavage site
Bp 7074-7334 Human proinsulin GenBank Accession # NM000207 bp 117-377
Bp 7335-7379 Spacer DNA, derived as an artifact from the cloning vectors pTOPO Blunt II (Invitrogen) and gWIZ (Gene Therapy Systems)
Bp 7380-7731 Synthetic polyA from the cloning vector gWIZ (Gene Therapy Systems) bp 1920-2271
Bp 7733-11332 from vector pTnMCS, bp 3716-7315

All patents, publications and abstracts cited above are incorporated herein by reference in their entirety, including U.S. provisional patent applications Ser. Nos. 60/532,504, 60/565,371 and 60/592,098, and PCT patent applications PCT/US03/41261, PCT/US03/41269, and PCT/US03/41335. It should be understood that the foregoing relates only to preferred embodiments of the present invention and that numerous modifications or alterations may be made therein without departing from the spirit and the scope of the present invention as defined in the following claims.

TABLE 1

|  | Promoter | Ref. | Function/comments |
|---|---|---|---|
| Reproductive tissue | | | |
| testes, spermatogenesis | SPATA4 | 1 | constitutive 30 d after birth in rat |
| placenta, glycoprotein | ERVWE1 | 2 | URE, Upstream Regulatory Element is tissue spec. enhancer |
| breast epithelium and breast cancer | mammaglobin | 6 | specific to breast epithelium and cancer |
| prostate | EPSA | 17 | enhanced prostate-specific antigen promoter |
| testes | ATC | 25 | AlphaT-catenin specific for testes, skeletal, brain cardiomyocytes |
| prostate | PB | 67 | probasin promoter |
| Vision | | | |
| rod/cone | mCAR | 3 | cone photoreceptors and pinealocytes |
| retina | ATH5 | 15 | functions in retinal ganglia and precursors |
| eye, brain | rhodopsin | 27 | |
| kertocytes | keratocan | 42 | specific to the corneal stroma |
| retina | RPE65 | 59 | |
| Muscle | | | |
| vascular smooth muscle | TFPI | 13 | Tissue Factor Pathway Inhibitor - low level expression in endothelial and smooth muscle cells of vascular system |
| cardiac specific | MLC2v | 14, 26 | ventricular myosin light chain |
| cardiac | CAR3 | 18 | BMP response element that directs cardiac specific expression |
| skeletal | C5-12 | 22 | high level, muscle spec expression to drive target gene |
| skeletal | AdmDys, AdmCTLA4Ig | 32 | muscle creatine kinase promoter |
| smooth muscle | PDE5A | 41 | chromosome 4q26, phosphodiesterase |
| smooth muscle | AlphaTM | 45 | use intronic splicing elements to restrict expression to smooth muscle vs skeletal |
| skeletal | myostatin | 48 | fiber type-specific expression of myostatin |
| Endocrine/nervous | | | |
| glucocorticoid | GR 1B-1E | 4, 12 | glucocorticoid receptor promoter/all cells |
| neuroblastoma | M2-2 | 8, 36 | M2 muscarinic receptor |
| brain | Abeta | 16 | amyloid beta-protein; 30 bp fragment needed for PC12 and glial cell expression |

TABLE 1-continued

| | Promoter | Ref. | Function/comments |
|---|---|---|---|
| brain | enolase | 21 | neuron-specific; high in hippocampus, intermediate in cortex, low in cerebellum |
| synapses | rapsyn | 29 | clusters acetylcholine receptors at neuromuscular junction |
| neuropeptide precursor | VGF | 39 | express limited to neurons in central and peripheral nervous system and specific endocrine cells in adenohypophysis, adrenal medulla, GI tract and pancreas |
| mammalian nervous system | BMP/RA | 46 | use of methylation to control tissue specificity in neural cells. |
| central and peripheral noradrenergic neurons | Phox2a/Phox2b | 47 | regulation of neuron differentiation |
| brain | BAI1-AP4 | 55 | spec to cerebral cortex and hippocampus |
| Gastrointestinal | | | |
| UDP glucoronsyltransferase | UGT1A7 | 11 | gastric mucosa |
| | UGT1A8 | 11 | small intestine and colon |
| | UGT1A10 | 11 | small intestine and colon |
| colon cancer | PKCbetaII | 20 | Protein kinase C betaII (PKCbetaII); express in colon cancer to selectively kill it. |
| Cancer | | | |
| tumor suppressor 4.1B | 4.1B | 5 | 2 isoforms, 1 spec to brain, 1 in kidney |
| nestin | nestin | 63 | second intron regulates tissue specificity |
| cancer spec promoter | hTRT/hSPA1 | 68 | dual promoter system for cancer specificity |
| Blood/lymph system | | | |
| Thyroid | thyroglobulin | 10 | Thyroid spec. -- express to kill thyroid tumors |
| Thyroid | calcitonin | 10 | medullary thyroid tumors |
| Thyroid | GR 1A | 12 | |
| thyroid | thyroglobulin | 50 | regulation controlled by DREAM transcriptional repressor |
| arterial endothelial cells | ALK1 | 60 | activin receptor-like kinase |
| Nonspecific | | | |
| RNA polymerase II | | 7 | |
| gene silencing | Gnasx1, Nespas | 31 | |
| beta-globin | beta globin | 53 | |
| Cardiac | M2-1 | 8 | M2 muscarinic receptor |
| Lung | hBD-2 | 19 | IL-17 induced transcription in airway epithelium |
| pulmonary surfactant protein | SP-C | 62 | Alveolar type II cells |
| ciliated cell-specific prom | FOZJ1 | 70 | use in ciliated epithelial cells for CF treatment |
| surfactant protein expression | SPA-D | 73 | Possible treatment in premature babies |
| Clara cell secretory protein | CCSP | 75 | |
| Dental | | | |
| teeth/bone | DSPP | 28 | extracellular matrix protein dentin sialophosphoprotein |
| Adipose | | | |
| adipogenesis | EPAS1 | 33 | endothelial PAS domain -- role in adipocyte differentiation |
| Epidermal | | | |
| differentiated epidermis | involucrin | 38 | |
| desmosomal protein | CDSN | 58 | stratum granulosum and stratum corneum of epidermis |
| Liver | | | |
| liver spec albumin | Albumin | 49 | |
| serum alpha-fetoprotein | AFP | 56 | liver spec regulation |

REFERENCES

1. Biol Pharm Bull. 2004 November; 27(11):1867-70
2. J Virol. 2004 November; 78(22):12157-68
3. Invest Opthalmol V is Sci. 2004 November; 45(11):3877-84
4. Biochim Biophys Acta. 2004 Oct. 21; 1680(2):114-28
5. Biochim Biophys Acta. 2004 Oct. 21; 1680(2):71-82
6. Curr Cancer Drug Targets. 2004 September; 4(6):531-42
7. Biotechnol Bioeng. 2004 Nov. 20; 88(4):417-25
8. J Neurochem. 2004 October; 91(1):88-98
10. Curr Drug Targets Immune Endocr Metabol Disord. 2004 September; 4(3):235-44
11. Toxicol Appl Pharmacol. 2004 Sep. 15; 199(3):354-63
12. J Immunol. 2004 Sep. 15; 173(6):3816-24
13. Thromb Haemost. 2004 September; 92(3):495-502
14. Acad Radiol. 2004 September; 11(9):1022-8
15. Development. 2004 September; 131(18):4447-54
16. J Neurochem. 2004 September; 90(6):1432-44
17. Mol Ther. 2004 September; 10(3):545-52

18. Development. 2004 October; 131(19):4709-23. Epub 2004 Aug. 25
19. J Immunol. 2004 Sep. 1; 173(5):3482-91
20. J Biol Chem. 2004 Oct. 29; 279(44):45556-63. Epub 2004 Aug. 20
21. J Biol Chem. 2004 Oct. 22; 279(43):44795-801. Epub 2004 Aug. 20
22. Hum Gene Ther. 2004 August; 15(8):783-92
25. Nucleic Acids Res. 2004 Aug. 9; 32(14):4155-65. Print 2004
26. Mol Imaging. 2004 April; 3(2):69-75
27. J Gene Med. 2004 August; 6(8):906-12
28. J Biol Chem. 2004 Oct. 1; 279(40):42182-91. Epub 2004 Jul. 28
29. Mol Cell Biol. 2004 August; 24(16):7188-96
31. Nat Genet. 2004 August; 36(8):894-9. Epub 2004 Jul. 25
32. Gene Ther. 2004 October; 11(19):1453-61
33. J Biol Chem. 2004 Sep. 24; 279(39):40946-53. Epub 2004 Jul. 15
36. Brain Res Mol Brain Res. 2004 Jul. 26; 126(2):173-80
38. J Invest Dermatol. 2004 August; 123(2):313-8
39. Cell Mol Neurobiol. 2004 August; 24(4):517-33
41. Int J Impot Res. 2004 June; 16 Suppl 1:S8-S10
42. Invest Opthalmol V is Sci. 2004 July; 45(7):2194-200
45. J Biol Chem. 2004 Aug. 27; 279(35):36660-9. Epub 2004 Jun. 11
46. Brain Res Mol Brain Res. 2004 Jun. 18; 125(1-2):47-59
47. Brain Res Mol Brain Res. 2004 Jun. 18; 125(1-2):29-39
48. Am J Physiol Cell Physiol. 2004 October; 287(4):C1031-40. Epub 2004 Jun. 9
49. Xi Bao Yu Fen Zi Mian Yi Xue Za Zhi. 2003 November; 19(6):601-3
50. J Biol Chem. 2004 Aug. 6; 279(32):33114-22. Epub 2004 Jun. 4
53. Brief Funct Genomic Proteomic. 2004 February; 2(4):344-54
55. FEBS Lett. 2004 May 21; 566(1-3):87-94
56. Biochem Biophys Res Commun. 2004 Jun. 4; 318(3):773-85
58. J Invest Dermatol. 2004 March; 122(3):730-8
59. Mol Vis. 2004 Mar. 26; 10:208-14
60. Circ Res. 2004 Apr. 30; 94(8):e72-7. Epub 2004 Apr. 1
62. Am J Physiol Lung Cell Mol Physiol. 2004 Dec. 3; [Epub ahead of print]
63. Lab Invest. 2004 December; 84(12):1581-92
67. Prostate. 2004 Jun. 1; 59(4):370-82
68. Cancer Res. 2004 Jan. 1; 64(1):363-9
70. Mol Ther. 2003 October; 8(4):637-45
73. Front Biosci. 2003 May 1; 8:d751-64
75. Am J Respir Cell Mol Biol. 2002 August; 27(2):186-93

TABLE 2

| Gene-protein target* | Cellular function | Type of cancer tested |
|---|---|---|
| B-raf | Serine/threonine kinase | Malignant melanoma |
| Nox1 | Superoxide-generating oxidase | Transformed MRK cells[a] |
| FAS/Her2 | Fatty acid synthase | Breast-MDA-MB-231 |
| Cyclin E | Cell-cycle control | Hepatocarcinoma |
| Hec1 | Chromosomal segregation | |
| Gp210 | Nuclear pore assembly | Adenocarcinoma (Hela cells) |
| c-Kit | Signal transduction | Gastrointestinal |
| MDR | Multi-drug resistance | Adenocarcinoma (Hela cells) |
| bcl-2 | Antiapoptotic | Esophageal adenocarcinoma |
| livin | Antiapoptotic | Adenocarcinoma |
| survivin | Antiapoptotic | Adenocarcinoma (Hela cells) |

TABLE 2-continued

| Gene-protein target* | Cellular function | Type of cancer tested |
|---|---|---|
| Philadelphia chromosome | | Chronic myeloid leukemia |
| Ribonucleotide reductase | Gemcitabine resistance | Hepatic metastasis |
| Rho C | Cell motility | Metastasis |

[a]Normal rat kidney cells.
*Genes are written in italics and lower case letters while proteins begin with a capital letter and are written in roman letters.

TABLE 3

| Genetic Disorder | Gene | Chromosome |
|---|---|---|
| Hemophilia | | |
| Depression | CRHR1 | |
| SCIDS | SCID-X1 | X |
| Breast Cancer | ESR1 | |
| | BRCA1 | |
| | BRCA2 | |
| | p53 | |
| Lupus (SLAM/C D2 | Sles1 | |
| | Sles2 | |
| | Sles3 | |
| | Sles4 | |
| Colon Cancer | 15-PGDH | |
| | MSH2 | 2 |
| | MSH6 | 2 |
| | MLH1 | 3 |
| Crohn's Disease | CD 19 | 16 |
| | sialophorin | |
| | CD11 integrin | |
| | IL-4 | |
| Cystic Fibrosis | CFTR | |
| Type I Diabetes | IDDM1 | 6 |
| | IDDM2 | 11 |
| | GCK (glucokinase) | 7 |
| Glucose/Galactose Malabsorption (CGM) | SGLT1 | 22 |
| Pancreatic Cancer | DPC4 (Smad4) | 18 |
| | p53 | |
| | Rb | |
| Wilson's disease | ATP7B | 13 |
| Zellweger syndrome | PXR 1 | 12 |
| Sickle Cell Anemia | HBB | 11p15.4 |
| Burkitt Lymphoma | Myc | 8 |
| Gaucher disease | glucocerebroside | |
| Hemophilia A | HEMA (Factor VIII) | X |
| Chronic Myeloid leukemia | ABL (9) BCR (22) | 9/22 exchange |
| Niemann-Pick Type A, B or C | NP-C | 18 |
| Hemoglobinuria (PNH) Porphyria | PIG-A | X |
| Thalassemia alpha | HBA1 | 16 |
| | HBA2 | 16 |
| Thalassemia beta | HBB | 11 |
| Small cell lung carcinoma | | 3 |
| Melanoma | CDKN2 | 9 |
| Multiple endocrine neoplasia | MEN1 | 11 |
| Neurofibromatosis | NF-2 | 22 |
| Li-Fraumeni syndrome | p53 | 17 |
| | Rb | 13 |
| Polycystic Kidney Disease | PKD1 | 16 |
| Prostate cancer | HPC1 | 1 |
| Harvey Ras oncogene | Ras | 11 |
| Tuberous sclerosis | TSC1 | 9 |
| | TSC2 | 16 |
| Von-Hippel Lindau | VHL | 3 |
| Deafness | Cx26 | 13q11-12 |
| Pendred syndrome | PDS | 7 |
| Best disease | VMD2 | 11 |
| Glaucoma | GLC1A | 1 |
| gyrate atrophy | OAT | 10 |
| Rett syndrome | MeCP2 | Xq28 |

TABLE 3-continued

| Genetic Disorder | Gene | Chromosome |
| --- | --- | --- |
| Congenital adrenal hyperplasia | CYP21P | 6 |
| Adrenaleukodystrophy | ALD | |
| AI polyglandular syndromeI | AIRE | 21 |
| Cockayne syndrome Type I | CSA | 5 |
| Cockayne syndrome Type II | CSB | |
| Diastrophic dysplasia | DTD | 5 |
| Ataxia telangiectasia | ATM | 11 |
| Atherosclerosis | Apo E | 19 |
| Long QT syndrome | LQT1 | 11 |
| Williams Syndrome | LIM kinase, elastin | 7 |
| Asthma | | 5, 6, 11, 14, 12 |
| DiGeorge syndrome | | 22 |
| Hyper-IgM | TNFSF5 | Xq26 |
| Severe Combined Immuno-deficiency Disease (SCID) | IL2RG | X |
| | JAK3 | 19 |
| | ADA | 20 |
| Alport Syndrome | COL4A5 | X |
| 5-alpha reductase | | 5 |
| Achondroplasia | FGFR3 | 4 |
| Familial ALS | SOD1 | 21 |
| Charcot-Marie-Tooth disease Type 1A | PMP22 | 17 |
| Charcot-Marie-Tooth disease Type 1B | | X |
| Dejerine-Sottas Syndrome | | |
| Duchenne muscular dystrophy | dystrophin | X |

TABLE 3-continued

| Genetic Disorder | Gene | Chromosome |
| --- | --- | --- |
| Ellis-van Creveld syndrome | EVC | 4 |
| Fibrodysplasia Ossificans Progressiva | NOG | |
| | BMP | |
| Marfan Syndrome | FBN1 | 15 |
| Myotonic dystrophy | myotonic dystrophy | 19 |
| Fragile X | FMR1 | X |
| PWS | SNRPN | 15 |
| Waardenburg syndrome | Pax3 | 2 |
| Werner disease | SGS1 | 8 |
| Alzheimer disease | PS1 | 14 |
| | PS2 | 1 |
| Angelman syndrome | deletion 15q11q13 | 15 |
| | UBE3A | |
| Essential tremor | ETM1 | 3 |
| | ETM2 | 2 |
| Familial Mediterranean fever | FMF | 16 |
| Friedereich's ataxia | YFH1 | |
| Huntington's disease | HD | 4 |
| Maple Syrup Urine Disease | BCKDH complex | |
| Parkinson's | Alpha-synuclein | 4 |
| Refsum disease | PAHX | 10 |
| Spinal Muscular Atrophy | SMN1 | 5 |
| | SMN2 | |
| spinocerebellar ataxia | SCA1 | 6 |
| Tangier Disease | ABC1 | 9q31 |
| Tay-Sach's | HEXA | 15 |
| Obesity | leptin | 7 |
| AAT | SERPINA 1 | 14 |
| Hemochromatosis | HFE (mutation C282Y) | |
| | HFW (mutation H63D) | |

We claim:

1. A transposon-based vector comprising an isolated polynucleotide sequence comprising:
   a) a gene operably linked to a first promoter wherein the first promoter is an SV 40 promoter, the gene encoding for a transposase; and,
   b) one or more genes of interest encoding for a protein selected from the group consisting of SEQ ID NO: 44, 45 and 46, the one or more genes of interest being operably-linked to one or more additional promoters, the one or more genes of interest and their operably-linked promoters are flanked by transposase insertion sequences recognized by the transposase, and the one or more additional promoters are cell-specific promoters or constitutive promoters.

2. The transposon-based vector of claim 1, further comprising a cecropin B polyA nucleotide sequence located 3' to the one or more genes of interest.

3. The transposon-based vector of claim 2, wherein the cecropin B polyA nucleotide sequence is optimized for production of a protein encoded by the one or more genes of interest.

4. An isolated polynucleotide sequence comprising:
   a) one or more genes of interest encoding for a protein selected from the group consisting of SEQ ID NO: 44, 45 and 46, the one or more genes of interest being operably-linked to one or more promoters;
   b) a cecropin B polyA nucleotide sequence located 3' to the one or more genes of interest; and,
   c) transposase insertion sequences recognized by a bacterial transposase, the one or more genes of interest and their operably-linked promoters are flanked by the transposase insertion sequences and the one or more additional promoters are cell-specific promoters or constitutive promoters.

5. The transposon-based vector of claim 1, further comprising at least one of: (a) a Kozak sequence positioned so as to include at least the first codon of the transposase gene; (b) two stop codons operably-linked to the transposase gene; (c) a modified transposase gene sequence, wherein at least one of the first twenty codons of the transposase gene is modified by changing a nucleotide at a third base position of the codon to an adenine or thymine without modifying the amino acid encoded by the codon; or (d) a polyA sequence operably-linked to the transposase gene.

6. A composition comprising the transposon-based vector of claim 1 and a carrier suitable for administration to an animal or a human.

7. The transposon-based vector of claim 1, the SV40 promoter being linked at its 3' end to a preprosequence of cecropin B.

* * * * *